United States Patent
Wilson et al.

(10) Patent No.: US 9,259,317 B2
(45) Date of Patent: Feb. 16, 2016

(54) SYSTEM AND METHOD FOR IMPLANTING A HEART IMPLANT

(75) Inventors: Jonathan E. Wilson, Mattapoisett, MA (US); Christopher W. Maurer, Wakefield, MA (US); Thomas C. Piemonte, Dover, MA (US); Carl Kirker-Head, Sturbridge, MA (US)

(73) Assignee: Cardiosolutions, Inc., West Bridgewater, MA (US)

( * ) Notice: Subject to any disclaimer, the term of this patent is extended or adjusted under 35 U.S.C. 154(b) by 0 days.

(21) Appl. No.: 12/209,686

(22) Filed: Sep. 12, 2008

(65) Prior Publication Data

US 2009/0048668 A1 Feb. 19, 2009

Related U.S. Application Data

(60) Provisional application No. 61/061,343, filed on Jun. 13, 2008.

(51) Int. Cl.
*A61F 2/24* (2006.01)
*A61B 17/34* (2006.01)

(52) U.S. Cl.
CPC .............. *A61F 2/246* (2013.01); *A61F 2/2466* (2013.01); *A61B 17/3478* (2013.01)

(58) Field of Classification Search
CPC ......... A61F 2/24; A61F 2/2487; A61F 2/246; A61F 2/2466
USPC .......................... 623/2.2–2.25, 2.27; 606/200
See application file for complete search history.

(56) References Cited

U.S. PATENT DOCUMENTS

| | | |
|---|---|---|
| 2,549,731 A | 4/1951 | Wattley |
| 2,625,967 A | 1/1953 | Stull |
| 3,197,788 A | 8/1965 | Segger |
| 3,445,916 A | 5/1969 | Schulte |
| 3,551,913 A | 1/1971 | Shiley et al. |
| 3,586,029 A | 6/1971 | Evers |
| 3,589,392 A | 6/1971 | Meyer |

(Continued)

FOREIGN PATENT DOCUMENTS

| | | |
|---|---|---|
| EP | 0125393 | 11/1984 |
| EP | 1323438 | 2/2003 |

(Continued)

OTHER PUBLICATIONS

Eisenhauer et al., Closure of Prosthetic Paravalvular Mitral Regurgitation With the Gianturco-Grifka Vascular Occlusion Device, Catheterization and Cardiovascular Interventions, 2001, 5 pages, vol. 54.

(Continued)

*Primary Examiner* — Brian Pellegrino
(74) *Attorney, Agent, or Firm* — Reza Mollaaghababa; Thomas Engellenner; Pepper Hamilton LLP

(57) ABSTRACT

A method and system according to one embodiment may include a plurality of apparatus configured to percutaneously deliver a heart valve implant. The method and system may include an implant comprising an anchor configured to engage cardiac tissue, a shaft coupled to the anchor, and a valve body coupled to the shaft. The method and system may further include at least partially collapsing the heart valve implant and percutaneously inserting the heart valve implant into a heart. The percutaneously inserted implant may be secured within the heart and may then be expanded.

23 Claims, 38 Drawing Sheets

OUTSIDE VIEW OF IMPLANT

(56) References Cited

U.S. PATENT DOCUMENTS

| | | |
|---|---|---|
| 3,671,979 A | 6/1972 | Moulopoulos |
| 3,689,942 A | 9/1972 | Rapp |
| 3,714,671 A | 2/1973 | Edwards et al. |
| 3,739,402 A | 6/1973 | Cooley et al. |
| 3,983,581 A | 10/1976 | Angell et al. |
| 4,079,468 A | 3/1978 | Liotta et al. |
| 4,084,268 A | 4/1978 | Ionescu et al. |
| 4,259,753 A | 4/1981 | Liotta et al. |
| 4,291,420 A | 9/1981 | Reul |
| 4,297,749 A | 11/1981 | Davis et al. |
| 4,439,185 A | 3/1984 | Lundquist |
| 4,535,757 A | 8/1985 | Webster, Jr. |
| 4,597,767 A | 7/1986 | Lenkei |
| 4,865,030 A | 9/1989 | Polyak |
| 4,960,424 A | 10/1990 | Grooters |
| 5,002,067 A | 3/1991 | Berthelsen et al. |
| 5,217,484 A | 6/1993 | Marks |
| 5,222,973 A | 6/1993 | Sharpe et al. |
| 5,261,916 A | 11/1993 | Engelson |
| 5,304,195 A | 4/1994 | Twyford, Jr. et al. |
| 5,308,357 A | 5/1994 | Lichtman |
| 5,318,589 A | 6/1994 | Lichtman |
| 5,350,397 A | 9/1994 | Palermo et al. |
| 5,397,351 A | 3/1995 | Pavcnik et al. |
| 5,411,552 A | 5/1995 | Andersen et al. |
| 5,415,667 A | 5/1995 | Frater |
| 5,462,527 A | 10/1995 | Stevens-Wright et al. |
| 5,509,428 A | 4/1996 | Dunlop |
| 5,554,185 A | 9/1996 | Block et al. |
| 5,582,607 A | 12/1996 | Lackman |
| 5,611,800 A | 3/1997 | Davis et al. |
| 5,634,936 A | 6/1997 | Linden et al. |
| 5,638,827 A | 6/1997 | Palmer et al. |
| 5,649,949 A | 7/1997 | Wallace et al. |
| 5,653,712 A | 8/1997 | Stern |
| 5,665,100 A | 9/1997 | Yoon |
| 5,776,075 A | 7/1998 | Palmer |
| 5,792,179 A | 8/1998 | Sideris |
| 5,797,958 A | 8/1998 | Yoon |
| 5,814,098 A | 9/1998 | Hinnenkamp et al. |
| 5,840,081 A | 11/1998 | Andersen et al. |
| 5,891,130 A | 4/1999 | Palermo et al. |
| 5,895,391 A | 4/1999 | Farnholtz |
| 5,928,224 A | 7/1999 | Laufer |
| 5,957,865 A | 9/1999 | Backman et al. |
| 5,957,949 A | 9/1999 | Leonhardt et al. |
| 5,989,242 A | 11/1999 | Saadat et al. |
| 5,993,474 A | 11/1999 | Ouchi |
| 6,090,096 A | 7/2000 | St. Goar et al. |
| 6,152,144 A | 11/2000 | Lesh et al. |
| 6,168,614 B1 | 1/2001 | Andersen et al. |
| 6,183,512 B1 | 2/2001 | Howanec et al. |
| 6,190,373 B1 | 2/2001 | Palermo et al. |
| 6,217,610 B1 | 4/2001 | Carpentier et al. |
| 6,283,127 B1 | 9/2001 | Sterman et al. |
| 6,283,995 B1 | 9/2001 | Moe et al. |
| 6,287,339 B1 | 9/2001 | Vazquez et al. |
| 6,332,893 B1 | 12/2001 | Mortier et al. |
| 6,358,277 B1 | 3/2002 | Duran |
| 6,415,693 B1 | 7/2002 | Simon et al. |
| 6,416,549 B1 | 7/2002 | Chinn et al. |
| 6,419,695 B1 | 7/2002 | Gabbay |
| 6,440,132 B1 | 8/2002 | Jackson |
| 6,454,798 B1 | 9/2002 | Moe |
| 6,461,382 B1 | 10/2002 | Cao |
| 6,482,228 B1 | 11/2002 | Norred |
| 6,508,825 B1 | 1/2003 | Selmon et al. |
| 6,592,606 B2 * | 7/2003 | Huter et al. ............... 606/200 |
| 6,629,534 B1 | 10/2003 | St Goar et al. |
| 6,652,578 B2 | 11/2003 | Bailey et al. |
| 6,673,100 B2 | 1/2004 | Diaz et al. |
| 6,682,559 B2 | 1/2004 | Myers et al. |
| 6,695,866 B1 | 2/2004 | Kuehn et al. |
| 6,746,404 B2 | 6/2004 | Schwartz |
| 6,764,510 B2 | 7/2004 | Vidlund et al. |
| 6,767,362 B2 | 7/2004 | Schreck |
| 6,769,434 B2 | 8/2004 | Liddicoat et al. |
| 6,805,711 B2 | 10/2004 | Quijano et al. |
| 6,821,297 B2 | 11/2004 | Snyders |
| 6,830,584 B1 | 12/2004 | Seguin |
| 6,830,585 B1 | 12/2004 | Artof et al. |
| 6,849,081 B2 | 2/2005 | Sepetka et al. |
| 6,869,444 B2 | 3/2005 | Gabbay |
| 6,896,700 B2 | 5/2005 | Lu et al. |
| 6,911,043 B2 | 6/2005 | Myers et al. |
| 6,964,684 B2 | 11/2005 | Ortiz et al. |
| 6,971,998 B2 | 12/2005 | Rosenman et al. |
| 6,974,476 B2 | 12/2005 | McGuckin, Jr. et al. |
| 6,976,950 B2 * | 12/2005 | Connors et al. ............... 600/29 |
| 7,018,406 B2 | 3/2006 | Seguin et al. |
| 7,056,286 B2 | 6/2006 | Ravenscroft et al. |
| 7,070,618 B2 | 7/2006 | Streeter |
| 7,077,862 B2 | 7/2006 | Vidlund et al. |
| 7,101,395 B2 | 9/2006 | Tremulis et al. |
| 7,112,219 B2 | 9/2006 | Vidlund et al. |
| 7,160,322 B2 | 1/2007 | Gabbay |
| 7,189,199 B2 | 3/2007 | McCarthy et al. |
| 7,247,134 B2 | 7/2007 | Vidlund et al. |
| 7,335,213 B1 | 2/2008 | Hyde et al. |
| 7,344,553 B2 | 3/2008 | Opolski et al. |
| 7,374,572 B2 | 5/2008 | Gabbay |
| 7,381,210 B2 | 6/2008 | Zarbatany et al. |
| 7,404,824 B1 | 7/2008 | Webler et al. |
| 7,657,326 B2 | 2/2010 | Bodner et al. |
| 7,678,145 B2 | 3/2010 | Vidlund et al. |
| 7,704,268 B2 | 4/2010 | Chanduszko |
| 7,753,949 B2 | 7/2010 | Lamphere et al. |
| 7,785,366 B2 | 8/2010 | Maurer et al. |
| 7,927,370 B2 | 4/2011 | Webler et al. |
| 7,942,928 B2 | 5/2011 | Webler et al. |
| 7,963,973 B2 | 6/2011 | Nguyen et al. |
| 8,092,525 B2 | 1/2012 | Eliasen et al. |
| 8,118,822 B2 | 2/2012 | Schaller et al. |
| 8,216,302 B2 | 7/2012 | Wilson et al. |
| 8,486,136 B2 | 7/2013 | Maurer et al. |
| 8,506,623 B2 | 8/2013 | Wilson et al. |
| 2001/0007956 A1 | 7/2001 | Letac et al. |
| 2001/0010017 A1 | 7/2001 | Cribier et al. |
| 2001/0018611 A1 | 8/2001 | Solem et al. |
| 2002/0029080 A1 | 3/2002 | Mortier et al. |
| 2002/0032480 A1 | 3/2002 | Spence et al. |
| 2002/0042651 A1 | 4/2002 | Liddicoat et al. |
| 2002/0058995 A1 | 5/2002 | Stevens |
| 2002/0077566 A1 | 6/2002 | Laroya et al. |
| 2002/0081553 A1 | 6/2002 | Tramonte |
| 2002/0169377 A1 | 11/2002 | Khairkhahan et al. |
| 2002/0169502 A1 | 11/2002 | Mathis |
| 2002/0183838 A1 | 12/2002 | Liddicoat et al. |
| 2002/0188170 A1 * | 12/2002 | Santamore et al. ............... 600/37 |
| 2003/0033009 A1 | 2/2003 | Gabbay |
| 2003/0040792 A1 | 2/2003 | Gabbay |
| 2003/0105519 A1 | 6/2003 | Fasol et al. |
| 2003/0120264 A1 | 6/2003 | Lattouf |
| 2003/0130731 A1 | 7/2003 | Vidlund et al. |
| 2003/0139751 A1 | 7/2003 | Evans et al. |
| 2003/0144574 A1 | 7/2003 | Heilman et al. |
| 2003/0181945 A1 | 9/2003 | Opolski et al. |
| 2003/0199975 A1 | 10/2003 | Gabbay |
| 2003/0208203 A1 | 11/2003 | Lim et al. |
| 2003/0212453 A1 | 11/2003 | Mathis et al. |
| 2004/0034366 A1 | 2/2004 | van der Burg et al. |
| 2004/0044402 A1 | 3/2004 | Jung et al. |
| 2004/0088047 A1 | 5/2004 | Spence et al. |
| 2004/0106989 A1 | 6/2004 | Wilson et al. |
| 2004/0122512 A1 | 6/2004 | Navia et al. |
| 2004/0127981 A1 | 7/2004 | Rahdert et al. |
| 2004/0127983 A1 | 7/2004 | Mortier et al. |
| 2004/0148020 A1 | 7/2004 | Vidlund et al. |
| 2004/0181256 A1 | 9/2004 | Glaser |
| 2004/0210304 A1 | 10/2004 | Seguin et al. |
| 2004/0210307 A1 | 10/2004 | Khairkhahan |
| 2004/0225353 A1 | 11/2004 | McGuckin, Jr. et al. |
| 2004/0225354 A1 | 11/2004 | Allen et al. |
| 2004/0243229 A1 | 12/2004 | Vidlund et al. |

(56) References Cited

U.S. PATENT DOCUMENTS

| | | |
|---|---|---|
| 2004/0260322 A1 | 12/2004 | Rudko et al. |
| 2005/0021056 A1 | 1/2005 | St. Goar et al. |
| 2005/0027337 A1 | 2/2005 | Rudko et al. |
| 2005/0033446 A1 | 2/2005 | Deem et al. |
| 2005/0038508 A1 | 2/2005 | Gabbay |
| 2005/0038509 A1 | 2/2005 | Ashe |
| 2005/0065591 A1 | 3/2005 | Moberg et al. |
| 2005/0070999 A1 | 3/2005 | Spence |
| 2005/0075727 A1 | 4/2005 | Wheatley |
| 2005/0090824 A1 | 4/2005 | Shluzas et al. |
| 2005/0131451 A1 | 6/2005 | Kleshinski et al. |
| 2005/0149182 A1 | 7/2005 | Alferness et al. |
| 2005/0159810 A1 | 7/2005 | Filsoufi |
| 2005/0222488 A1* | 10/2005 | Chang et al. ............. 600/37 |
| 2005/0288786 A1 | 12/2005 | Chanduszko |
| 2006/0020335 A1 | 1/2006 | Kowalsky et al. |
| 2006/0025855 A1 | 2/2006 | Lashinski et al. |
| 2006/0058871 A1 | 3/2006 | Zakay et al. |
| 2006/0084943 A1 | 4/2006 | Rosenman et al. |
| 2006/0129025 A1 | 6/2006 | Levine et al. |
| 2006/0149368 A1 | 7/2006 | Spence |
| 2006/0155326 A1 | 7/2006 | Aranyi |
| 2006/0178700 A1 | 8/2006 | Quinn |
| 2006/0195012 A1 | 8/2006 | Mortier et al. |
| 2006/0195185 A1 | 8/2006 | Lane et al. |
| 2006/0199995 A1 | 9/2006 | Vijay |
| 2006/0229708 A1 | 10/2006 | Powell et al. |
| 2006/0241745 A1 | 10/2006 | Solem |
| 2006/0253072 A1 | 11/2006 | Pai et al. |
| 2006/0293698 A1 | 12/2006 | Douk |
| 2007/0016286 A1 | 1/2007 | Herrmann et al. |
| 2007/0049980 A1 | 3/2007 | Zielinski et al. |
| 2007/0093890 A1 | 4/2007 | Eliasen et al. |
| 2007/0118151 A1 | 5/2007 | Davidson |
| 2007/0149995 A1 | 6/2007 | Quinn et al. |
| 2007/0167981 A1 | 7/2007 | Opolski et al. |
| 2007/0185571 A1 | 8/2007 | Kapadia et al. |
| 2007/0198050 A1 | 8/2007 | Ravenscroft et al. |
| 2007/0198082 A1 | 8/2007 | Kapadia et al. |
| 2007/0213578 A1 | 9/2007 | Khairkhahan et al. |
| 2007/0232981 A1 | 10/2007 | Ravenscroft et al. |
| 2007/0232992 A1* | 10/2007 | Kutsko et al. ............. 604/30 |
| 2007/0239154 A1 | 10/2007 | Shaolian et al. |
| 2007/0255399 A1 | 11/2007 | Eliasen et al. |
| 2007/0265700 A1 | 11/2007 | Eliasen et al. |
| 2007/0282429 A1 | 12/2007 | Hauser et al. |
| 2007/0293943 A1 | 12/2007 | Quinn |
| 2008/0125860 A1 | 5/2008 | Webler et al. |
| 2008/0125861 A1 | 5/2008 | Webler et al. |
| 2008/0183105 A1 | 7/2008 | Greenhalgh et al. |
| 2008/0195200 A1 | 8/2008 | Vidlund et al. |
| 2008/0288061 A1 | 11/2008 | Maurer et al. |
| 2009/0043382 A1 | 2/2009 | Maurer et al. |
| 2009/0048668 A1 | 2/2009 | Wilson et al. |
| 2009/0105814 A1 | 4/2009 | Groothuis et al. |
| 2009/0131849 A1 | 5/2009 | Maurer et al. |
| 2009/0131880 A1 | 5/2009 | Speziali et al. |
| 2009/0132033 A1 | 5/2009 | Maurer et al. |
| 2009/0163934 A1 | 6/2009 | Raschdorf, Jr. et al. |
| 2009/0240326 A1 | 9/2009 | Wilson et al. |
| 2010/0022948 A1 | 1/2010 | Wilson et al. |
| 2010/0324668 A1 | 12/2010 | Maurer et al. |
| 2012/0143320 A1 | 6/2012 | Eliasen et al. |

FOREIGN PATENT DOCUMENTS

| | | |
|---|---|---|
| GB | 1264472 | 2/1972 |
| GB | 1268484 | 3/1972 |
| GB | 1388064 | 3/1975 |
| WO | 03/049619 | 6/2003 |
| WO | WO2006032051 | 3/2006 |
| WO | 2006/064490 A1 | 6/2006 |
| WO | 2006091597 | 8/2006 |
| WO | 2006/111391 | 10/2006 |
| WO | 2006127509 | 11/2006 |
| WO | 2007064810 | 6/2007 |
| WO | 2007078772 | 7/2007 |
| WO | 2007100409 | 9/2007 |
| WO | 2007/140470 A2 | 12/2007 |
| WO | 2008079828 | 7/2008 |
| WO | 2009053952 A2 | 4/2009 |

OTHER PUBLICATIONS

Hourihan et al., Transcatheter Umbrella Closure of Valvular and Paravalvular Leaks, American College of Cardiology, Nov. 15, 1992, 7 pages, vol. 20, No. 6.

Moscucci et al., Coil Embolization of a Periprosthetic Mitral Valve Leak Associated With Severe Hemolytic Anemia, Images in Cardiovascular Medicine, American Heart Association, Inc., 2001, 2 pages, vol. 104.

Rashkind et al. Nonsurgical closure of patent ductus arteriosus: clinical application of the Rashkind PDA Occluder System, Therapy and Prevention—Congenital Heart Disease, Mar. 1987, 10 pages, vol. 75, No. 3.

Ryhänen et al., Invivo biocompatibility evaluation of nickel-titanium shape memory metal alloy: Muscle and perineural tissue responses and encapsule membrane thickness, Muscle and Perineural Tissue Response to Nitinol, Received Aug. 11, 1997; accepted Jan. 19, 1998, 8 pages.

International Search Report and Written Opinion dated Jan. 16, 2009 issued in PCT Application No. PCT/US08/83497, 10 pages.

Balzer et al., Real-time transesophageal three-dimensional echocardiography for guidance of percutaneous cardiac interventions: first experience, Clinical Research in Cardiology, May 29, 2008, 565-574, vol. 97, No. 9.

Carlson et al., Lead Perforation: Incidence in Registries, Pace Industry Viewpoint, Jan. 2008, 13-15, vol. 31.

Clinical Trials.gov, Comparing the Effectiveness of a Mitral Valve Repair Procedure in Combination With Coronary Artery Bypass Grafting (CABG) Versus CABG Alone in People with Moderate Ischemic Mitral Regurgitation, http://clinicaltrials.gov/ct2/show/record/NCT00806988?term=mitral+repair&rank=7, Feb. 24, 2009, 1-3.

Clinical Trials.gov, Safety and Efficacy Study of the PTMA Device to Reduce Mitral Valve Regurgitation in Patients With Heart Failure (PTOLEMY2Canada), http://clinicaltrials.gov/ct2/show/study/NCT00815386?term=Viacor&rank=3, 1-3.

Clinical Trials.gov, Study of Safety and Efficacy of the Percutaneous Reduction of Mitral Valve Regurgitation in Heart Failure Patients (PTOLEMY-2), http://clinicaltrials.gov/ct2/show/NCT00787293?term=Viacor&rank=5, 1-2.

Cohen, Trans-Septal Technique for Tandemheart Insertion, Lenox Hill Heart and Vascular Institute of New York, Barcelona May 22-May 25, 2007, 18 pages.

Corbisiero et al., Does Size Really Matter? A Comparison of the Riata Lead Family Based on Size and Its Relation to Performance, Pace, Jun. 2008, vol. 31, 722-726.

Criber et al., Treatment of Calcific Aortic Stenosis With the Percutaneous Heart Valve—Mid-Term Follow-Up From the Initial Feasibility Studies: The French Experience, Journal of the American College of Cardiology, Mar. 21, 2006, vol. 47, No. 6, 1241-1223.

Danik et al., Timing of delayed perforation with the St. Jude Riata lead: A single-center experience and a review of the literature, Heart Rhythm Society, Dec. 2008, vol. 5, No. 12, 1667-1672.

Del Valle-Fernández et al., Transcatheter heart valves for the treatment of aortic stenosis: state-of-the-art, Minerva Cardioangiologica, Oct. 2008, vol. 56, No. 5, 543-556.

Douthitt, Cardiac Dimensions® Inc. Receives CE Mark for Carillon™ Mitral Contour System™, Cardiac Dimensions—News, htpp://www.cardiacdimensions.com/usa/press-release-2-4-09.html, downloaded Feb. 24, 2009, 1-2.

Dvorin, Endovalve Inc., Pioneering percutaneous mitral valve replacement., Start-Up Windhover's Review of Emerging Medical Ventures, Jun./Jul. 2006, vol. 11, No. 7, 1-2.

Eltchaninoff, Clinical results of percutaneous aortic valve implantation, Euro PCR07, Cribier-Edwards, 30 pages.

(56) References Cited

OTHER PUBLICATIONS

Evalve reports 1st MitraClip treatments in the Netherlands, Medical Device Daily, Feb. 19, 2009, vol. 13, No. 32, 2 pages.
A first for MiCardia's Dynoplasty, Medical Device Daily, Feb. 19, 2009, vol. 13, No. 32, 1 page.
Fitts et al. , Fluoroscopy-Guided Femoral Artery Puncture Reduces the Risk of PCI-Related Vascular Complications, Journal of Interventional Cardiology, vol. 21, No. 3, 2008, 273-278.
Gelsomino et al., Left ventricular diastolic function after restrictive mitral ring annuloplasty in chronic ischemic mitral regurgitation and its predictive value on outcome and recurrence of regurgitation, International Journal of Cardiology, vol. 132, 2009, 419-428.
Geyfman et al., Cardiac Tamponade as Complication of Active-Fixation Atrial Lead Perforations: Proposed Mechanism and Management Algorithm, PACE, Apr. 2007, vol. 30, 498-501.
Gorman et al., Surgical Therapy for Mitral Regurgitation: The Key to Preventing Heart Failure?, Prevention of Heart Failure After Myocardial Infarction, 2008, 211-215.
Harper, Evalve Announces Enrollment Completion of the Everest Randomized Study, http://www.evalveinc.com/europe/press/17.html, downloaded Feb. 24, 2009, 1-3.
Harper, Two-Year Follow-Up Data Demonstrates Preservation of Adequate Mitral Valve Area in Patients Treated with the MitraClip®-system, http://www.evalveinc.com/europe/press/21.html, downloaded Feb. 24, 2009, 1-3.
Hung et al., 3D Echocardiography: A Review of the Current Status and Future Directions, ASE Position Paper, Journal of the American Society of Echocardiography, Mar. 2007, 213-233.
Hung et al., Mechanism of Dynamic Regurgitant Orifice Area Variation of Functional Mitral Regurgitation—Physiologic Insights From the Proximal Flow Convergence Technique, Journal of the American College of Cardiology, Feb. 1999, vol. 33, No. 2, 538-545.
Hung et al., A Novel Approach for Reducing Ischemic Mitral Regurgitation by Injection of a Polymer of Reverse Remodel and Reposition Displaced Papillary Muscles, Circulation—Journal of the American Heart Association, Sep. 30, 2008, Downloaded from circ.ahajournals.org at National Insthealth Lib on Feb. 25, 2009, S262-S269.
Hytowitz, First U.S. Patients Enrolled in the Realism Continued Access Study, evalve, http://www.evalveinc.com/europe/press/22/html, downloaded Feb. 24, 2009, 2 pages.
International Search Report and Written Opinion dated Feb. 25, 2009 issued in PCT Application No. PCT/US08/83570, 13 pages.
International Search Report and Written Opinion dated Apr. 2, 2009 issued in PCT Application No. PCT/US08/83574, 8 pages.
Jilaihawi et al., Percutaneous Aortic Valve Replacement in Patients with Challenging Aortoiliofemoral Access, Catheterization and Cardiovascular Interventions, 2008, vol. 72, 885-890.
Jovin et al., Atrial Fibrillation and Mitral Valve Repair, Pace, Aug. 2008, vol. 31, 1057-1063.
Kahlert et al., Direct Assessment of Size and Shape of Noncircular Vena Contracta Area in Functional Versus Organic Mitral Regurgitation Using Real-Time Three-Dimensional Echocardiography, Valvular Heart Disease, Journal of the American Society of Echocardiography, Aug. 2008, vol. 21, No. 8, 912-921.
Kempfert et al, Minimally invasive off-pump valve-in-a-valve implantation: the atrial transcatheter approach for re-operative mitral valve replacement, European Heart Journal, 2008, vol. 29, 2382-2387.
Kerensky, Complications of Cardiac Catheterization and Strategies to Reduce Risks, Diagnostic and Therapeutic Cardiac Catheterization—Third Edition—Chapter 8, 1998, 17 pages.
Kodali et al., Transcatheter Valve Repair and Replacement, Downloaded from arjournals.annualreviews.org by National Institute of Health Library on Feb. 25, 2009, 14 pages.
Kwan et al., Geometric Differences of the Mitral Apparatus Between Ischemic and Dilated Cardiomyopathy With Significant Mitral Regurgitation—Real-Time Three-Dimensional Echocardiography Study, Circulation, Mar. 4, 2003, 1135-1140.

Leung et al, Percutaneous Mitral Valve Repair—An overview of the current devices and techniques, Coronory/Cardiac Interventions—Endovascular Today, Oct. 2006, 26-33.
Levine et al., Mechanistic Insights into Functional Mitral Regurgitation, Valvular Heart Disease, 2009, 125-129.
Little et al., Three-Dimensional Ultrasound Imaging Model of Mitral Valve Regurgitation: Design and Evaluation, Ultrasound in Medicine and Biology, 2008, vol. 34, No. 4, 647-654.
Llaneras et al., Large Animal Model of Ischemic Mitral Regurgitation, The Society of Thoracic Surgeons—Ischemic Mitral Insufficiency, 1994, vol. 57, 432-439.
Magne et al., Ischemic Mitral Regurgitation: A Complex Multifaceted Disease, Cardiology, 2009, vol. 112, 244-259.
McClure et al., Early and late outcomes in minimally invasive mitral valve repair: An eleven-year experience in 707 patients, Acquired Cardiovascular Disease, The Journal of Thoracic and Cardiovascular Surgery, Jan. 2009, vol. 137, No. 1, 70-75.
Modi et al., Minimally invasive mitral valve surgery: a systematic review and meta-analysis, European Journal of Cardio-Thoracic Surgery, 2008, vol. 34, 943-952.
Myers, Jr., et al., Color Doppler Velocity Accuracy Proximal to Regurgitant Orifices: Influence of Orifice Aspect Ratio, Ultrasound in Medicine and Biology, 1999, vol. 25, No. 5, 771-792.
Ning et al., Live three-dimensional transesophageal echocardiography in mitral valve surgery, Chinese Medical Journal, 2008, vol. 121, No. 20, 2037-2041.
Nötzold et al., Microemboli in aortic valve replacement, Future Drugs Ltd, Expert Rev. Cardiovasc. Ther., vol. 4, No. 6, 2006, 853-859.
Onundarson et al., Warfarin anticoagulation intensity in specialist-based and in computer-assisted dosing practice, International Journal of Laboratory Hematology, 2008, vol. 30, 382-389.
Otsuji et al., Insights From Three-Dimensional Echocardiography Into the Mechanism of Functional Mitral Regurgitation—Direct in Vivo Demonstration of Altered Leaflet Tethering Geometry, Circulation, Sep. 16, 1997, vol. 96, No. 6, 1999-2008.
Fukuda et al., Maintenance of Geometric Alterations Associated with Percutaneous Mitral Valve Repair: Real-Time Three-Dimensional Echocardiographic Assessment in an Ovine Model, J. Heart Valve Dis, May 2008, vol. 17, No. 3, 276-282.
Pai et al., Effect of Atrial Fibrillation on the Dynamics of Mitral Annular Area, J. Heart Valve Dis., Jan. 2003, vol. 12, No. 1, 31-37.
Palacios et al., Safety and Feasibility of Acute Percutaneous Septal Sinus Shortening: First-In-Human Experience, Catheterization and Cardiovascular Interventions, 2007, vol. 69, 513-518.
Paniagua et al., First Human Case of Retrograde Transcatheter Implantation of an Aortic Valve Prosthesis, Texas Heart Institute Journal, Transcatheter Aortic Valve Prosthesis, 2005, vol. 32, No. 3, 393-398.
Rodés-Cabau et al., Feasibility and Initial Results of Percutaneous Aortic Valve Implantation Including Selection of the Transfemoral or Transapical Approach in Patients With Severe Aortic Stenosis, The American Journal of Cardiology, 2008, 1240-1246.
Satpathy et al., Delayed Defibrillator Lead Perforation: An Increasing Phenomenon, Pace, Jan. 2008, vol. 31, 10-12.
Schofer, Percutaneous MVR: Clinical Evaluation—The Carillon Experience, EuroPCR 2007, Barcelona, Spain, May 22-25, 2007, 35 pages.
Schwammenthal et al., Dynamics of Mitral Regurgitant Flow and Orifice Area—Physiologic Application of the Proximal Flow Convergence Method: Clinical Data and Experimental Testing, Circulation, Jul. 1994, vol. 90, No. 1, 307-322.
Spencer, Viacor, Inc. Announces First Patient Treated in PTOLEMY-2 Study, http://www.viacorinc.com/viacor_news.html, Nov. 14, 2008, downloaded Feb. 24, 2009, 2 pages.
Sterliński et al., Subacute cardiac perforations associated with active fixation leads, Clinical Research Leads and Lead Extraction, Europace, 2009, vol. 11, 206-212.
Turakhia et al., Rates and severity of perforation from implantable cardioverter-defibrillator leads: A 4-year study, J Intery Card Electrophysiol, 2009, vol. 24, 47-52.
Vahanian, The Cardiologist's Perspective on the Future of Percutaneous Mitral Valve Repair, Euro PCR07, 53 pages.

(56) References Cited

OTHER PUBLICATIONS

Vahanian, Coronary Sinus and Direct Annuloplasty Percutaneous Mitral Valve Repair, Innovations in Cardiovascular Interventions, Dec. 7-9, 2008, Tel-Aviv, Israel, 45 pages.
Vahanian, Edwards MONARC system—Evolution Interim Results, 31 pages.
Vahanian, Overview on Percutaneous Mitral Valve Technology, Euro PCR07, Transcatheter Valve Symposium, Barcelona, May 22-25, 2007, 29 pages.
Van Gelder et al., Diagnosis and Management of Inadvertently Placed Pacing and ICD Leads in the Left Ventricle: A Multicenter Experience and Review of the Literature, Pace, May 2000, vol. 23, 877-883.
Vranckx et al., The TandemHeart®, percutaneous transseptal left ventricular assist device: a safeguard in high-risk percutaneous coronary interventions. The six-year Rotterdam experience, Clinical research EuroInterv., 2008, vol. 4, 331-337.
Wolf et al., Solid and gaseous cerebral micorembolization after biologic and mechanical aortic valve replacement: Investigation with multirange and multifrequency transcranial Doppler ultrasound, The Journal of Thoracic and Cardiovascular Surgery, Mar. 2008, vol. 135, No. 3, 512-520.
Xiangming et al., In Vivo Characterization of Attachment Safety Between Cardiac Pacing Lead and Canine Heart Muscle*, Acta Mechanica Solida Sinica, Sep. 2007, vol. 20, No. 3, 189-197.
Yamaura et al., Geometrical Demonstration and Three-Dimensional Quantitative Analysis of the Mitral Valve With Real-Time Three-Dimensional Echocardiography: Novel Anatomical Image Creation System, J Echocardiogr, 2004, vol. 2, No. 4, 99-104.
Yosefy et al., Proximal Flow Convergence Region as Assessed by Real-time 3-Dimensional Echocardiography: Challenging the Hemispheric Assumption, Journal of the American Society of Echocardiography, Apr. 2007, Vol., No. 4, 389-396.
Bailey et al, "Surgical Repair of Mitral Insufficiency" Feb. 1951 (pp. 125-137 ).
Bailey et al, "Closed Intracardiac Tactile Surgery" Jul. 1952 (pp. 1-24).
Bailey et al., "The Surgical Correction of Mitral Insufficiency by the Use of Pericardial Grafts" Dec. 1954 (pp. 551-627).
Benichoux et al., "A Method of Surgical Correction of Mitral Insufficiency" 1955 (pp. 148-158).
Blalock, "A Consideration of Some of the Problems in Cardiovascular Surgery" Jun. 1951 (pp. 543-571).
Borrie, "Mitral Insufficiency: Experimental Circular Suture Around the Artioventricular Ring" 1955 (pp. 687-697).
Carter et al. "Surgical Treatment of Mitral Insufficiency" 1953 (pp. 574-583).
European Search Report dated Jul. 12, 1984 cited in EP0125393.
"French catheter scale chart" http://en.wikipedia.org/wiki/French_catheter_scale_chart, Dec. 20, 2006, 1 page.
"General Physical Properties of PVA Sponge (values are not guaranteed)", Ceiba Technologies, http://www.ceibatech.com/PVASpongeDate.htm, Dec. 20, 2006 3 pages.
Glenn et al., "The Implantation of a Vascularized Graft in the Chambers of the Heart" 1954 (pp. 5-11).
Glenn et al, "The Surgical Treatment of Mitral Insufficiency: the Fate of Vascularized Transchamber Intracardiac Graft" Apr. 1955 (pp. 510-518).
Glenn et al., "The Surgical Treatment of Mitral Insufficiency with Particular Reference to the Application of a Vertically Suspended Graft" Jul. 1956 (pp. 59-77).
Glover, et al., "The Fate of Intracardiac Pericardial Grafts as Applied to the Closure of Septal Defects and to the Relief of Mitral Insufficiency" 1952 (pp. 178-185).
Harken et al., "The Surgical Correction of Mitral Insufficienty" Surgical Forum 1954 (pp. 4-7).
Harken et al, "The Surgical Correction of Mitral Insufficienty" The Journal of Thoracic Surgery 1954 (pp. 604-627).
Henderson et al., "The Surgical Treatment of Mitral Insufficiency" Jun. 1953 (pp. 858-868).
International Search and Written Opinion mailed May 11, 2007 filed in corresponding PCT patent application PCT/US06/39011(8 pages).
Johns et al., Mitral Insufficiency: the Experimental Use of a Mobile Polyvinyl sponge Prosthesis: Sep. 1954 (pp. 335-341).
Moore, et al., "Unsuitability of Transventricular Autogenous Slings for Diminishing Valvular Insufficiency" Feb. 1953 (pp. 173-182).
"PVA Datasheet", www.sponge-pva.com/data.htm, Dec. 20, 2006, 2 pages.
"PVA Sponge W (wet) & D (dry)", Ceiba Technologies, http://www.ceibatech.com/PVASpongeW&D.htm, Dec. 20, 2007 5 pages.
Sakakibara, "A Surgical Approach to the Correction of Mitral Insufficiency" Aug. 1955 (pp. 196-203).
SPI-Chem™ Vinylec® (Formvar®) Resins, http://www.2spi.com/catalog/submat/formvar-resins.shtml, Dec. 20, 2006, 5 pages.
Trippel et al, "Reinforced Ivalon Sponge as an Aortic Prosthesis*", Annals of Surgery, Feb. 1960, vol. 151, No. 2, pp. 216-224.
"Vinylec® Resins", http://www.2spi.com/catalog/submat/vinylec-physical.html, Dec. 20, 2006, 1 page.
Matthews, Anatomy of the Heart, Definitions Cardiology Explained and Presented by Robert Matthews, MD, http://www.rjmatthewsmd.com/Definitions/anatomy_ofthe_heart.htm, printed Jul. 28, 2008, 265 pages.
Mullens, Vascular access, Cardiac Catheterization in Congenital Heart Disease; Pediatric and Adult, 2006, Chapter 4, pp. 115-117, 5 pages, Blackwell Futura, USA.
Mullens, Aortic valve dilation, Cardiac Catheterization in Congenital Heart Disease; Pediatric and Adult, 2006, Chapter 19, pp. 487-489, 5 pages, Blackwell Futura, USA.
Mullens, Foreign body removal, Cardiac Catheterization in Congenital Heart Disease; Pediatric and Adult, 2006, Chapter 12, pp. 350-377, 30 pages, Blackwell Futura, USA.
Mullens, Flow directed catheters ("floating" balloon catheters), Cardiac Catheterization in Congenital Heart Disease; Pediatric and Adult, 2006, Chapter 7, pp. 213-221, 9 pages, Blackwell Futura, USA.
Acar et al, AREVA: Multicenter Randomized Comparison of Low-Dose Versus Standard-Dose Anticoagulation in Patients With Mechanical Prosthetic Heart Valves, Circulation, Nov. 1, 1996, 2107-12, vol. 94, No. 9.
Acker et al., Mitral valve surgery in heart failure: Insights from the Acorn Clinical Trial, Surgery for Acquired Cardiovascular Disease, The Journal of Thoracic and Cardiovascular Surgery, Sep. 2006, 568-577.e4, vol. 132, No. 3.
Babaliaros et al, Emerging Applications for Transseptal Left Heart Catheterization—Old Techniques for New Procedures, Journal of the American College of Cardiology, Jun. 3, 2008, 2116-22, vol. 51, No. 22.
Kuck et al, Best of Structural Heart Disease Abstracts, TCT-124, The American Journal of Cardiology, Oct. 20-25, 2007, 58L.
Rinaldi et al., Best of Structural Heart Disease Abstracts, TCT-123, The American Journal of Cardiology, Oct. 20-25, 2007, 57L.
Siminiak et al., Best of Structural Heart Disease Abstracts, TCT-125, The American Journal of Cardiology, Oct. 20-25, 2007, 58L.
B-Lundqvist et al., Transseptal Left Heart Catheterization: A Review of 278 Studies, Clin. Cardiol., Jan. 1986, 21-26, vol. 9.
Bono et al., ACC/AHA 2006 Guidelines for the Management of Patients With Valvular Heart Disease: Executive Summary, Circulation—Journal of the American Heart Association, Downloaded from circ.ahajournals.org, Jul. 31, 2008, 449-527.
Braunberger et al., Very Long-Term Results (More Than 20 Years) of Valve Repair With Carpentier's Techniques in Nonrheumatic Mitral Valve Insufficiency, Downloaded from circ.ahajournals.org, Aug. 26, 2008, I-8-I-11.
Bryan et al., Prospective randomized comparison of CarboMedics and St. Jude Medical bileaflet mechanical heart valve prostheses: Ten-year follow-up, The Journal of Thoracic and Cardiovascular Surgery, Mar. 2007, 614-622.e2, vol. 133, No. 3.
Burkhoff et al., A randomized multicenter clinical study to evaluate the safety and efficacy of the TandemHeart percutaneous ventricular assist device versus conventional therapy with intraaortic balloon pumping for treatment of cardiogenic shock, American Heart Journal, Sep. 2006, 469.e1-469.e8, vol. 152, No. 3.

(56) References Cited

OTHER PUBLICATIONS

Byrne et al., Percutaneous Mitral Annular Reduction Provides Continued Benefit in an Ovine Model of Dilated Cardiomyopathy, Downloaded from circ.ahajournals.org, Aug. 26, 2008, 3088-92.
Carpentier et al., Reconstructive surgery of mitral valve incompetence Ten-year appraisal, The Journal of Thoracic and Cardiovascular Surgery, Mar. 1980, 338-348, vol. 79, No. 3.
Casselman et al., Mitral Valve Surgery Can Now Routinely Be Performed Endoscopically, Downloaded from circ.ahajournals.org, Aug. 26, 2008, II-48-II-54.
Cauchemez et al., High-Flow Perfusion of Sheaths for Prevention of Thromboembolic Complications During Complex Catheter Ablation in the Left Atrium, Journal of Cardiovascular Electrophysiology, Mar. 2004, 276-283, vol. 15, No. 3.
ClinicalTrials.gov, Aachen Safety and Efficacy of the Percutaneous Transvenous Mitral Annuloplasty Device to Reduce Mitral Regurgitation (PTOLEMY), http://clinicaltrials.gov/ct2/show/NCT00572091?term=mitral+regurgitation&rank=2, Aug. 25, 2008, 1-3.
ClinicalTrials.gov, Feasibility Study of a Percutaneous Mitral Valve Repair System., http://clinicaltrials.gov/ct2/show/NCT00209339?term=mitral+valve&rank=3, Aug. 25, 2008, 1-4.
ClinicalTrials.gov, Montreal Safety and Efficacy of the Percutaneous Transvenous Mitral Annuloplasty Device (PTOLEMY), http://clinicaltrials.gov/ct2/show/NCT00571610?term=mitral+regurgitation&rank=13, Aug. 25, 2008, 1-4.
ClinicalTrials.gov, Pivotal Study of a Percutaneous Mitral Valve Repair System, http://clinicaltrials.gov/ct2/show/NCT00209274?term=mitral+valve&rank=1, Aug. 25, 2008, 1-4.
ClinicalTrials.gov, RESTOR-MV: Randomized Evaluation of a Surgical Treatment for Off-Pump Repair of the Mitral Valve, http://clinicaltrials.gov/ct2/show/NCT00120276?term=myocor&rank=1, Aug. 25, 2008, 1-5.
ClinicalTrials.gov, Safety and Efficacy of the Percutaneous Transvenous Mitral Annuloplasty Device to Reduce Mitral Regurgitation (PTOLEMY), http://clinicaltrials.gov/ct2/show/NCT00568230?term=mitral+valve&rank=53, Aug. 25, 2008, 1-3.
ClinicalTrials.gov, VIVID—Valvular and Ventricular Improvement Via iCoapsys Delivery—Feasibility Study, http://clinicaltrials.gov/ct2/show/NCT00512005?term=mitral+valve&rank=12, Aug. 25, 2008, 1-4.
Crabtree et al., Recurrent Mitral Regurgitation and Risk Factors for Early and Late Mortality After Mitral Valve Repair for Functional Ischemic Mitral Regurgitation, The Society of Thoracic Surgeons, 2008, 1537-43, 85.
Criber et al., Early Experience With Percutaneous Transcatheter Implantation of Heart Valve Prosthesis for the Treatment of End-Stage Inoperable Patients With Calcific Aortic Stenosis, Journal of the American College of Cardiology, Feb. 18, 2004, 698-703, vol. 43, No. 4.
De Bonis et al., Similar long-term results of mitral valve repair for anterior compared with posterior leaflet prolapse, The Journal of Thoracic and Cardiovascular Surgery, Feb. 2006, 364-370, vol. 131, No. 2.
Deloche et al., Valve repair with Carpentier techniques the second decade, The Journal of Thoracic and Cardiovascular Surgery, Jun. 1990, 990-1002, vol. 99, No. 6.
De Simone et al., A clinical study of annular geometry and dynamics in patients with ischemic mitral regurgitation: new insights into asymmetrical ring annuloplasty, European Journal of Cardio-thoracic Surgery, 2006, 355-361, 29.
Detaint et al., Surgical Correction of Mitral Regurgitation in the Elderly—Outcomes and Recent Improvements, Downloaded from circ.ahajournals.org, Aug. 26, 2008, 265-272.
Dubreuil et al., Percutaneous Mitral Valve Annuloplasty for Ischemic Mitral Regurgitation: First in Man Experience With a Tempory Implant, Catheterization and Cardiovascular Interventions, 2007, 1053-61, 69.
Duffy et al., Feasibility and Short-Term Efficacy of Percutaneous Mitral Annular Reduction for the Therapy of Funcitonal Mitral Regurgitation in Patients With Heart Failure, Catheterization and Cardiovascular Interventions, 2006, 205-210, 68.
Epstein et al, Gross and Microscopic Pathological Changes Associated With Nonthoracotomy Implantable Defibrillator Leads, Downloaded from circ.ahajournals.org, Jul. 23, 2008, 1517-24.
Epstein et al, Embolic Complications Associated With Radiofrequency Catheter Ablation, The American Journal of Cardiology, Mar. 15, 1996, 655-658, vol. 77.
Fagundes et al., Safety of Single Transseptal Puncture for Ablation of Atrial Fibrillation: Retrospective Study from a Large Cohort of Patients, Journal of Cardiovascular Electrophysiology, Dec. 2007, 1277-81, vol. 18, No. 12.
Feldman et al., Patient selection for percutaneous mitral valve repair: insight from early clinical trial applications, Nature Clinical Practice Cardiovascular Medicine, Feb. 2008, 84-90, vol. 5, No. 2.
Feldman et al., Percutaneous Mitral Valve Repair Using the Edge-to-Edge Technique—Six-Month Results of the Everest Phase I Clinical Trial, Journal of the American College of Cardiology, Dec. 6, 2005, 2134-40, vol. 46, No. 11.
Fernandez et al., Early and late-phase events after valve replacement with the St. Jude Medical prosthesis in 1200 patients,The Journal of Thoracic and Cardiovascular Surgery, Feb. 1994, 394-407, vol. 107, No. 2.
Gillinov et al., Durability of Mitral Valve Repair for Degenerative Disease, The Journal of Thoracic and Cardiovascular Surgery, Nov. 1998, 734-743, vol. 116, No. 5.
Grossi et al., Intraoperative Effects of the Coapsys Annuloplasty System in a Randomized Evaluation (RESTOR-MV) of Functional Ischemic Mitral Regurgitation, The Society of Thoracic Surgeons, 2005, 1706-11, 80.
Grossi et al., Late Results of Mitral Valve Reconstruction in the Elderly, The Society of Thoracic Surgeons, 2000, 1224-6, 70.
Grossi et al., Minimally Invasive Mitral Valve Surgery: A 6-Year Experience With 714 Patients, The Society of Thoracic Surgeons, 2002, 660-4, 74.
Hendren et al., Mitral Valve Repair for Ischemic Mitral Insufficiency, The Society of Thoracic Surgeons, 1991, 1246-52, 52.
Heupler et al., Infection Prevention Guidelines for Cardiac Catheterization Laboratories, Catheterization and Cardiovascular Diagnosis, 1992, 260-263, 25.
Hvass et al., Papillary Muscle Sling: A New Functional Approach to Mitral Repair in Patients With Ischemic Left Ventricular Dysfunction and Functional Mitral Regurgitation, The Society of Thoracic Surgeons, 2003, 809-11, 75.
Ibrahim et al., The St. Jude Medical prosthesis—A thirteen-year experience, The Journal of Thoracic and Cardiovascular Surgery, Aug. 1994, 221-230, vol. 108, No. 2.
Iskandar et al., Tricuspid Valve Malfunction and Ventricular Pacemaker Lead: Case Report and Review of the Literature, Echocardiography: A Jrnl of CV Ultrasound & Allied Tech., 2006, 692-697, vol. 23, No. 8.
Kasegawa et al., Mitral Valve Repair for Anterior Leaflet Prolapse With Expanded Polytetrafluoroethylene Sutures, The Society of Thoracic Surgeons, 2006, 1625-31, 81.
Kaye et al., Feasibility and Short-Term Efficacy of Percutaneous Mitral Annular Reduction for the Therapy of Heart Failure-Induced Mitral Regurgitation, Downloaded from circ.ahajournals.org, Aug. 26, 2008, 1795-97.
International Search Report and Written Opinion dated Sep. 22, 2008 issued in PCT Application No. PCT/US08/63560, 11 pages.
International Search Report and Written Opinion dated Sep. 29, 2008 issued in PCT Application No. PCT/US08/63568, 12 pages.
Kerensky, Complications of Cardiac Catheterization and Strategies to Reduce Risks, Diagnostic and Therapeutic Cardiac Catheterization, 1998, Chapter 8, 91-105.
Koertke et al., INR Self-Management Permits Lower Anticoagulation Levels After Mechanical Heart Valve Replacement, downloaded from circ.ahajournals.org, Aug. 26, 2008, II-75-II-78.
Kratz et al., St. Jude Prosthesis for Aortic and Mitral Valve Replacement: A Ten-Year Experience, The Society of Thoracic Surgeons, 1993, 462-8, 56.

(56) References Cited

OTHER PUBLICATIONS

Kron et al., Surgical Relocation of the Posterior Papillary Muscle in Chronic Ischemic Mitral Regurgitation, The Society of Thoracic Surgeons, 2002, 600-1, 74.

Kuwahara et al., Mechanism of Recurrent/Persistent Ischemic/Functional Mitral Regurgitation in the Chronic Phase After Surgical Annuloplasty—Importance of Augmented Posterior Leaflet Tethering, Circulation, Jul. 4, 2006, I-529-I-534.

Laskey et al., Multivariable Model for Prediction of Risk of Significant Complication During Diagnostic Cardiac Catheterization, Catheterization and Cardiovascular Diagnosis, 1993, 185-190, 30.

Lee et al., Mitral Valve Reconstruction: Experience Related to Early and Late Mortality and Reoperation, J Heart Valve Dis, Nov. 2005, 715-721, vol. 14, No. 6.

Liddicoat et al., Percutaneous Mitral Valve Repair: A Feasibility Study in an Ovine Model of Acute Ischemic Mitral Regurgitation, Catheterization and Cardiovascular Interventions, 2003, 410-416, 60.

Lim et al., Percutaneous Transthoracic Ventricular Puncture for Diagnostic and Interventional Catheterization, Catheterization and Cardiovascular Interventions, 2008, 915-918, 71.

Lin et al., Severe Symptomatic Tricuspid Valve Regurgitation Due to Permanent Pacemaker or Implantable Cardioverter-Defibrillator Leads, Journal of the American College of Cardiology, May 17, 2005, 1672-5, vol. 45, No. 10.

Lozonschi et al., Transapical Mitral Valved Stent Implantation, The Society of Thoracic Surgeons, 2008, 745-8, 86.

Mack, Percutaneous Therapies for Mitral Regurgitation: Where Do We Stand and Where Are We Going? Do Current Devices Really Represent a Step Forward Compared to Surgery?, 2007 Heart Valve Summit, Jun. 7, 2007, 59 pages.

Maleki et al., Intracardiac Ultrasound Detection of Thrombus on Transseptal Sheath: Incidence, Treatment, and Prevention, Journal of Cardiovascular Electrophysiology, Jun. 2005, 561-565, vol. 16, No. 6.

Maniu et al., Acute and Chronic Reduction of Functional Mitral Regurgitation in Experimental Heart Failure by Percutaneous Mitral Annuloplasty, Journal of the American College of Cardiology, Oct. 19, 2004, 1652-61, vol. 44, No. 8.

McGee et al., Recurrent mitral regurgitation after annuloplasty for functional ischemic mitral regurgitation, Surgery for Acquired Cardiovascular Disease, The Journal of Thoracic and Cardiovascular Surgery, Dec. 2004, 916-924.e4, vol. 128, No. 6.

Mehra et al., Surgery for Severe Mitral Regurgitation and Left Ventricular Failure: What Do We Really Know?, Journal of Cardiac Failure, Mar. 2008, 145-150. vol. 14, No. 2.

Menicanti et al., Functional Ischemic Mitral Regurgitation in Anterior Ventricular Remodeling: Results of Surgical Ventricular Restoration with and Without Mitral Repair, Heart Failure Reviews, 2004, 317-327, 9.

Messas et al., Efficacy of Chordal Cutting to Relieve Chronic Persistent Ischemic Mitral Regurgitation, Circulation, Sep. 9, 2003, II-111-II-115.

Meurin et al., Thromboembolic events early after mitral valve repair: Incidence and predictive factors, International Journal of Cardiology, 2008, 45-52, 126.

Mirable et al., What are the characteristics of patients with severe, symptomatic, mitral regurgitation who are denied surgery?, The European Society of Cardiology, 2007, 1358-65, 28.

Mitchell et al., Complications, Cardiac catheterization and coronary intervention, Chapter 9, 2008, 238-270.

Mishra et al., Coapsys Mitral Annuloplasty for Chronic Functional Ischemic Mitral Regurgitation: 1-Year Results, The Society of Thoracic Surgeons, 2006, 42-46, 81.

Morgan et al., Left Heart Catheterization by Direct Ventricular Puncture: Withstanding the Test of Time, Catheterization and Cardiovascular Diagnosis, 1989, 87-90, 16.

Murday et al., A Prospective Controlled Trial of St. Jude Versus Starr Edwards Aortic and Mitral Valve Prostheses, The Society of Thoracic Surgeons, 2003, 66-74, 76.

Nifong et al., Robotic mitral valve surgery: A United States multicenter trial, The Journal of Thoracic and Cardiovascular Surgery, Jun. 2005, 1395-1404, vol. 129, No. 6.

Noto et al., Cardiac Catheterization 1990: A Report of the Registry of the Society for Cardiac Angiography and Interventions (SCA&I), Catheterization and Cardiovascular Diagnosis, 1991, 75-83, 24.

Ohlow et al., Incidence and outcome of femoral vascular complications among 18, 165 patients undergoing cardiac catheterisation, International Journal of Cardiology, 2008, 1-6.

Piazza et al., Transcatheter Mitral Valve Repair for Functional Mitral Regurgitation: Coronary Sinus Approach, Journal of Interventional Cardiology, 2007, 495-508, vol. 20, No. 6.

Pedersen et al., iCoapsys Mitral Valve Repair System: Percutaneous Implantation in an Animal Model, Catheterization and Cardiovascular Interventions, 2008, 125-131, 72.

Prifti et al., Ischemic Mitral Valve Regurgitation Grade II-III: Correction in Patients with Impaired Left Ventricular Function undergoing Simultaneous Coronary Revascularization, J Heart Valve Dis, Nov. 2001, 754-762, vol. 10, No. 6.

Richardson et al., Is a port-access mitral valve repair superior to the sternotomy approach in accelerating postoperative recovery?, Interactive CardioVascular and Thoracic Surgery, Downloaded from icvts.ctsnetjournals.org, Aug. 26, 2008, 670-683, 7.

Ruiz, New Percutaneous Approaches for Mitral Regurgitation, Lenox Hill Heart and Vascular Institute of New York, May 13-16, 2008, 26 pages.

Rumel et al., Section on Cardiovascular Diseases—The Correction of Mitral Insufficiency With a Trans-Valvular Polyvinyl Formalinized Plastic (Ivalon) Sponge Prosthesis, American College of Chest Physicians, Apr. 1958, Downloaded from chestjournal.org, Jul. 23, 2008, 401-413.

Seeburger et al, Minimal invasive mitral valve repair for mitral regurgitation: results of 1339 consecutive patients, European Journal of Cardio-thoracic Surgery, 2008, 1-6.

Southard et al., Current Catheter-Based Treatments of Functional Mitral Regurgitation, Cardiac Interventions Today, Jun. 2007, 41-44.

Svensson et al., United States Feasibility Study of Transcatheter Insertion of a Stented Aortic Valve by the Left Ventricular Apex, The Society of Thoracic Surgeons, 2008, 46-55, 86.

Toledano et al., Mitral regurgitation: Determinants for referral for cardiac surgery by Canadian cardiologists, Can J. Cardiol, Mar. 1, 2007, 209-214, vol. 23, No. 3.

Tops et al., Percutaneous Valve Procedures: An Update, Curr Probl Cardiol, Aug. 2008, 417-426.

Walther et al., Transapical minimally invasive aortic valve implantation; the initial 50 patients, European Journal of Cardio-thoracic Surgery, 2008, 983-988, 33.

Webb et al., Percutaneous Mitral Annuloplasty With the MONARC System: Preliminary Results From the Evolution Trial, TCT-103, The American Journal of Cardiology, Oct. 22-27, 2006, 49M.

Webb et al., Percutaneous Transvenous Mitral Annuloplasty—Initial Human Experience with Device Implantation in the Coronary Sinus, downloaded from circ.ahajournals.org, Aug. 26, 2008, 851-855.

Webster et al., Impact of transvenous ventricular pacing leads on tricuspid regurgitation in pediatric and congenital heart disease patients, J Intery Card Electrophysiol, 2008, 65-68, 21.

Ye et al., Six-month outcome of transapical transcatheter aortic valve implantation in the initial seven patients, European Journal of Cardio-thoracic Surgery, 2007, 16-21, 31.

Yoshida, et al., Assessment of Left-to-Right Atrial Shunting After Percutaneous Mitral Valvuloplasty by Transesophageal Color Doppler Flow-Mapping, Circulation, Dec. 1989, 1521-1526, vol. 80, No. 6.

Zhou et al., Thromboembolic Complications of Cardiac Radiofrequency Catheter Ablation: A Review of the Reported Incidence, Pathogenesis and Current Research Directions, Journal of Cardiovascular Electrophysiology, Apr. 1999, 611-620, vol. 10, No. 4.

U.S. Office Action dated Dec. 15, 2009 issued in U.S. Appl. No. 11/258,828, 12 pages.

U.S. Office Action dated Jan. 8, 2010 issued in U.S. Appl. No. 11/748,147, 63 pages.

(56) References Cited

OTHER PUBLICATIONS

U.S. Office Action dated Jan. 14, 2010 issued in U.S. Appl. No. 11/940,674, 59 pages.
U.S. Office Action dated Jan. 25, 2010 issued in U.S. Appl. No. 11/748,121, 9 pages.
U.S. Office Action dated Feb. 4, 2010 issued in U.S. Appl. No. 11/748,138, 58 pages.
U.S. Office Action dated Jul. 8, 2009 issued in U.S. Appl. No. 11/258,828, 7 pages.
International Search Report and Written Opinion dated Aug. 11, 2009 issued in PCT Application No. PCT/US2009/046995, 11 pages.
U.S. Office Action dated Sep. 19, 2012, issued in U.S. Appl. No. 12/510,929, 10 pages.
U.S. Office Action dated Oct. 9, 2012, issued in U.S. Appl. No. 12/872,228, 7 pages.
U.S. Notice of Allowance dated Nov. 21, 2012, issued in U.S. Appl. No. 11/748,121, 8 pages.
U.S. Office Action dated Jun. 20, 2012 issued in U.S. Appl. No. 11/940,694, 9 pages.
U.S. Office Action dated Jun. 21, 2012 issued in U.S. Appl. No. 11/748,147, 29 pages.
Notice of Allowance dated Jul. 20, 2012 issued in U.S. Appl. No. 11/748,121, 10 pages.
International Search Report and Written Opinion dated Jul. 6, 2010 issued in PCT Patent Application No. PCT/US2010/032764, 9 pages.
U.S. Office Action dated Aug. 30, 2010 issued in U.S. Appl. No. 11/748,138, 9 pages.
U.S. Office Action dated Aug. 31, 2010 issued in U.S. Appl. No. 11/748,121, 11 pages.
International Search Report and Written Opinion dated Sep. 21, 2010 issued in PCT Patent Application No. PCT/US2010/043360, 9 pages.
European Intent to Grant dated Feb. 22, 2013 issued in European Patent Application No. 08 755 418.4, 7 pages.
European Search Report dated Mar. 6, 2013 issued in European Patent Application No. 10804952.9, 8 pages.
Notice of Allowance dated Mar. 8, 2013 issued in U.S. Appl. No. 11/748,138, 9 pages.
Final Office Action dated Mar. 13, 2013 issued in U.S. Appl. No. 11/748,147, 10 pages.
Final Office Action dated Mar. 22, 2013 issued in U.S. Appl. No. 12/510,929, 13 pages.
Notice of Allowance dated Apr. 11, 2013 issued in U.S. Appl. No. 13/545,927, 12 pages.
Supplemental Notice of Allowability dated May 2, 2013 issued in U.S. Appl. No. 13/545,927, 5 pages.
Notice of Allowance dated Oct. 24, 2013 issued in U.S. Appl. No. 11/748,147, 12 pages.
Office Action dated Nov. 1, 2013 issued in U.S. Appl. No. 13/347,522, 6 pages.
European Office Action dated Nov. 7, 2013 issued in European Patent Application No. 10 804 952.9, 5 pages.
Notice of Allowance dated Jun. 3, 2013 issued in U.S. Appl. No. 12/872,228, 7 pages.
Final Office Action dated Jun. 19, 2013 issued in U.S. Appl. No. 11/748,147, 10 pages.
Notice of Allowance dated Jul. 8, 2013 issued in Canadian Patent Application No. 2,627,517, 1 page.
Notice of Allowance dated Aug. 1, 2013 issued in U.S. Appl. No. 12/510,929, 10 pages.
Notice of Allowance dated Aug. 12, 2013 issued in U.S. Appl. No. 11/940,724, 26 pages.
Notice of Allowance dated Oct. 31, 2011 issued in U.S. Appl. No. 11/258,828, 10 pages.
Preliminary Report on Patentability dated Nov. 1, 2011 issued in PCT Patent Application No. PCT/US2010/032764, 4 pages.
U.S. Office Action dated Nov. 3, 2011 issued in U.S. Appl. No. 12/872,228, 8 pages.
Notice of Allowance dated Dec. 14, 2011 issued in U.S. Appl. No. 12/431,399, 12 pages.
U.S. Office Action dated Dec. 21, 2011, issued in U.S. Appl. No. 11/748,121, 9 pages.
U.S. Office Action dated Jan. 18, 2012 issued in U.S. Appl. No. 11/940,724, 10 pages.
International Preliminary Report on Patentability dated Jan. 31, 2012 issued in PCT Patent Application No. PCT/US2010/043360, 7 pages.
U.S. Office Action dated Feb. 15, 2012 issued in U.S. Appl. No. 11/940,694, 9 pages.
U.S. Notice of Allowance dated Mar. 8, 2012 issued in U.S. Appl. No. 12/872,228, 7 pages.
Extended European search report dated Nov. 30, 2010 issued in European Patent Application No. 08850467.5, 6 pages.
Extended European search report dated Nov. 30, 2010 issued in European Patent Application No. 08755418.4, 7 pages.
Extended European search report dated Nov. 30, 2010 issued in European Patent Application No. 08849442.2, 6 pages.
Extended European Search Report dated Dec. 1, 2010 issued in European Patent Application No. 08755426.7, 6 pages.
Extended European Search Report dated Dec. 14, 2010 issued in European Patent Application No. 06816336.9, 7 pages.
U.S. Office Action dated Mar. 21, 2011 issued in U.S. Appl. No. 11/258,828, 22 pages.
U.S. Office Action dated Mar. 29, 2011 issued in U.S. Appl. No. 11/748,121, 14 pages.
U.S. Office Action dated Apr. 4, 2011 issued in U.S. Appl. No. 11/940,724, 65 pages.
European Examination Report dated Aug. 4, 2011 issued in European Patent No. 06 816 336.9, 3 pages.
U.S. Office Action dated Aug. 29, 2011 issued in U.S. Appl. No. 11/940,694, 11 pages.
European Examination Report dated Aug. 11, 2011 issued in European Patent No. 08 755 418.4, 3 pages.
Canadian Office Action dated Sep. 18, 2012 issued in Canadian Patent Application No. 2,627,517, 2 pages.
Intent to Grant dated Jan. 2, 2013 issued in European Patent Application No. 06816336.9, 7 pages.
Notice of Allowance dated Jan. 9, 2013 issued in U.S. Appl. No. 11/748,121, 7 pages.
U.S. Office Action dated Jun. 28, 2010 issued in U.S. Appl. No. 11/258,828, 14 pages.
Notice of Allowance dated Jul. 1, 2010 issued in U.S. Appl. No. 11/940,674, 6 pages.
U.S. Office Action dated Jul. 20, 2010 issued in U.S. Appl. No. 11/748,147, 15 pages.
Ryhänen et al., In vivo biocompatibility evaluation of nickel-titanium shape memory metal alloy: Muscle and perineural tissue responses and encapsule membrane thickness, Muscle and Perineural Tissue Response to Nitinol, Jan. 19, 1998, pp. 481-488.
International Preliminary Report on Patentability dated May 27, 2010 issued in PCT/US2008/083574, 4 pages.
International Preliminary Report on Patentability and Written Opinion, issued in PCT/US2008/063560, dated Nov. 26, 2009, 8 pages.
International Preliminary Report on Patentability and Written Opinion issued in PCT/US2008/083570, dated May 27, 2010, 4 pages.

* cited by examiner

Transseptal catheter in the Right Atrium

Guidewire Advanced into the SVC

Catheter Advanced into the SVC

Catheter Tip pulled back to the Fossa Ovalis

Fossa Ovalis Tented by tip of catheter

Fossa Ovalis Punctured by tip of Needle

Fossa Ovalis Punctured by tip of Catheter

Needle withdrawn

Guidewire placed in RA

Dilator Removed - Leaving 0.018" Stiff Guidewire in LA

Snare catheter placed, guidewire in right atrium

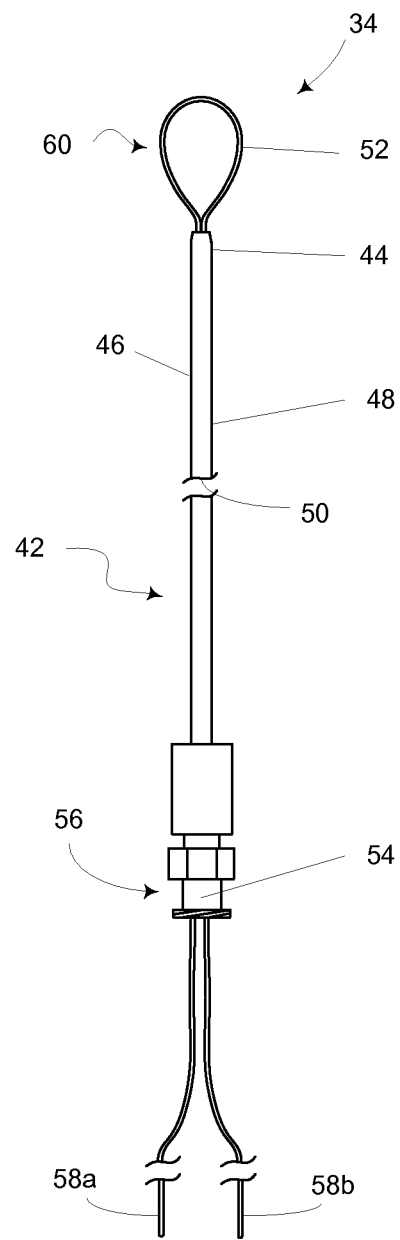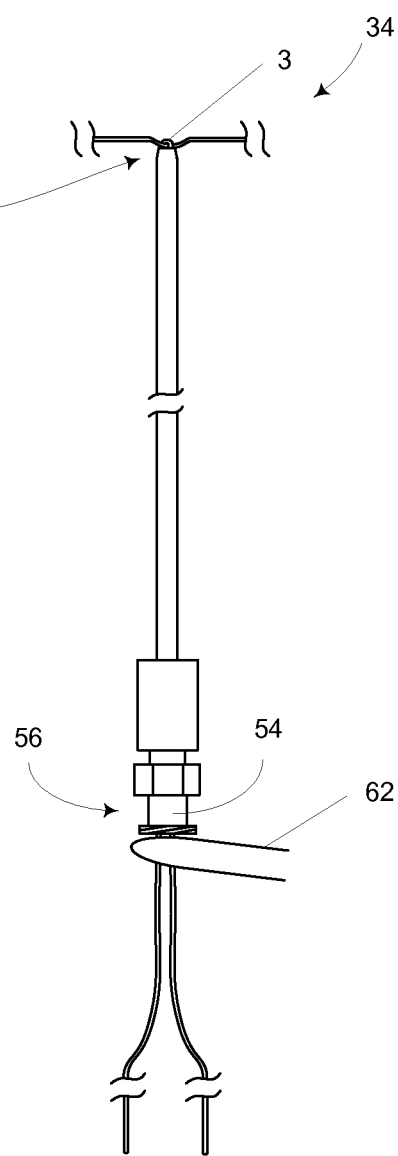
Figure 12A
Snare Catheter - Loop Open
Figure 12B
Snare Catheter - Loop Tightened Balloon in the Left Atrium with guidewire retracted to mid-balloon

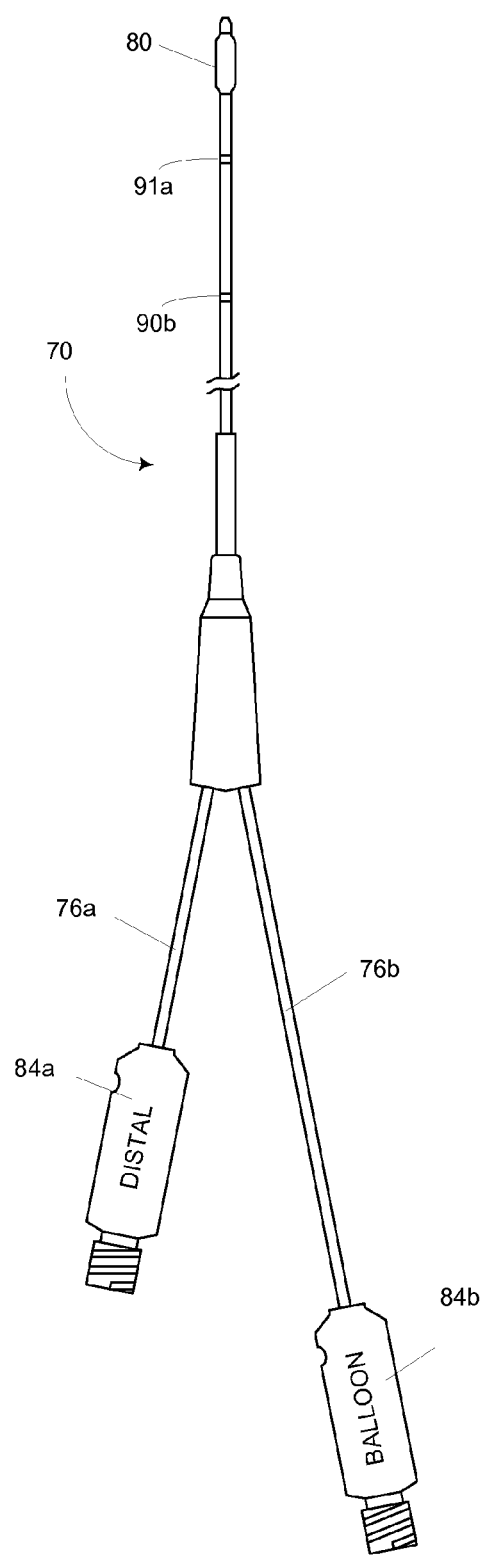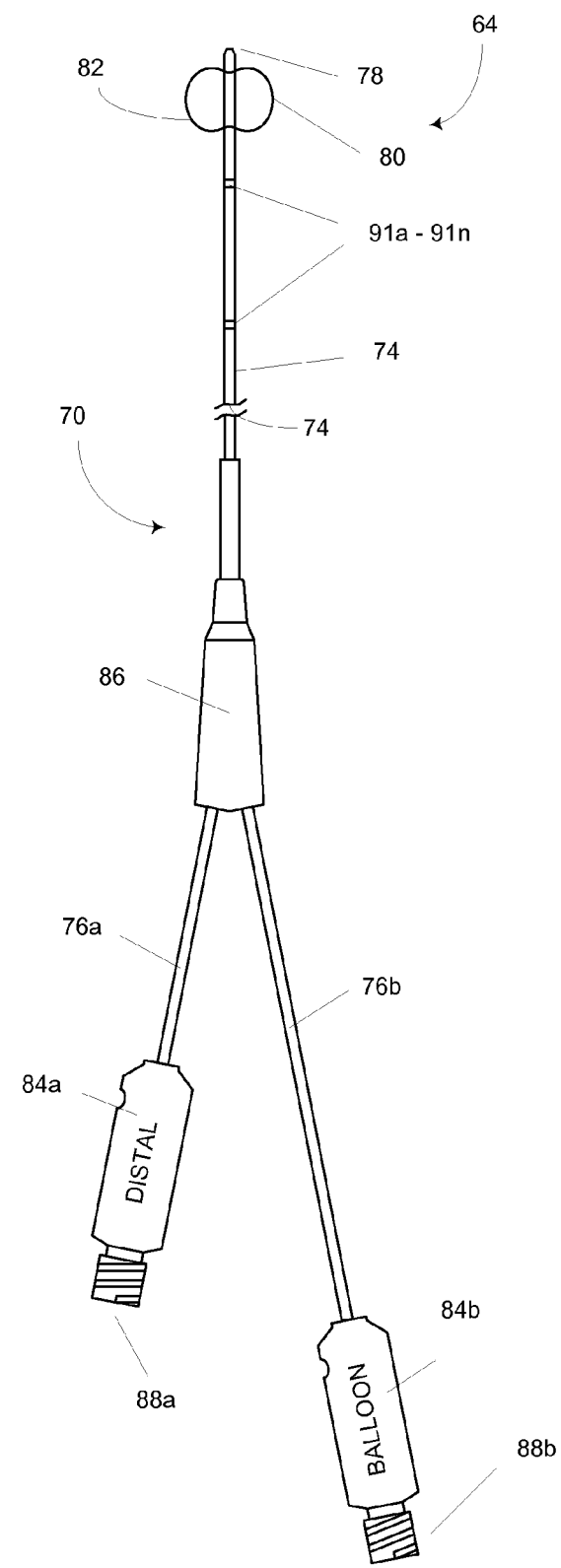
Figure 14A
Balloon Catheter - Balloon Deflated
Figure 14B
Balloon Catheter - Balloon Inflated Balloon in the Left Ventricle after passing through the mitral valve Balloon passing into the LV through the gap between two papillary muscles, chordae of the mitral valve, and ventricular wall Section through the upper chambers, looking down on the atria, showing the orientation of the mitral valve cusps Balloon in apex with guidewire retracted to mid-balloon Balloon in apex with guidewire through the snare loop Guidewire snared in LV apex Balloon pulled back into the right atrium along the guidewire Steerable cather with dilator advanced to LV apex over guidewire Steerable cather without dilator advanced to LV apex over guidewire Implant advanced through the steerable to the LV apex Implant deployed by removal of the steerable Snare catheter and guidewire removed Dilator for Steerable Delivery Catheter Dilator for Steerable Delivery Catheter - with three regions of varying stiffness

OUTSIDE VIEW OF IMPLANT

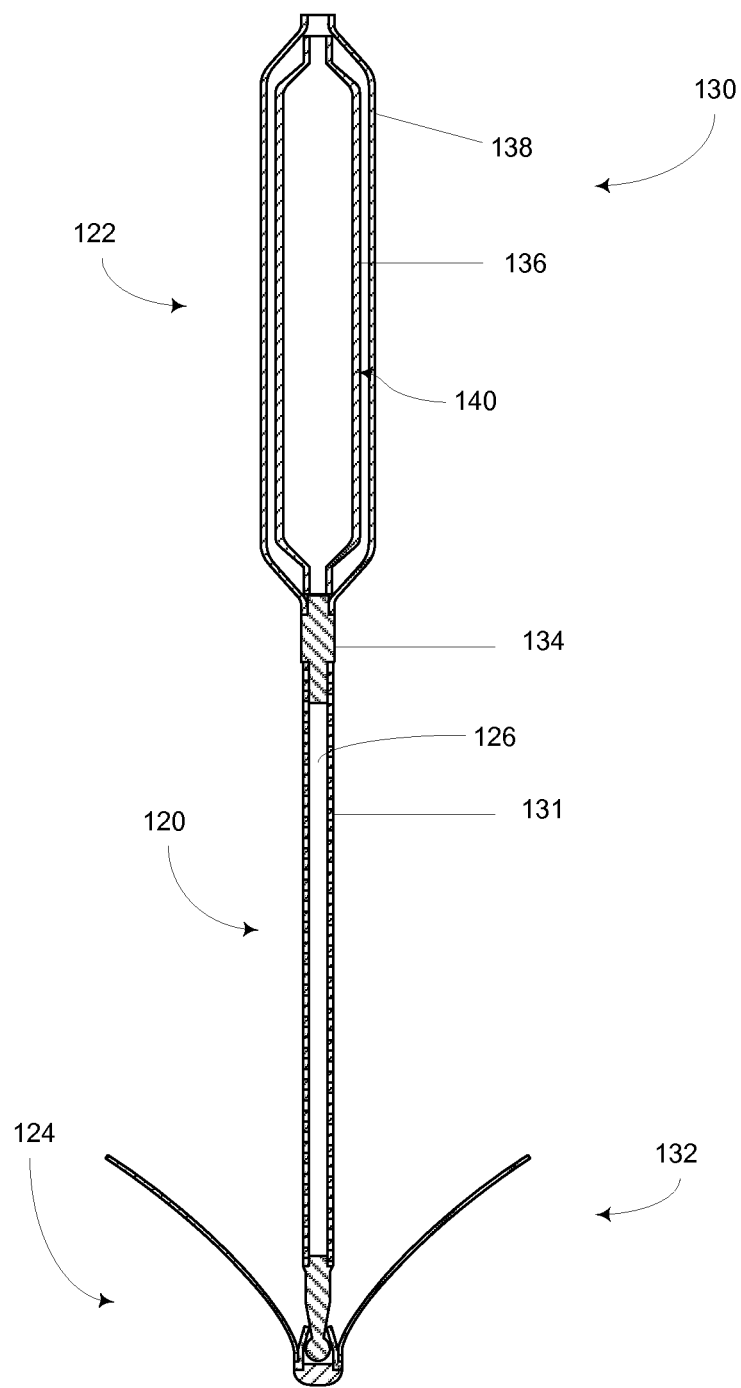

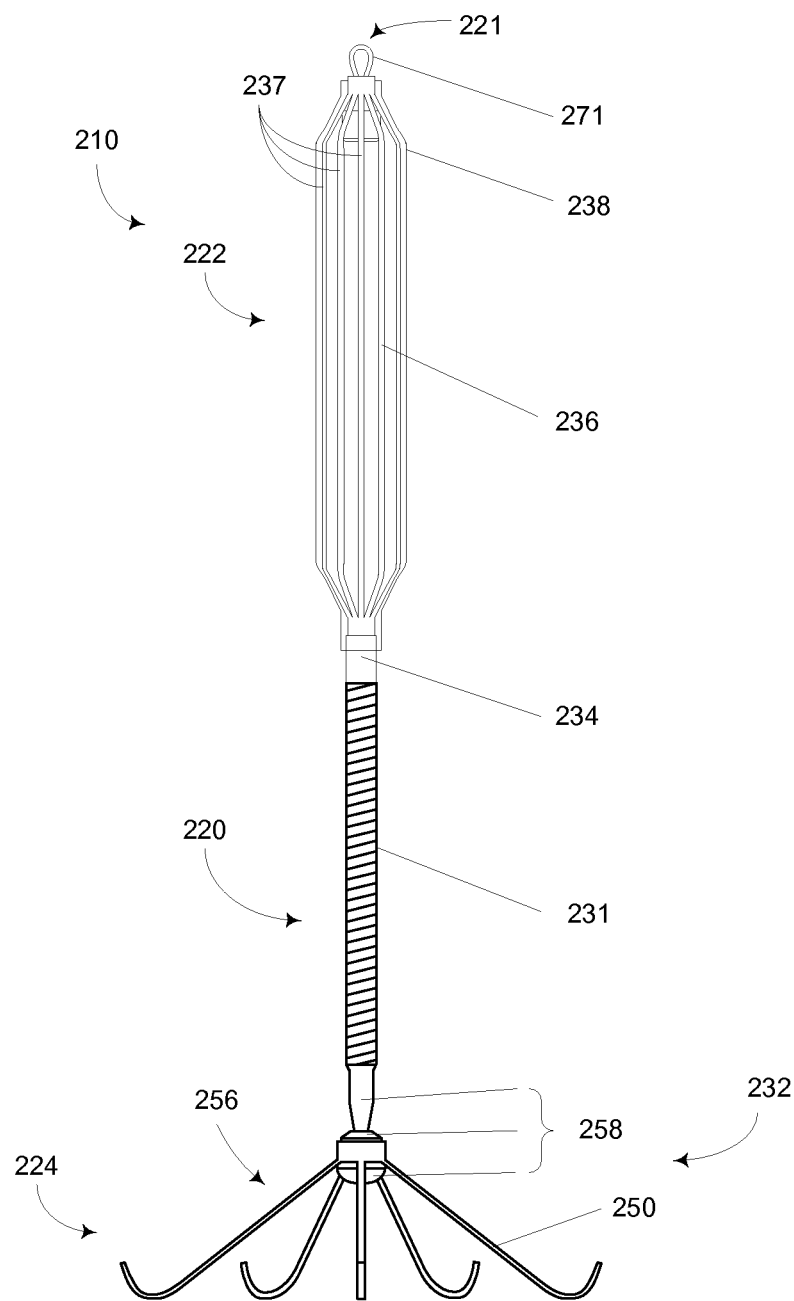

Longitudinal Cross-Section of the Implant

Outside View of loaded steerable catheter - Body of catheter shown as transparent to reveal parts inside Longitudinal Section View of loaded steerable Implant advanced through steerable to LV apex, pusher tube shown clear Implant deployed in LV Implant deployed in LV Implant successful - steerable, pusher tube and suture removed Steerable advanced as part of process to remove implant Steerable advanced to collapse umbrella and release from LV apex

SYSTEM AND METHOD FOR IMPLANTING A HEART IMPLANT

CROSS REFERENCE TO RELATED APPLICATIONS

The present application claims the benefit of U.S. Provisional Application Ser. No. 61/061,343, filed Jun. 13, 2008, which is hereby incorporated fully by reference.

FIELD

The present disclosure relates to the repair and/or correction of dysfunctional heart valves, and more particularly pertains to heart valve implants and systems and methods for delivery and implementation of the same.

BACKGROUND

A human heart has four chambers, the left and right atrium and the left and right ventricles. The chambers of the heart alternately expand and contract to pump blood through the vessels of the body. The cycle of the heart includes the simultaneous contraction of the left and right atria, passing blood from the atria to the left and right ventricles. The left and right ventricles then simultaneously contract forcing blood from the heart and through the vessels of the body. In addition to the four chambers, the heart also includes a check valve at the upstream end of each chamber to ensure that blood flows in the correct direction through the body as the heart chambers expand and contract. These valves may become damaged, or otherwise fail to function properly, resulting in their inability to properly close when the downstream chamber contracts. Failure of the valves to properly close may allow blood to flow backward through the valve resulting in decreased blood flow and lower blood pressure.

Mitral regurgitation is a common variety of heart valve dysfunction or insufficiency. Mitral regurgitation occurs when the mitral valve separating the left coronary atrium and the left ventricle fails to properly close. As a result, upon contraction of the left ventricle blood may leak or flow from the left ventricle back into the left atrium, rather than being forced through the aorta. Any disorder that weakens or damages the mitral valve can prevent it from closing properly, thereby causing leakage or regurgitation. Mitral regurgitation is considered to be chronic when the condition persists rather than occurring for only a short period of time.

Regardless of the cause, mitral regurgitation may result in a decrease in blood flow through the body (cardiac output). Correction of mitral regurgitation typically requires surgical intervention. Surgical valve repair or replacement may be carried out as an open heart procedure. The repair or replacement surgery may last in the range of about three to five hours, and may be carried out with the patient under general anesthesia. The nature of the surgical procedure requires the patient to be placed on a heart-lung machine. Because of the severity/complexity/danger associated with open heart surgical procedures, corrective surgery for mitral regurgitation is typically not recommended until the patient's ejection fraction drops below 60% and/or the left ventricle is larger than 45 mm at rest.

BRIEF DESCRIPTION OF THE DRAWINGS

Features and advantage of the claimed subject matter will be apparent from the following description of embodiments consistent therewith, which description should be considered in conjunction with the accompanying drawings, wherein:

FIG. 12A illustrates a perspective view of an embodiment of a retaining device in an open position consistent with the present disclosure;

FIG. 12B illustrates a perspective view of an embodiment of a retaining device in a closed position consistent with the present disclosure;

FIG. 14A illustrates a perspective view of an embodiment of a delivery device in a retracted position consistent with the present disclosure;

FIG. 14B illustrates a perspective view of an embodiment of a delivery device in an expanded position consistent with the present disclosure;

FIGS. 26A-26B illustrate a perspective view of an embodiment of an implant consistent with the present disclosure;

FIGS. 27A-27B illustrate a perspective view of another embodiment of an implant consistent with the present disclosure;

DESCRIPTION

The present disclosure relates to a heart implant and a system and method of implanting a heart implant. For example, the system and method according to one embodiment of the present disclosure may be used to implant a heart valve implant which may suitably be used in connection with the treatment, diagnostics and/or correction of a dysfunctional or inoperative heart valve. One suitable implementation for a heart valve implant consistent with the present disclosure is the treatment of mitral valve regurgitation. For the ease of explanation, the heart valve implant herein is described in terms of a mitral valve implant, such as may be used in treating mitral valve regurgitation as described in U.S. patent application Ser. No. 11/258,828 filed Oct. 26, 2005, which is fully incorporated herein by reference. However, a heart valve implant consistent with the present disclosure may be employed for treating, diagnosing and/or correcting other dysfunctional or inoperative heart valves. The present disclosure should not, therefore, be construed as being limited to use as a mitral valve implant. In addition, the system and method according to the present disclosure may be used to implant heart implants configured to be used in connection with the treatment, diagnostics and/or correction of other heart conditions. For example, and without limitation, the system and method consistent with the present disclosure may be used to implant a regurgitation implant configured to induce a controlled regurgitation in a heart valve (such as, but not limited to, a mitral heart valve), for example, in a manner that is generally consistent with advanced disease of the heart. The regurgitation implant may include a regurgitation implant as described in U.S. Ser. No. 11/940,724 filed Nov. 15, 2007, which is fully incorporated herein by reference.

According to one embodiment, a heart implant consistent with the present disclosure may comprise a heart valve implant configured to interact with at least a portion of an existing heart valve to prevent and/or reduce regurgitation. For example, at least a portion of one or more cusps of the heart valve may interact with, engage, and/or seal against at least a portion of the heart valve implant when the heart valve is in a closed condition. The interaction, engagement and/or sealing between at least a portion of at least one cusp and at least a portion of the heart valve implant may reduce and/or eliminate regurgitation in a heart valve, for example, providing insufficient sealing, including only a single cusp, e.g., following removal of a diseased and/or damaged cusp, and/or having a ruptured cordae. A heart valve implant consistent with the present disclosure may be used in connection with various additional and/or alternative defects and/or deficiencies.

Figure 1:
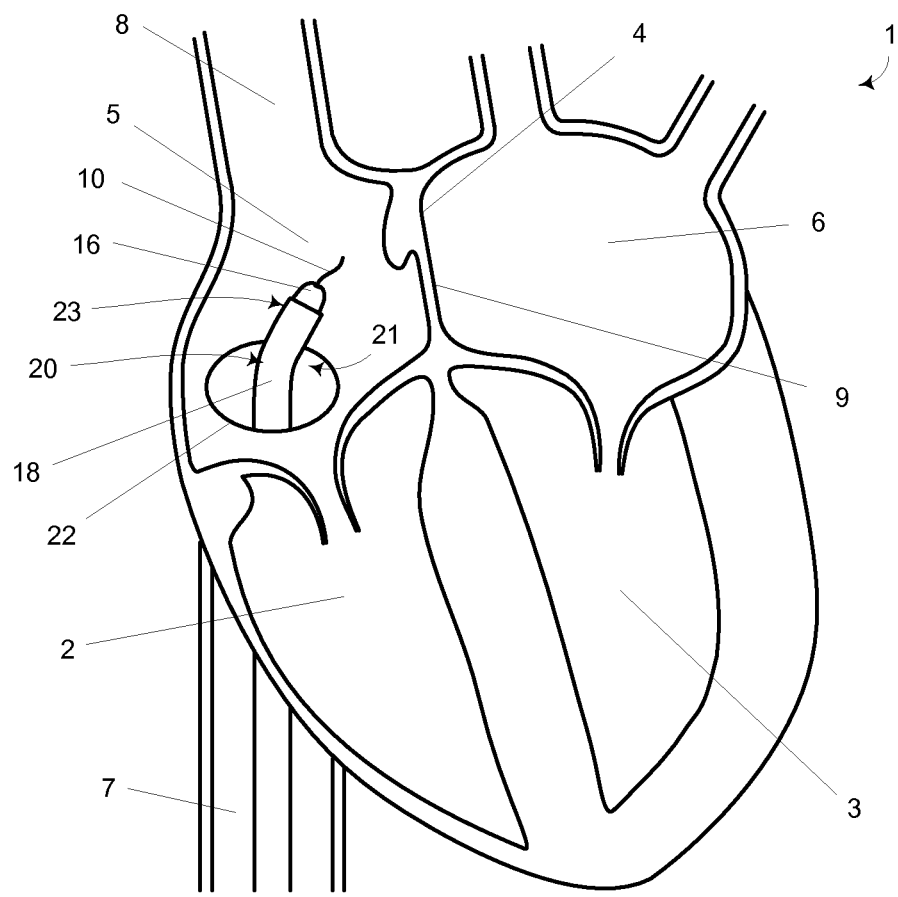
FIG. 1 illustrates a perspective view of an embodiment of a transseptal catheter in the right atrium consistent with the present disclosure.

For the ease of explanation, one embodiment of the system and method consistent with the present disclosure is described in terms of a system and method for implanting a mitral valve implant, such as may be used in treating mitral valve regurgitation. The system and method may generally comprise placing a guide wire into the left ventricle and advancing a mitral valve implant along the guide wire and into the left ventricle. For example, a guide wire may be initially placed into the left atrium of the heart, for example, by way of transseptal puncture of the heart from the right atrium through the fossa ovalis into the left atrium. The guide wire may be passed through the mitral valve into the left ventricle and a snaring or capturing device (for example, but not limited to, a snare catheter) may be placed into the left ventricle to capture or retain the guide wire. A balloon catheter may at least partially receive the guide wire and may be inflated to pass the guide wire through the mitral valve without damaging the mitral valve or becoming entangled in the mitral valve. The snaring device may be used to capture or retain the guide wire in the left ventricle. With the guide wire in the left ventricle, a mitral valve implant may be placed in the left ventricle. For example, a delivery catheter may be placed over the guide wire and guided into the left ventricle. Once the delivery catheter is in the left ventricle, the mitral valve implant may be placed received in a delivery lumen of the delivery catheter, and placed into the left ventricle from the delivery lumen, and secured within the left ventricle. As mentioned above, a system and method for delivery a mitral valve heart implant may comprise placing a guide wire into the left ventricle. Referring now to FIG. 1, a cross-sectional schematic view of a portion of a four chamber heart 1 is illustrated. The outflow tracts of the right and left ventricles 2, 3 are not shown in order to better illustrate the septum 4 between the right and left atria 5, 6. As shown, the inferior vena cava (IVC) 7 and superior vena cava (SVC) 8 communicate with the right atrium 5 which is separated from the left atrium 6 by the intra-atrial septum 4. While not a limitation of the present disclosure, it is may be advantageous to make the transseptal puncture through the fossa ovalis 9 since the fossa ovalis 9 is thinnest portion of the intra-atrial septum 4.

According to one embodiment consistent with the present disclosure, a guide wire 10 may be advanced up the IVC 7 and into the right atrium 5. The guide wire 10 may include any guide wire configured to be advanced up the IVC 7 and into the right atrium 5. Consistent with one embodiment, the guide wire 10 may be the same as the rail discussed herein; however, the guide wire 10 may also be separate and distinct from the rail. Without limitation, access to the right atrium 5 may be accomplished by way of the Seldinger wire technique. For example, the right femoral vein (not shown) may be accessed with a hollow needle (not shown) and a guide wire 10 may be inserted. The needle may be removed and a dilator 16 may be inserted over the guide wire 10. The sheath 18 of a catheter 20 (such as, but not limited to, a Mullins catheter or the like) having a pre-bent region 21 proximate the distal tip 23 of the catheter 20 may be inserted over the dilator 16. The sheath 18, dilator 16, catheter 20 and guide wire 10 may then be advanced up the IVC 7 through the opening 22 into the right atrium 5 as generally illustrated in FIG. 1.

Figure 2:
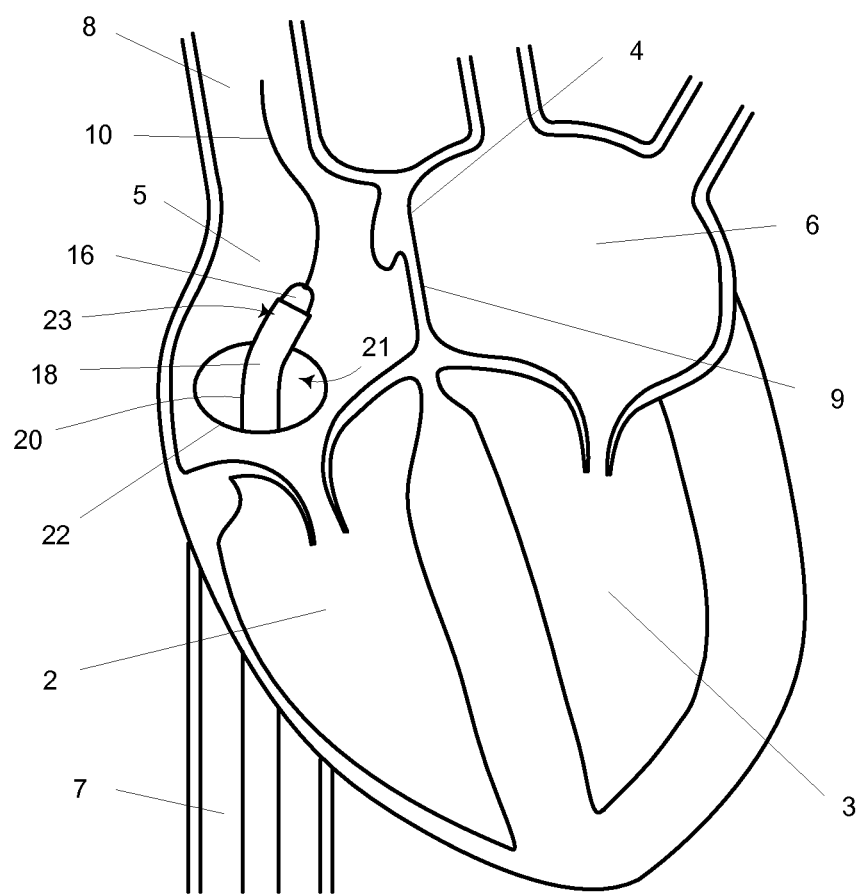
FIG. 2 illustrates a perspective view of an embodiment of a guide wire advanced into the superior vena cava consistent with the present disclosure.
Figure 3:
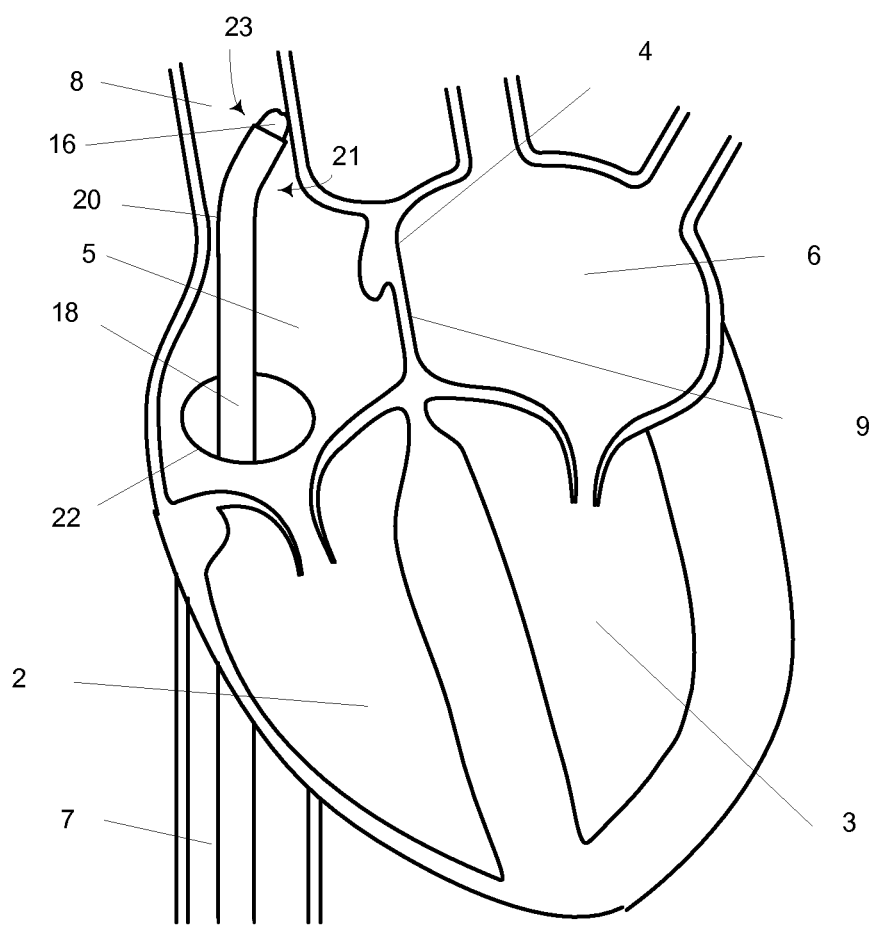
FIG. 3 illustrates a perspective view of an embodiment of a catheter advanced into the superior vena cava consistent with the present disclosure.

With the sheath 18, dilator 16, catheter 20 and guide wire 10 in the right atrium 5, access to the left atrium 6 may be achieved by transseptal puncture from the right atrium 5 through the intra-atrial septum 4. For example, at least a portion of the guide wire 10 may be advanced out of the distal tip 23 of the dilator 16, sheath 18 and/or catheter 20 as generally shown in FIG. 2. According to an embodiment, the guide wire 10 may be at least partially advanced into the SVC 8 as generally illustrated in FIG. 2 and the distal tip 23 of the catheter 20 may then be at least partially advanced along the guide wire 10 into the SVC 8 as generally illustrated in FIG. 3. Because the SVC 8 is a thin-walled vein, it may be advantageous to place the guide wire 10 in the SVC 8 and then advance the catheter 20 along the guide wire 10 since the spring-tipped atraumatic guide wire 10 reduces the potential for damaging the SVC 8 compared to the catheter 20 and dilator 16.

Figure 4:
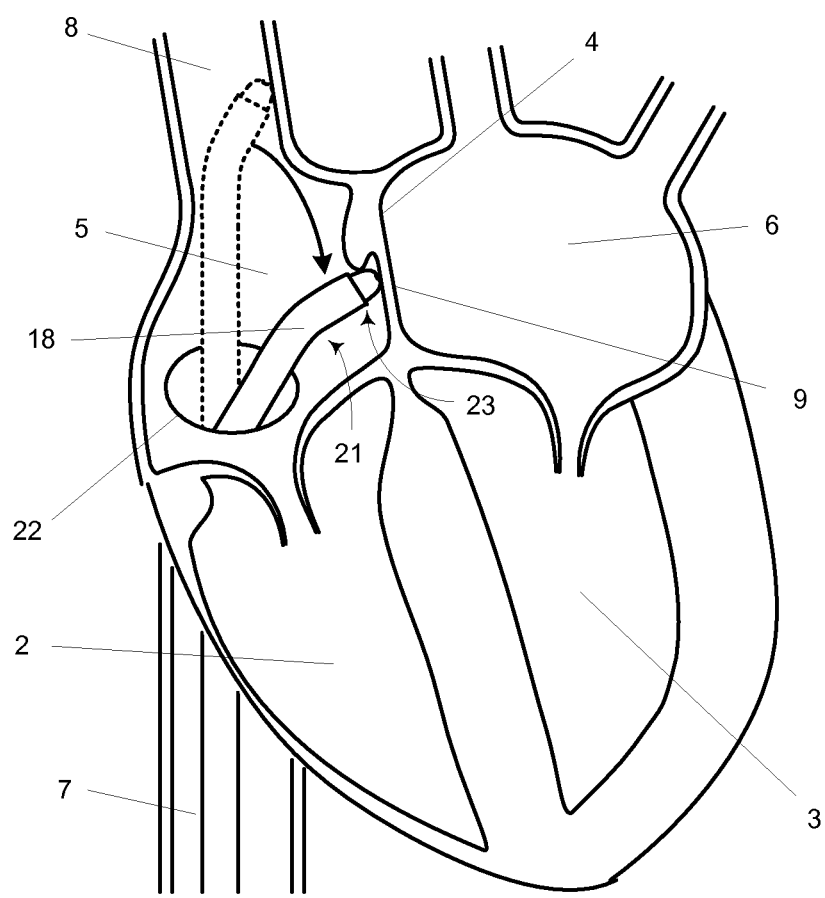
FIG. 4 illustrates a perspective view of an embodiment of a catheter tip against the fossa ovalis consistent with the present disclosure.
Figure 5:
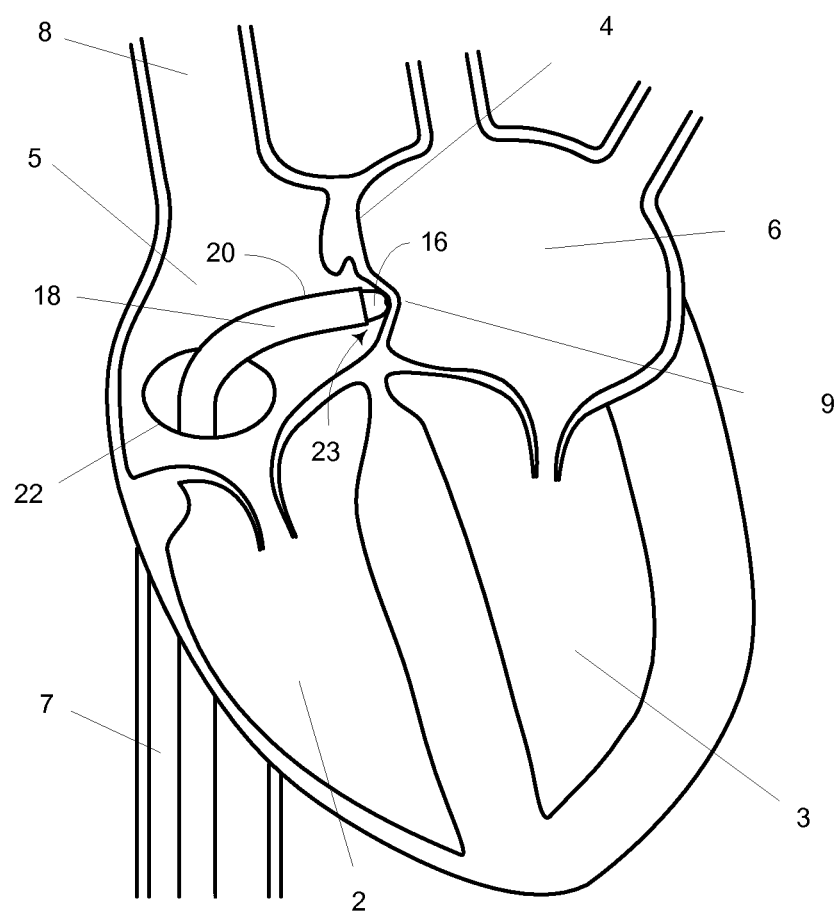
FIG. 5 illustrates a perspective view of an embodiment of a catheter tenting the fossa ovalis consistent with the present disclosure.

With the distal tip 23 at least partially received in the SVC 8, the guide wire 10 may be retracted into the dilator 16 and the catheter 20 may be retracted (i.e., pulled downward) such that the pre-bent portion 21 of the sheath 18 facilitates guiding the distal tip 23 to the fossa ovalis 9 as generally illustrated in FIG. 4. For example, using one or more visualization techniques (such as, but not limited to, intracardiac echo (ICE), fluoroscopy, and the like), the sheath 18 may be retracted proximally, dragging the distal tip 23 along the intra-atrial septum 4 until the distal tip 23 is positioned proximate to the fossa ovalis 9. Optionally, the position of the sheath 18 relative to the fossa ovalis 9 may be confirmed by gently pushing the sheath 18 distally against the intra-atrial septum 4 to "tent" the fossa ovalis 9 as generally illustrated in FIG. 5. The "tenting" of the fossa ovalis 9 may be seen on ICE, fluoroscopy or the like.

Figure 6:
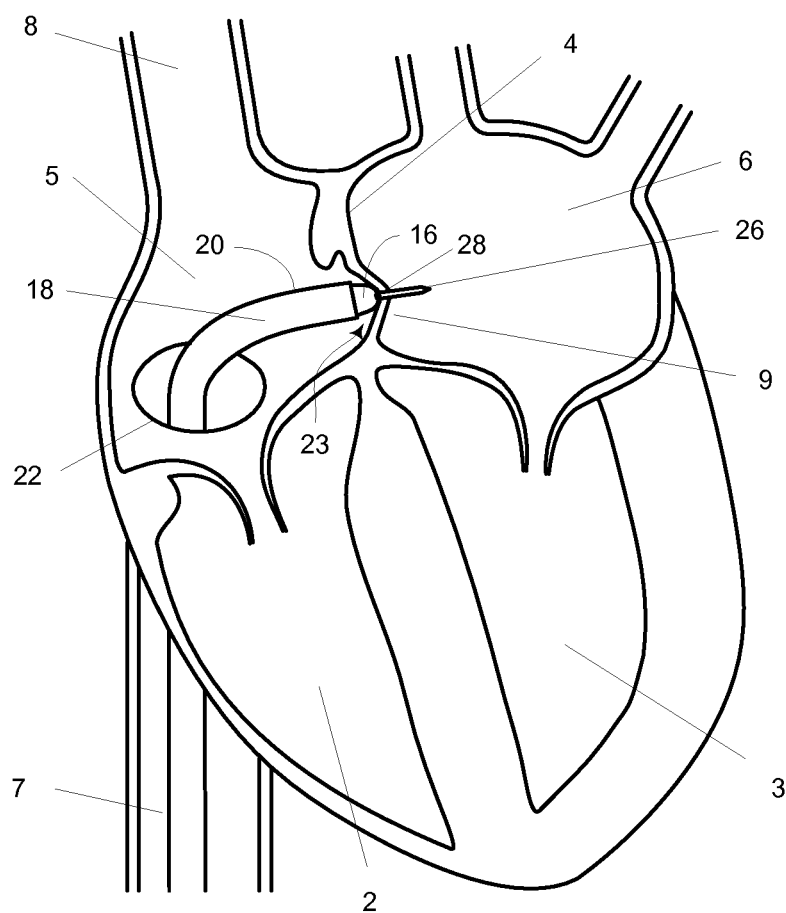
FIG. 6 illustrates a perspective view of an embodiment of a needle puncturing the fossa ovalis consistent with the present disclosure.
Figure 7:
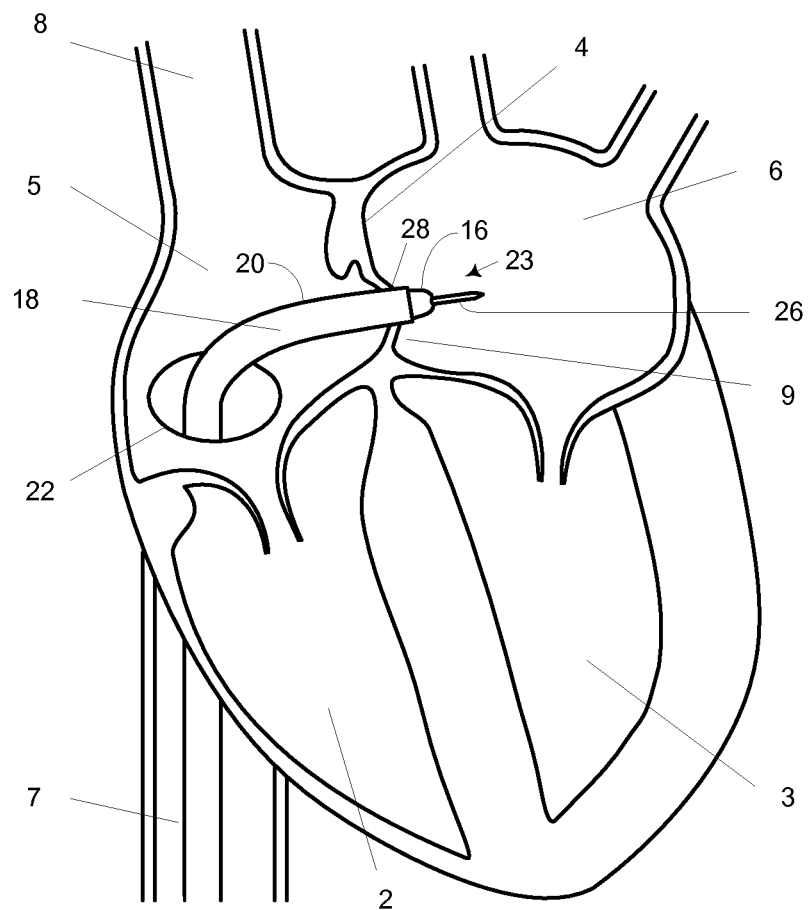
FIG. 7 illustrates a perspective view of an embodiment of a transseptal catheter punctured through the fossa ovalis consistent with the present disclosure.
Figure 8:
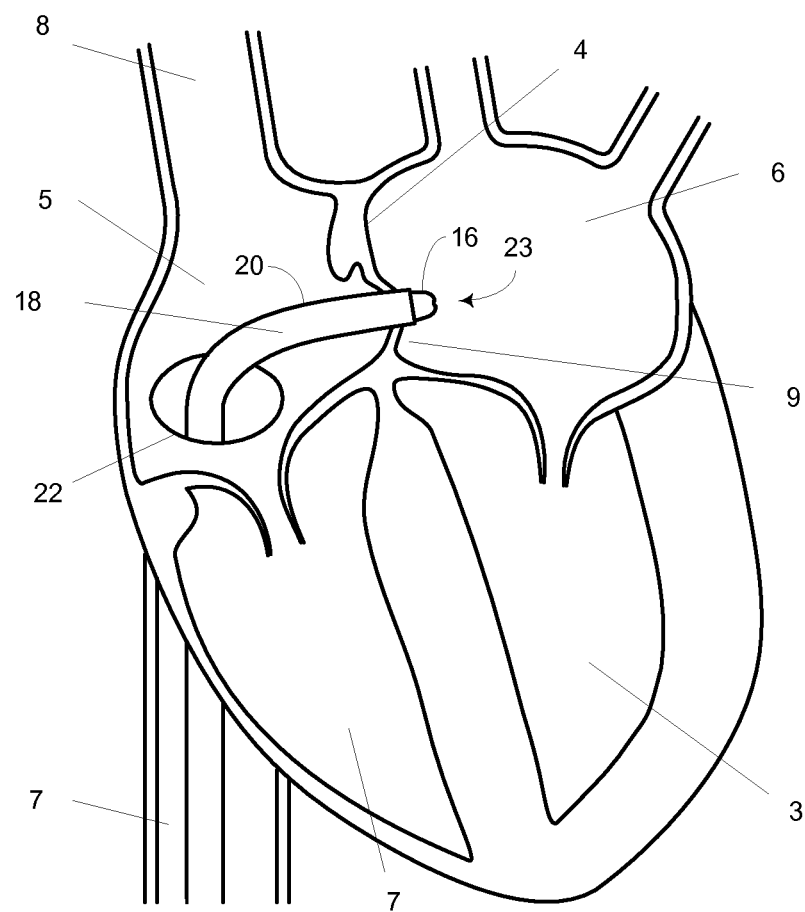
FIG. 8 illustrates a perspective view of an embodiment of a transseptal catheter in the left atrium with the needle removed consistent with the present disclosure.

With the distal tip 23 proximate and/or contacting the fossa ovalis 9, the guide wire 10 may be removed from the catheter 20 and a transseptal needle 26 may be advanced through the catheter 20 towards the distal end 23 of the catheter 20 as generally shown in FIG. 6. The position of the catheter 20 may optionally be confirmed (for example, but not limited to, by "tenting") and the transseptal needle 26 may be advanced out of the distal tip 23 to form a puncture 28 through the fossa ovalis 9 and into the left atrium 6. The sheath 16, dilator 28 and catheter 20 may than be advanced through the puncture 28 of the fossa ovalis 9 and into the left atrium 6 as generally shown in FIG. 7. Once the sheath 16, dilator 28 and catheter 20 are through the fossa ovalis 9, the needle 26 may be removed from the catheter 20 as generally shown in FIG. 8.

Figure 9:
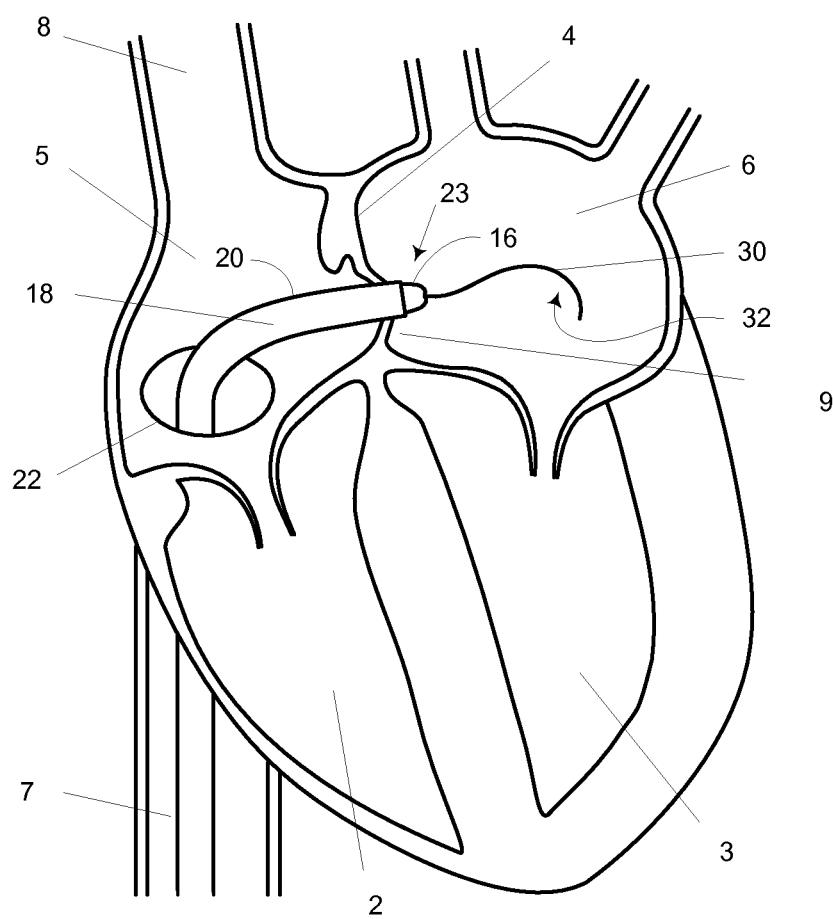
FIG. 9 illustrates a perspective view of an embodiment of a rail advanced into the right atrium through the transseptal catheter consistent with the present disclosure.
Figure 10:
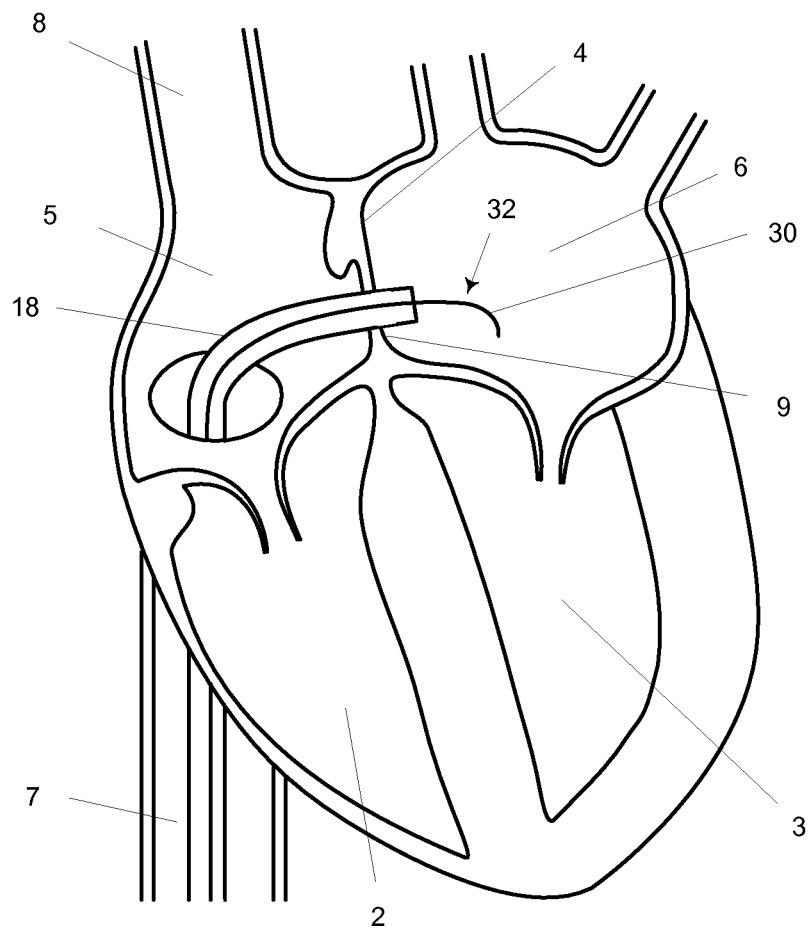
FIG. 10 illustrates a perspective view of an embodiment of a sheath and dilator removed with a rail in the right atrium consistent with the present disclosure.

With the catheter 20 in the left atrium 6, a rail 30 may be advanced through the catheter 20 until at least a portion of the distal tip 32 of the rail 30 extends from the distal tip 23 of the catheter 20 and into the left atrium 6 as generally illustrated in FIG. 9. Once the distal tip 32 of the rail 30 is disposed in the left atrium 6, the dilator 16 and the sheath 18 may be removed, leaving just the rail 30 in the left atrium 6 as generally illustrated in FIG. 10.

The rail 30 may be used as a guide for advancing other devices into the heart 1, and ultimately, into the left ventricle 3. As such, the rail 30 should be sufficiently stiff to resist undesirable bending and/or kinking and to resist undesirable movement of the distal tip 32 when placed in the apex of the left ventricle as will be explained in greater detail. For example, the rail 30 may comprise a stiff, 0.018" diameter guide wire having a stiffness of approximately 19,900,000 psi. The stiffness of the rail 30 was determined as follows.

When a force is applied to a long thin column, there is no movement of the column until a minimum critical buckling force is achieved, $P_{cr}$, then further buckling occurs, though the force does not increase. For a long column of uniform cross-section and length l, which buckles under a critical force, $P_{cr}$, the following formula applies:

$$P_{cr} = n\pi^2 \frac{EI}{L^2}$$

Where:
  n=a constant that is equal to 4 if both ends of the column are clamped and cannot move or rotate.
  E=Modulus of elasticity of the material (psi)
  I=Moment of inertia (in$^4$)
For a circular cross-section the moment of inertia is:

$$I = \frac{\pi d^4}{64}$$

Substituting for l in the first equation for $P_{cr}$ leads to:

$$P_{cr} = n\pi^3 \frac{Ed^4}{64L^2}$$

And solving for the modulus leads to:

$$E = \frac{64L^2 P_{cr}}{n\pi^3 d^4}$$

Based on the above, an 8 cm section of the rail 30 was tested and a buckling force of 0.41 lbs. was determined. Therefore, $$E = \frac{64(3.15)^2(0.41)}{4\pi^3(0.018)^4} = 19,900,000 \text{ psi}$$

This stiffness of the rail 30 may therefore be approximately 19,900,000 psi. The rail 30 consistent with one embodiment of the present disclosure may therefore be 15 times greater than a typical 0.018" guide wire (for example a 0.018" angled standard exchange guide wire made by Merit Medical Systems of South Jordan, Utah, Model H20STDA18260EX which was determined to have a stiffness of approximately 1,360,000 psi based on the same methodology). Of course, the rail 30 may have a stiffness greater than or less than 19,900,000 psi and may have a diameter greater than or less than 0.018". The rail 30 should have a diameter and stiffness sufficient to fit within the delivery catheter 90 and to allow an implant to be advanced along the length without buckling or kinking.

Figure 11:
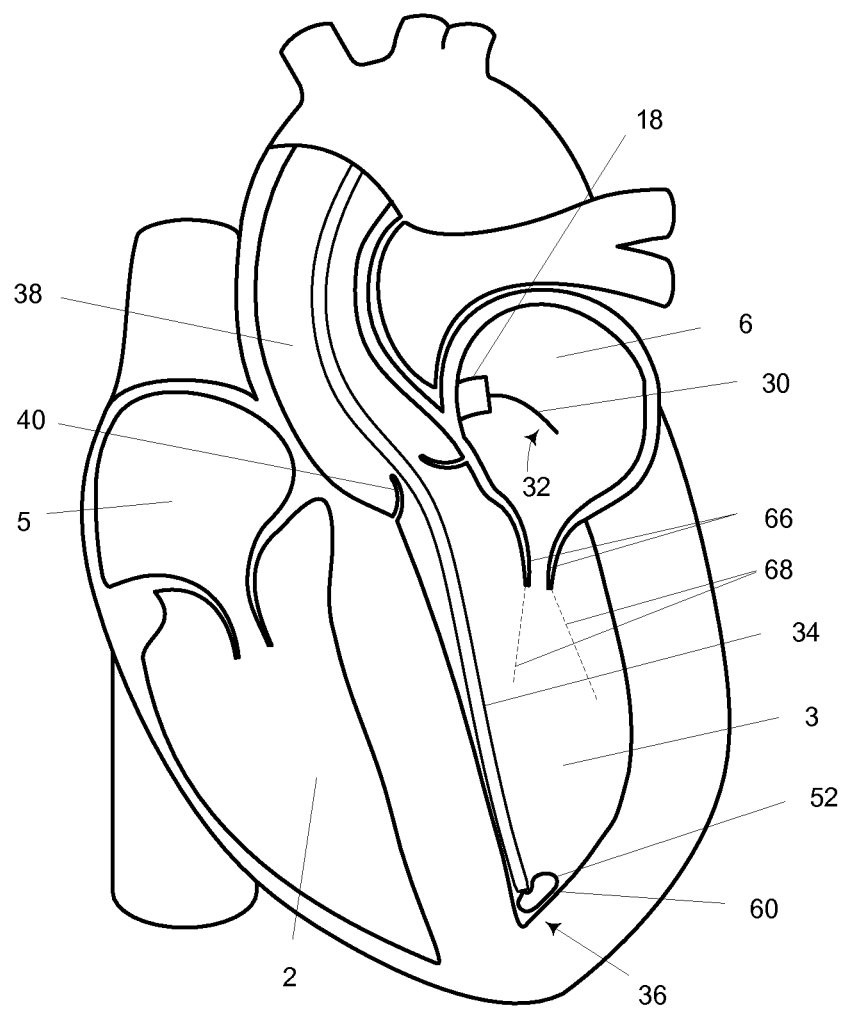
FIG. 11 illustrates a perspective view of an embodiment of a retaining device advanced to the left ventricle consistent with the present disclosure.
Figure 13:
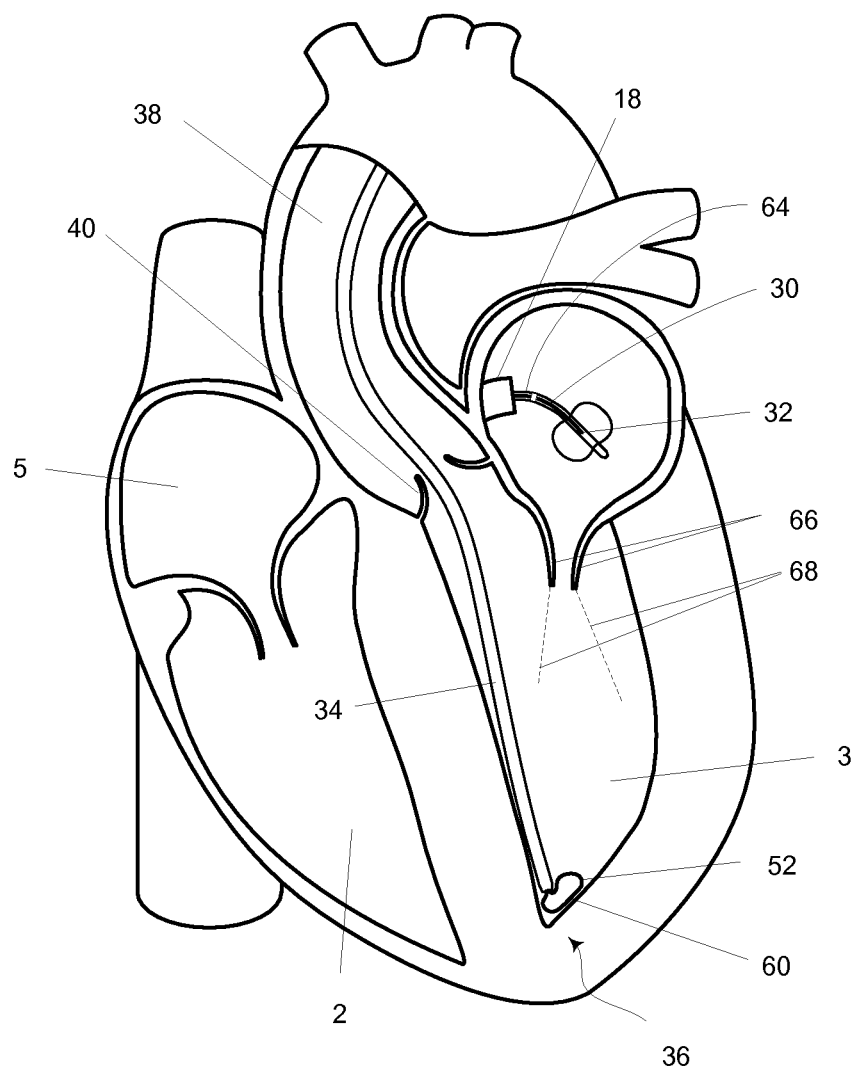
FIG. 13 illustrates a perspective view of an embodiment of delivery device in an expanded position in the left atrium consistent with the present disclosure.

Turning now to FIG. 11, a retaining device 34 may be advanced into the left ventricle 3. For example, the retaining device 34 may be advanced into the left ventricle 3 proximate to the apex 36 of the left ventricle 34. Consistent with one embodiment of the present disclosure, the retaining device 34 may be advanced from the femoral artery, through the aorta 38 and aortic valve 40 and into the left ventricle 3 proximate to the apex, however, the retaining device 34 may be advanced to the left ventricle 3 according to a variety of different techniques.

The retaining device 34 may comprise any device configured to be delivered at least proximate to the apex 36 of the left ventricle 3 and configured to retain at least a portion of the rail 30 and to generally fix the position of at least a portion of the rail 30 within the left ventricle 3, and in particular, proximate to the apex 36. While not a limitation unless specifically claimed as such, one example of a retaining device 34 is shown in FIGS. 12A and 12B. For example, the retaining device 34 may comprise a snaring device 42 configured to substantially retain at least a portion of the rail 30 about a distal end 44. The snaring device 42 may comprise a catheter 46 comprising at least one shaft 48 defining at least one lumen 50 and may include a tapered distal end 44. A wire loop 52 may be configured to extend outwardly beyond the distal end 44 of the catheter 46 to form a loop 60 in a first position as generally illustrated in FIG. 12A and to be at least partially retracted within the catheter 46 in a second position as generally illustrated in FIG. 12B such that at least a portion of the wire loop 52 may be disposed within the lumen 50 to retain the rail 30. The wire loop 52 may therefore retain the rail 30 by being tightened around the rail 30 and to hold the rail 30 against the distal end 44 of the catheter 46.

The catheter 46 may comprise an 8 French catheter having a diameter of approximately 0.105". The wire loop 52 may be configured to be slideably disposed within the catheter 46 and may comprise a wire having a diameter of approximately 0.021" and may define wire loop 60 (when in the first position) comprising a generally oval or circular shape having a diameter of approximately 0.42" across and may extend beyond the distal end 44 a length of approximately 0.693".

The snaring device 42 may also comprise a hub 54, for example, but not limited to, a Luer hub, coupled to a proximal end 56 of the catheter 46. At least a portion of the wire loop 52 may extend beyond the proximal end 56 of the catheter 46. As shown, the wire loop 52 may comprise a single length of wire disposed through the lumen 50 and having both ends 58a, 58b extending beyond the proximal end 56 and beyond the hub 54. According to this embodiment, a user may retain the rail 30 by first disposing the loop 60 of the wire loop 52 around at least a portion of the rail 30. With at least a portion of the rail 30 within the loop 60, the user may urge one or more of the ends 58a, 58b proximally (i.e., from the distal end 52 towards the proximal end 56), thereby retracting the loop 60 and the wire loop 52 into the snaring device 42. As the loop 60 is retracted, the loop 60 may tighten around the rail 30 and may generally retain the rail 30 against the distal end 44 of the catheter 46. A clamp 62 may be placed about the ends 58a, 58b of the wire loop 52 to keep the loop 60 tight, thereby retaining the rail 30 against the catheter 46.

While the wire loop 52 has been described having both ends 58a, 58b extending beyond the proximal end 56, the wire loop 52 may also have a single end 58 extending beyond the proximal end 56 and second end configured to form a loop 60 and to be disposed generally about the distal end 44. Other embodiments are also possible and are within the scope of the present disclosure, for example, but not limited to, a spring biased retaining device 34 and/or a retaining device 34 comprising a plurality of fingers configured to be extended beyond the distal end 44 and to be retracted proximally.

Turning now to FIGS. 13-17, the rail 30 may be placed in the left ventricle 3. For example, with the rail 30 in the left atrium 6, a delivery device 64 may be used to advance the rail 30 to the left ventricle 3. The delivery device 64 may be configured to receive at least a portion of the rail 30 (for example, at least the distal tip 32 of the rail 30) and to pass through the cusps 66 and chordae (not shown for clarity) of the mitral valve 68. The delivery device 64 may therefore be configured to reduce the potential for the rail 30 to become entangled within and/or damage the cusps 66 and chordae of the mitral valve 68.

One example of a delivery device 64 consistent with the present disclosure is generally illustrated in FIGS. 14A and 14B. The delivery device 64 may comprise a catheter 72 having a shaft 74 defining at least one lumen 76 configured to at least partially receive the rail 30. The catheter 72 may also comprise a distal tip 78 (for example, but not limited to a tapered distal tip) and an expanding portion 80 disposed generally proximate to the distal tip 78. The expanding portion 80 may be configured to expand from a first position in which the expanding member 80 is generally collapsed as generally illustrated in FIG. 14A to a second position in which the expanding member 80 is expanded as generally illustrated in FIG. 14B. As shown in FIG. 14A, the expanding portion 80 may have a diameter approximately equal to the diameter of the shaft 74 when in the first position and may have a diameter greater than the diameter of the shaft 74 when in the second position.

The diameter of the expanding portion 80 should be small enough in the first position to be advanced over the rail 30 to the left atrium 6 and large enough when in the second position to be advanced through the cusps 66 and chordae of the mitral valve 68 to reduce the potential of damaging the heart 1 and/or getting entangled within the mitral valve 68. For example, the shaft 74 may have a diameter of approximately 0.062" (e.g., a 5 Fr) and a length of approximately 110 cm or greater. The expanding portion may diameter of approximately 0.100" in the first position and a diameter of approximately 15 mm to approximately 20 mm cm in the second position with a length of approximately 8 to approximately 10 mm.

According to one embodiment consistent with the present disclosure, the delivery device 64 may comprise a balloon catheter 70. The expanding portion 80 of the balloon catheter 70 may comprise a balloon 82 or the like which may be selectively collapsed and/or expanded. For example, the balloon 82 may comprise a resiliently expandable/collapsible material such as, but not limited to, silicone, Yulex™ or the like. The balloon catheter 70 may comprise a first lumen 76a configured to receive the rail 30 as discussed above and at least a second lumen 76b configured to selectively collapse and/or expand the balloon 82. For example, the second lumen 76*b* may be configured to communicate a fluid (such as, but not limited to, a liquid and/or gas) to selectively collapse and/or expand the balloon 82. The fluid may comprise carbon dioxide and may optionally include a contrast media to facilitate viewing the balloon 82 with one or more visualization techniques (for example, but not limited to, fluoroscopy or the like).

One or more of the lumens 76*a*, 76*b* may comprise a hub 84*a*, 84*b* disposed proximate a proximal end and may be coupled to the catheter 72 by way of one or more couplers 86. In addition, one or more of the hubs 84*a*, 84*b* may also include a coupler or connection 88*a*, 88*b* configured to be coupled to a rail lumen and balloon lumen (not shown), respectively. The shaft 74 of the catheter 72 may comprise one or more position identifiers 91*a*-91*n* configured to facilitate positioning of the balloon catheter 70 (and in particular, the distal tip 78 and/or the balloon 82). For example, the position identifiers 91*a*-91*n* may comprise radiopaque markers 91*a*-91*n* disposed about the region of the distal tip 78. The position markers 91*a*-91*n* may be spaced evenly along the shaft 74 (such as, but not limited to, approximately 2 cm intervals from the distal tip 78) and may be used to verify the position of the balloon catheter 70 and/or for sizing the implant to be delivered. The balloon catheter 70 may have an overall length (i.e., from the distal tip 78 to the couplers 88*a*, 88*b*) of approximately 145 cm or less.

Figure 15:
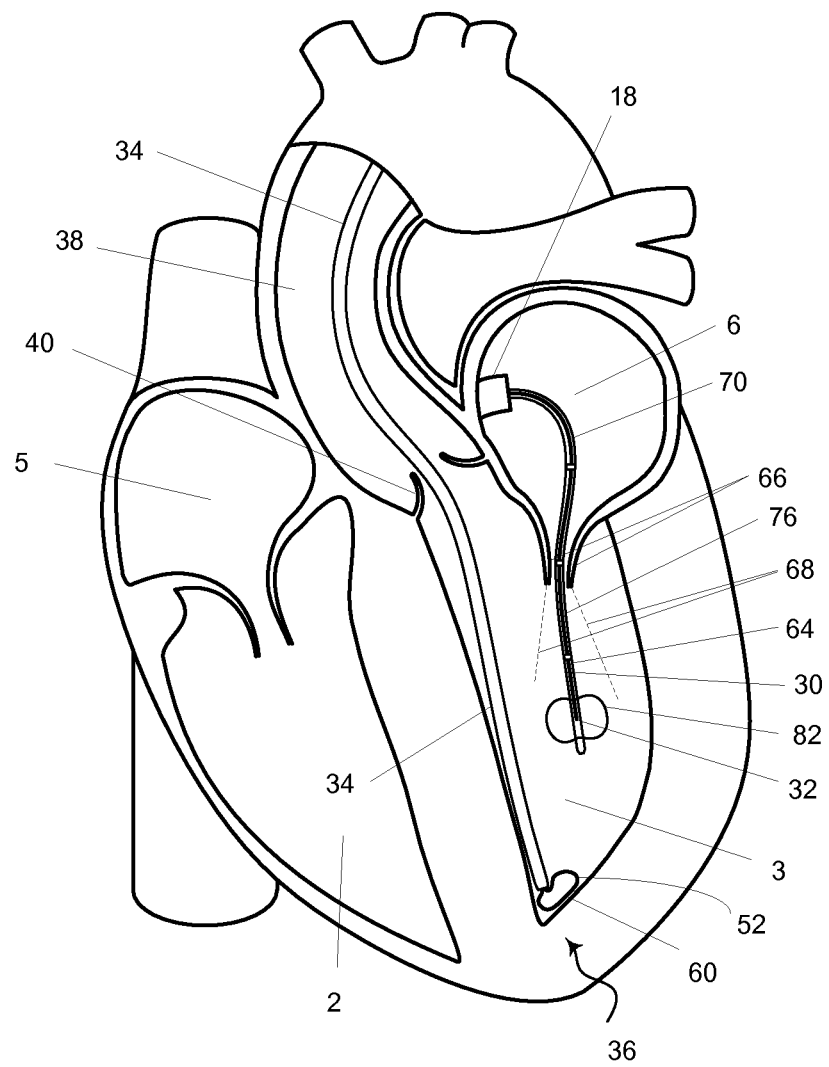
FIGS. 15A-C illustrate a various views of an embodiment of a delivery device in an expanded position through the mitral valve and in the left ventricle consistent with the present disclosure.
Figure 16:
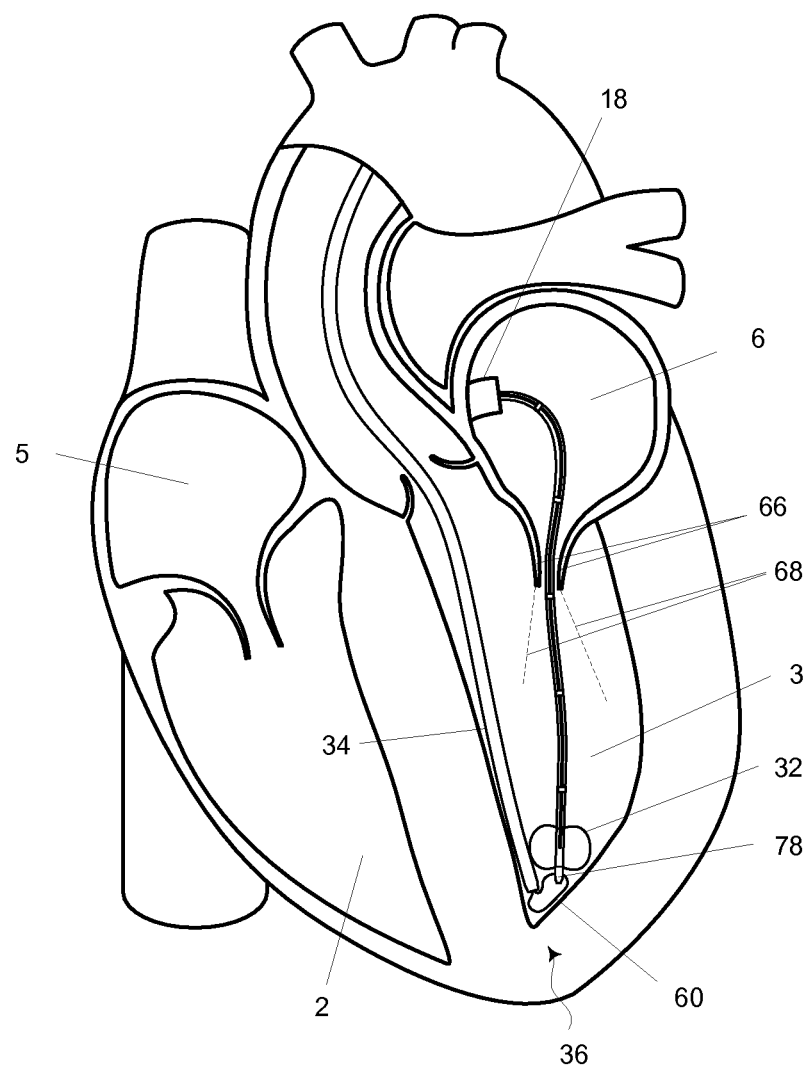
FIG. 16 illustrates a perspective view of an embodiment of a delivery device proximate the apex of the left ventricle atrium consistent with the present disclosure.

Turning back to FIG. 13, with the distal tip 32 of the rail 30 received in the lumen 76 of the balloon catheter 70, the balloon 82 may be expanded and advanced through the mitral valve 68 as generally illustrated in FIG. 15. As mentioned above, receiving the rail 30 within the balloon catheter 70 and expanding the balloon 82 may reduce the potential for entangled and/or damage to the cusps 66 and chordae of the mitral valve 68 as the balloon catheter 70 and the rail 30 are advanced through the mitral valve 68 into the left ventricle 3. The flow of blood through the mitral valve 68 may facilitate advancement of the balloon catheter 70 through the mitral valve 68 and to the apex 36 of the left ventricle as generally illustrated in FIG. 16.

Figure 15B:
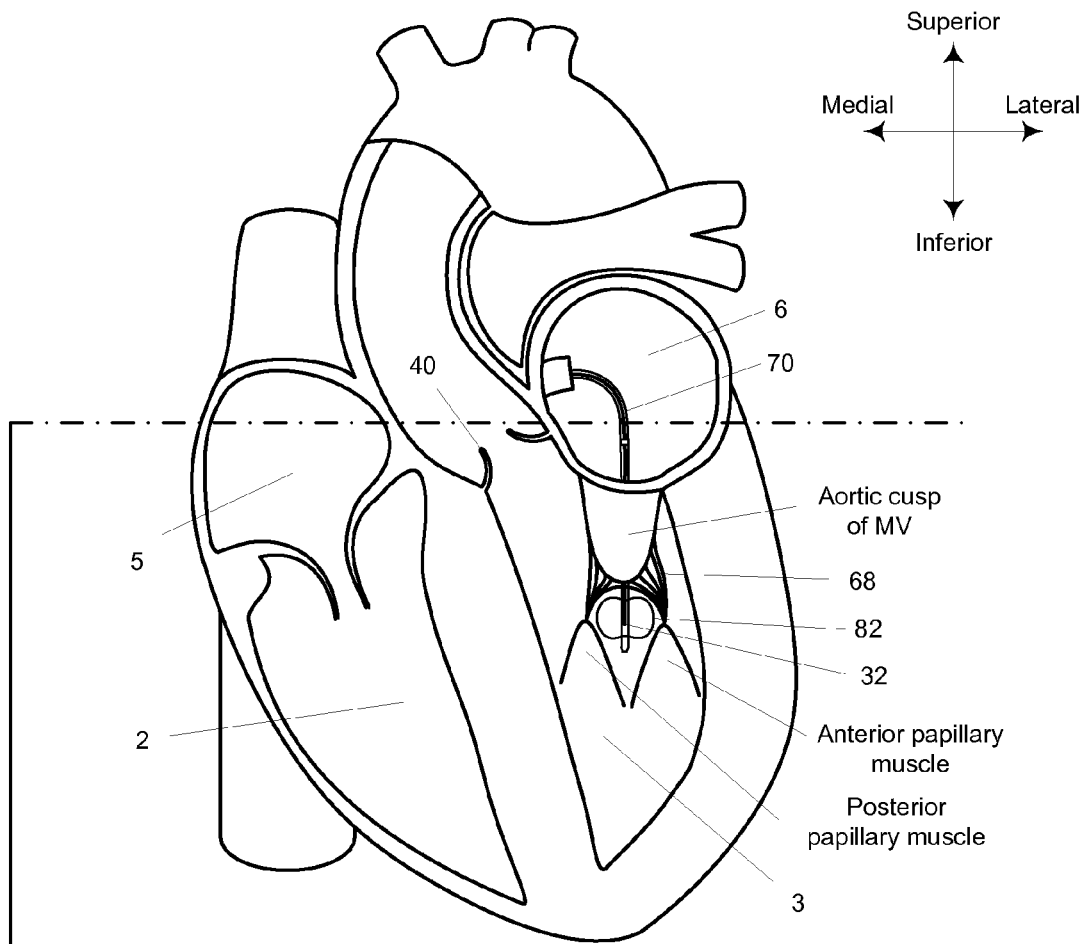
Figure 15C:
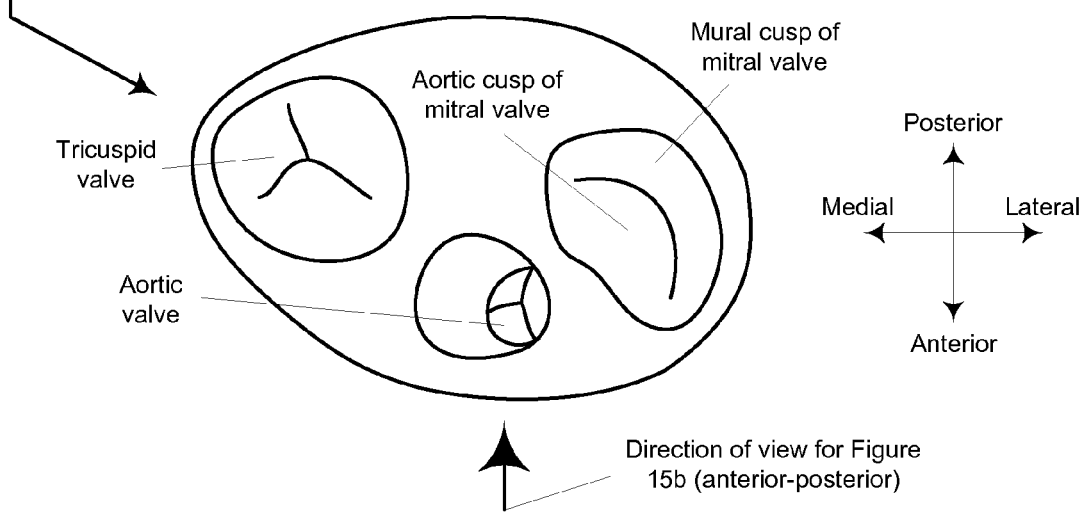

The orientation of the cusps 66 (also called leaflets) of the mitral valve 68 are shown schematically in all figures of the heart except for FIG. 15B and FIG. 15C. FIG. 15*b* shows the same anterior-posterior section of the heart of many of the other figures, but it also shows more anatomically correct detail of the mitral valve cusps 66. The aortic cusp, which is closest of the two mitral cusps to the aortic valve, may be seen in FIG. 15B and the other cusp, the mural cusp, is not seen in this view. The balloon 82 is illustrated passing through a gap formed by the two papillary muscles, the chordae 68 which connect the tips of the papillary muscles to the aortic cusp, and the floor of the left ventricle. Not shown are the chordae that connect the same papillary muscles to each side of the mural cusp. This gap may only exist during left ventricular diastole, when the left ventricle is relaxed and filled with blood flowing in from the left atrium.

FIG. 15C is a sectional view taken from FIG. 15B. When viewed from the anterior (or front), the only mitral cusp which is clearly visible is the aortic cusp. From these figures, it can be understood that the passage of the balloon down through the mitral valve takes a path that is inferior (down), anterior (to the front) and a little bit medial (toward the center). If the balloon takes any other pathway through the mitral valve, the placement of the balloon may not allow the guidewire to be snared in the apex of the left ventricle as described herein.

Figure 17:
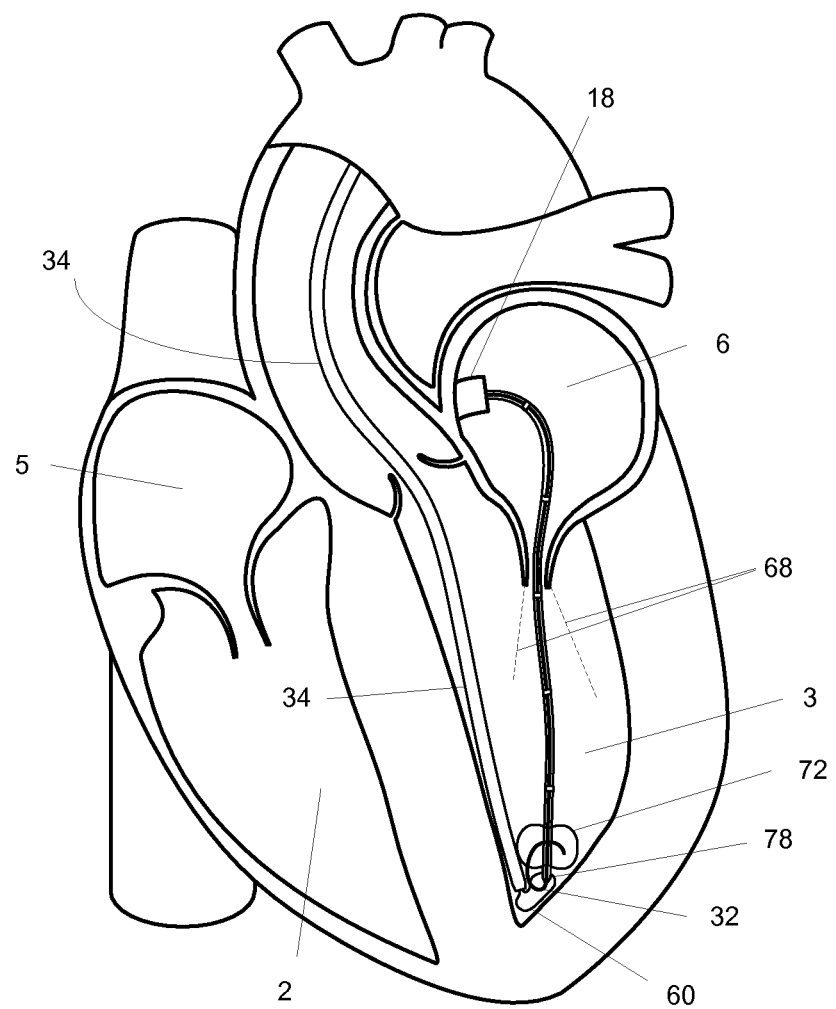
FIG. 17 illustrates a perspective view of an embodiment of a rail within the retaining device proximate the apex in the left ventricle consistent with the present disclosure.
Figure 18:
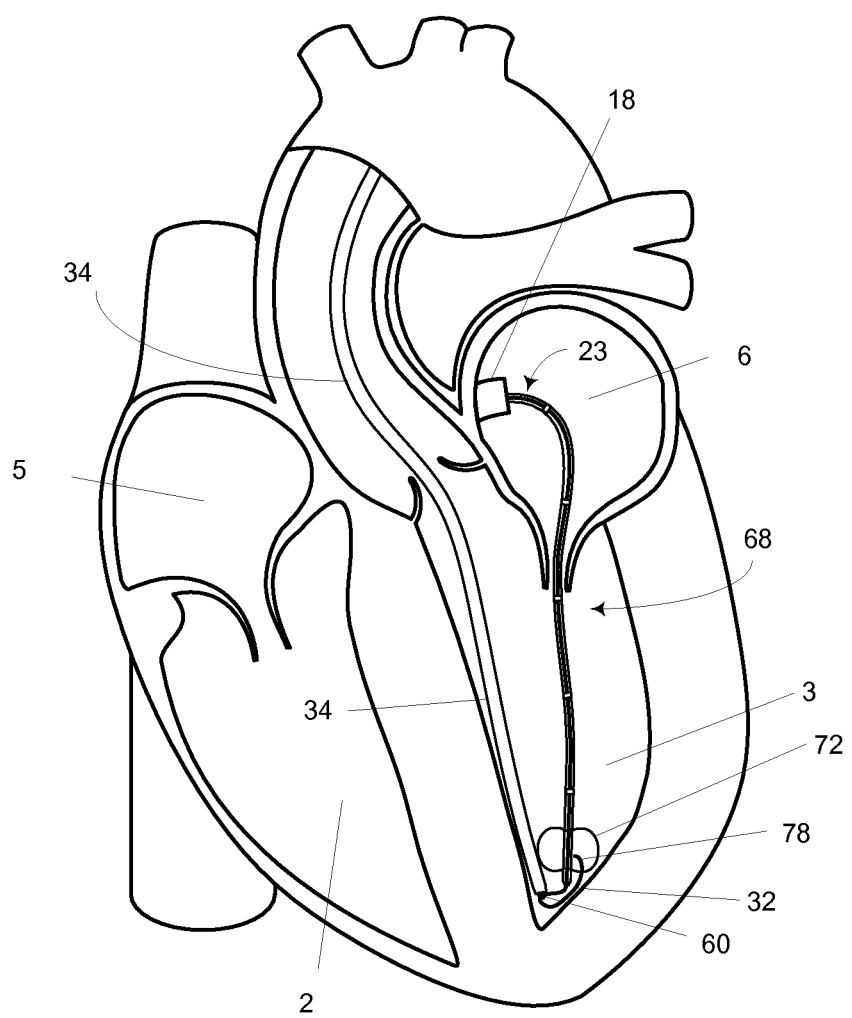
FIG. 18 illustrates a perspective view of an embodiment of a rail retained by the retaining device proximate the apex in the left ventricle consistent with the present disclosure.

With the distal tip 78 of the balloon catheter 70 disposed proximate the apex 36, the rail 30 may be advanced outwardly through the distal tip 78 as generally illustrated in FIG. 17. When at least the distal tip 32 of the rail 30 is extended beyond the distal tip 78, the distal tip 32 of the rail 30 may be snared or captured with the loop 60 of the retaining device 34 as generally illustrated in FIG. 18.

Figure 19:
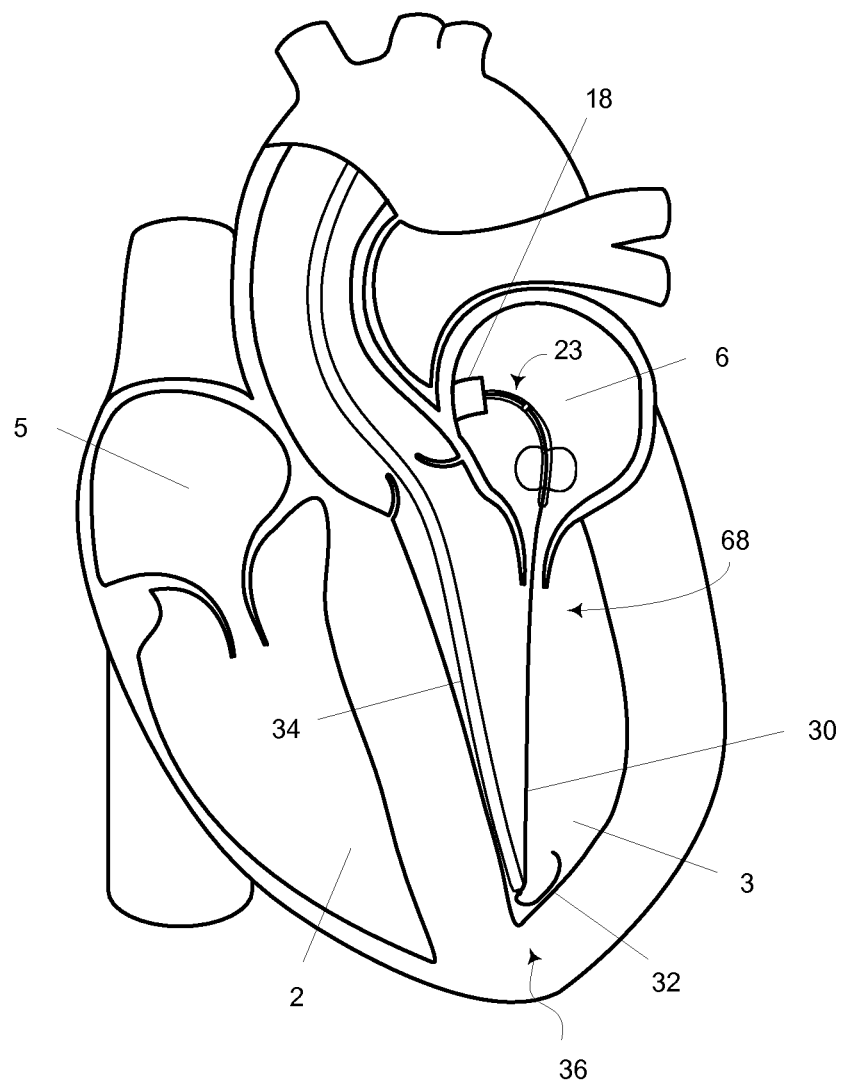
FIG. 19 illustrates a perspective view of an embodiment of the delivery device pulled back into the left atrium with a rail within the retaining device proximate the apex in the left ventricle consistent with the present disclosure.
Figure 20:
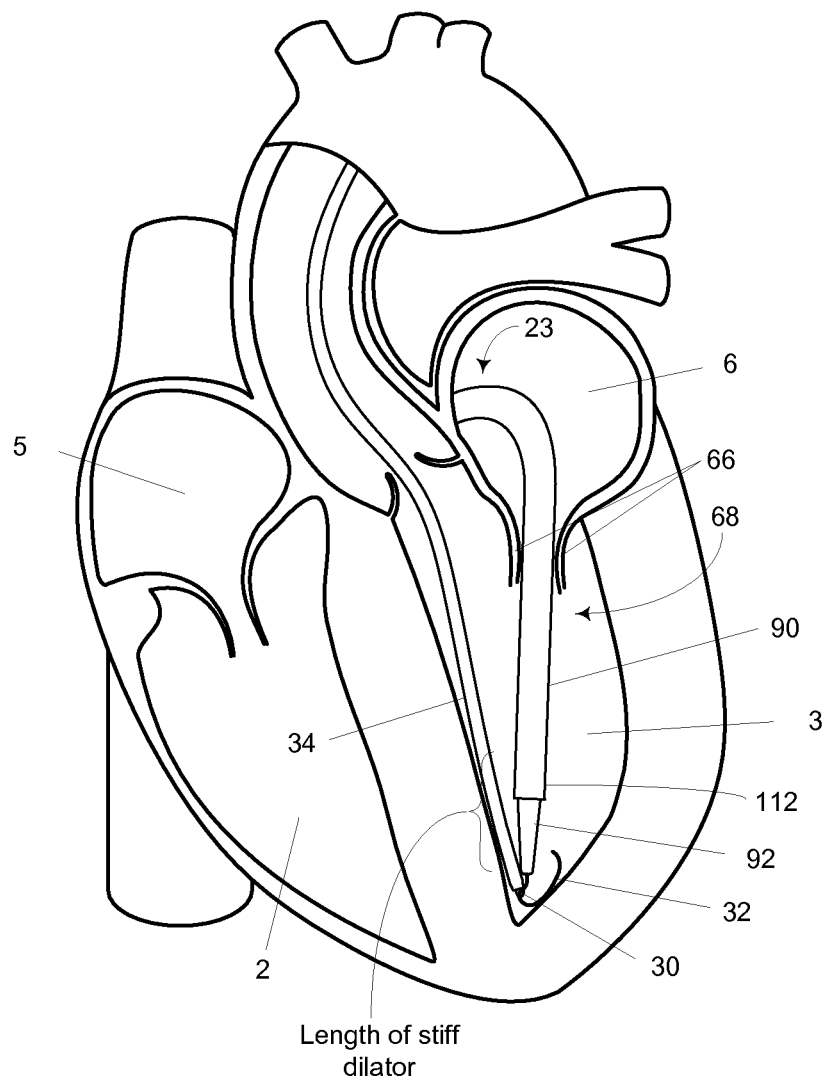
FIG. 20 illustrates a perspective view of an embodiment of a delivery catheter advanced proximate the apex in the left ventricle consistent with the present disclosure.

Once the distal tip 32 of the rail 30 is retained by the retaining device 34, the rail 30 may be generally held in place relative to the apex 36 and the balloon 72 may be retracted away from the rail 30 and through the mitral valve 68 as generally illustrated in FIG. 19. According to one embodiment consistent with the present disclosure, the balloon 30 may be retracted through the mitral valve 68 to the transseptal puncture 23 with the balloon in the expanded position. The balloon 72 may optionally be run back down the rail 30 through the mitral valve 68 and then retracted again to assure that the rail 30 is properly positioned and anchored by the retaining device 34 proximate the apex 36 to provide a "free and clear" pathway for the introduction of the implant over the rail 30. Once a pathway has been established, the balloon 72 may be collapsed and removed completely from the patient.

With the rail 30 in place proximate the apex 36, the implant 110 may be delivered to the left ventricle 3 as generally illustrated in FIGS. 20-24. According to one embodiment consistent with the present disclosure, the implant 110 may be delivered to the left ventricle 3 using a delivery catheter 90. The delivery catheter 90 may comprise a lumen configured to receive at least a portion of the rail 30 to advance the delivery catheter 90 proximate to the apex 36 of the left ventricle 3. In addition, the delivery catheter 90 may also comprise a lumen configured to receive at least a portion of the implant 110.

Figure 25A:
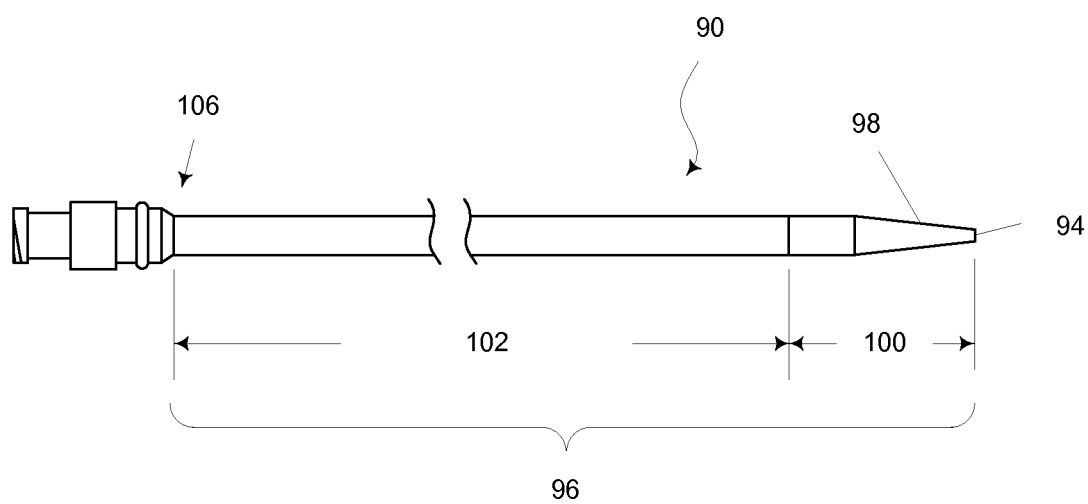
FIG. 25A illustrates a perspective view of an embodiment of a delivery device consistent with the present disclosure.

One example of a delivery catheter 90 consistent with the present disclosure is illustrated in FIG. 25A. The delivery catheter 90 may comprise a dilator 92 configured to be at least partially received within a sheath (not shown in this figured for clarity). The dilator 92 may define at least one lumen 94 configured to receive at least a portion of the rail 30. For example, the lumen 94 may have an internal diameter of approximately 0.038"The dilator 92 may also comprise a shaft 96 including a tapered tip region 98. The shaft 96 may comprise a rigid distal portion 100 (for example, having a durometer of approximately 55 D and a length of approximately 2") and a flexible portion 102 substantially adjacent to the rigid distal portion 100 (for example, having a durometer of 35 D). The combination of the rigid portion 100 and the flexible portion 104 may facilitate advancement of the delivery catheter 90 to the left ventricle 3 while minimizing the risk of kinking or damaging the cardiovascular system. The delivery catheter 90 may also be configured to be steerable. The device and/or method for steering the delivery catheter 90 may include any device or method known to those skilled in the art. The short flexible portion 102 may facilitate bending the dilator 92 along the length of the rail 30 while minimizing kinking when the implant 110 is introduced. The delivery catheter 90 may also comprise a hub 108 (such as, but not limited to, a female luer locking fitting or the like) disposed about the proximal end 106.

Figure 25B:
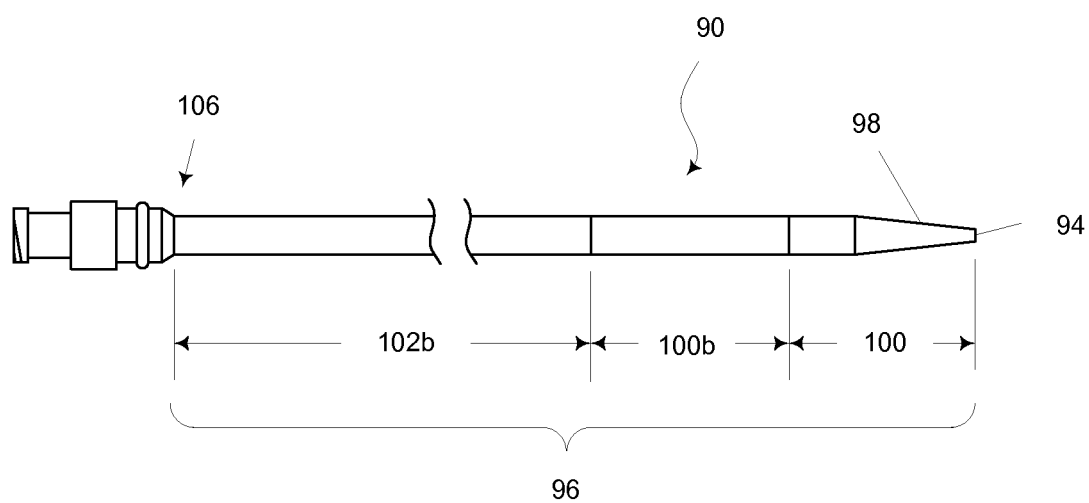
FIG. 25B illustrates a perspective view of another embodiment of a delivery device consistent with the present disclosure.

Another example of a dilator for the steerable catheter is illustrated in FIG. 25B. The shaft 96 may comprise a shaft 96 including a tapered tip region 98. The shaft may comprise a most distal portion 100 having a durometer of approximately 55 D and a length of approximately 2", a central portion 100*b* with a durometer of approximately 35 D and a length of approximately 2", and the remaining proximal length of the shaft 102*b* having a durometer of approximately 75 D. The combination of three regions of varying stiffness may facilitate the advancement of the delivery system and implant where the steerable catheter must make the bend from the site of the transseptal puncture, through the left atrium, and down through the mitral valve.

Figure 21:
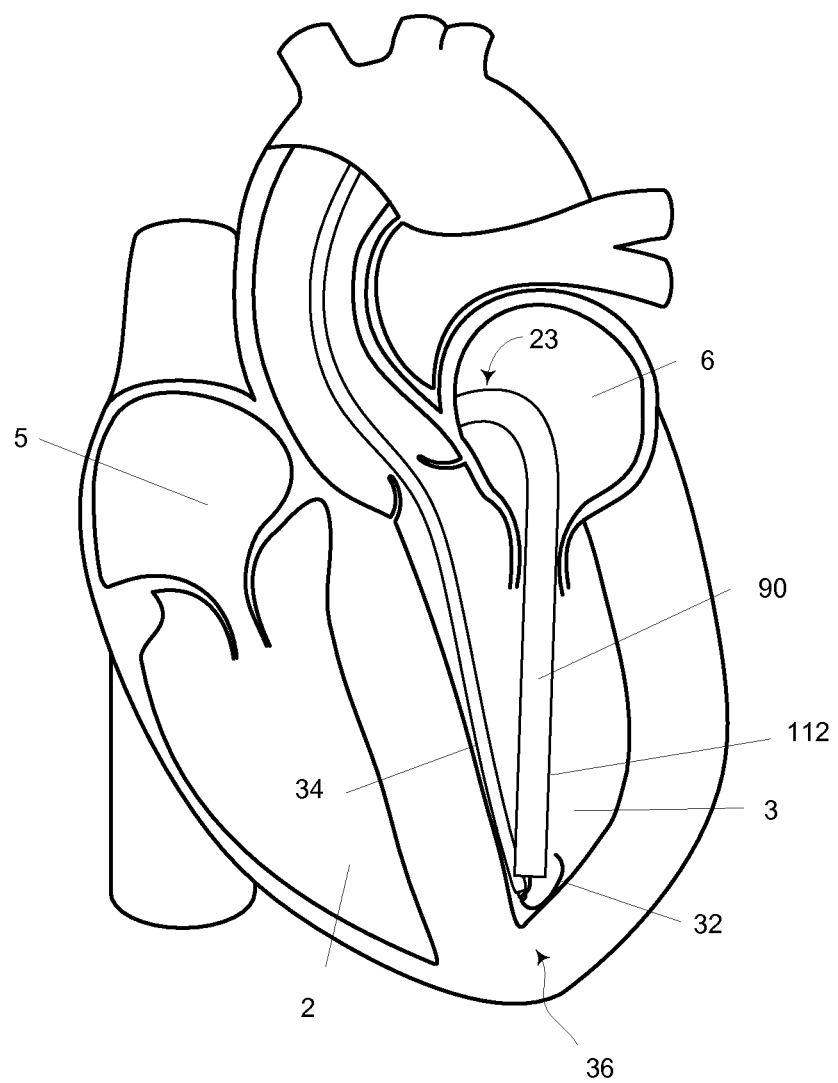
FIG. 21 illustrates a perspective view of an embodiment of a delivery catheter with a dilator removed proximate the apex in the left ventricle consistent with the present disclosure.
Figure 22:
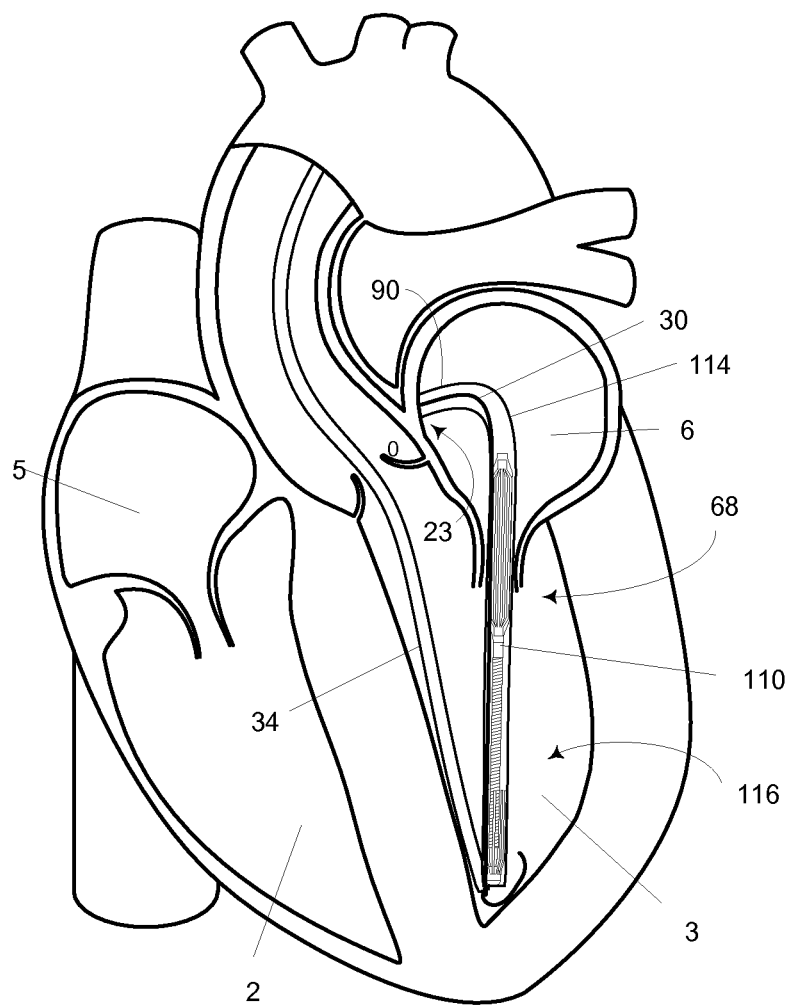
FIG. 22 illustrates a perspective view of an embodiment of an implant advanced within the delivery device over a rail proximate the apex in the left ventricle consistent with the present disclosure.

Turning back to FIGS. 20-24, the delivery catheter 90 may be advanced along the rail 30 through the transseptal puncture 23, through the mitral valve 68, and proximate to the apex 36 within the left ventricle 3 as generally illustrated in FIG. 20. With the delivery catheter 90 proximate the apex 36, the dilator 92 may be removed from the sheath 112 of the delivery catheter 90 as generally illustrated in FIG. 21. The implant 110 may then be received in and advanced through the lumen 114 of the delivery catheter 90 as generally illustrated in FIG. 22. According to one embodiment consistent with the present disclosure, the implant 110 may be loaded into the lumen 114 over the rail 30 using a loading tool. Alternatively, the implant 110 may be loaded into the lumen 114 beside the rail 30, as generally illustrated, using a loading tool. For example, the loading tool may comprise a blow pipe to introduce the implant 110 through the seal of the fitting (for example, but not limited to, a Touhy-Borst fitting) disposed about the proximal end of the delivery catheter 90. Using a flexible shaft pusher, the implant 110 may be advanced through the lumen 114 of the delivery catheter 90 until the implant 110 may be positioned proximate the distal end 116 of the delivery catheter 90 as generally illustrated in FIG. 22. The implant 110 may be seen using one or more visual techniques, for example, one or more of the visual techniques discussed herein.

Figure 26A:
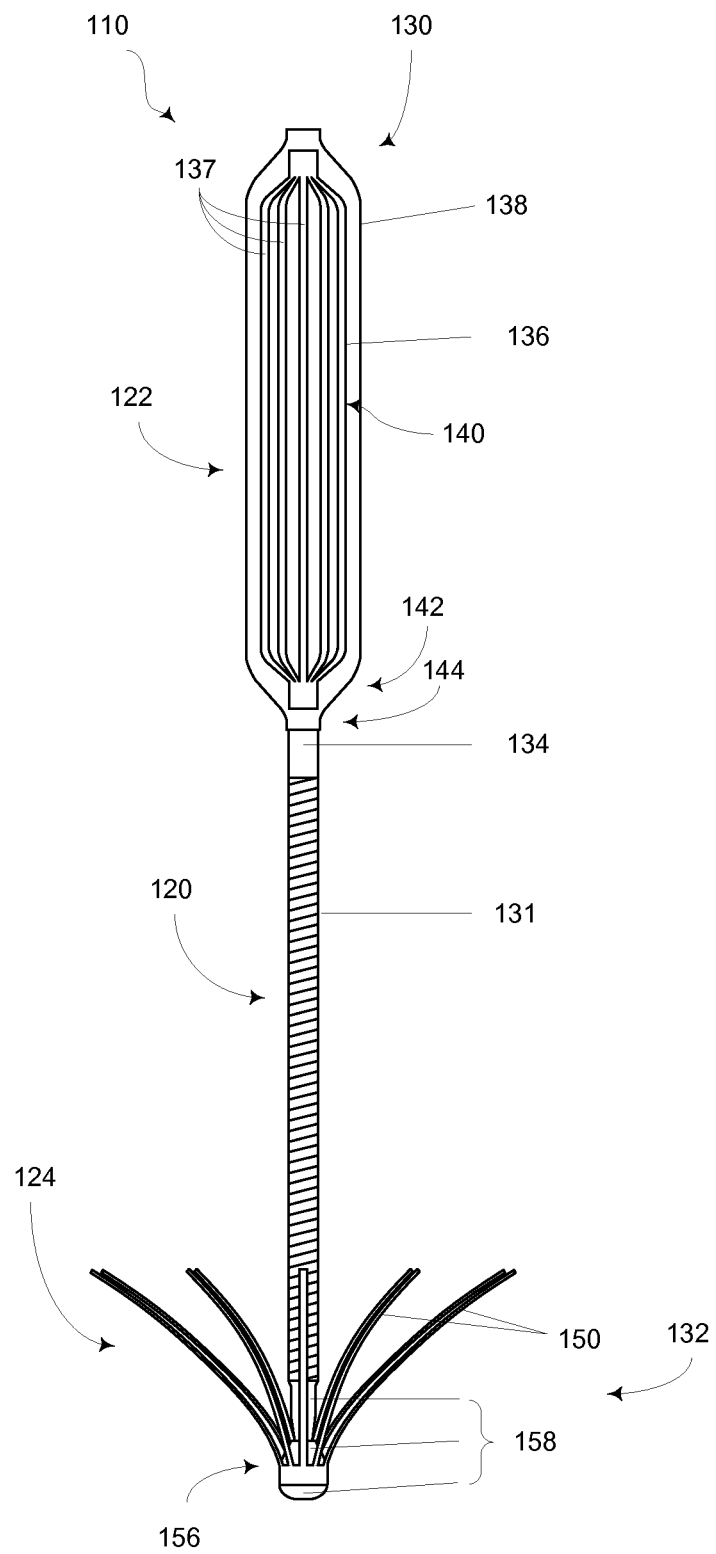

Turning now to FIGS. 26A-26C, one embodiment of the implant 110 consistent with the present disclosure is shown. The implant 110 may comprise a shaft 120, a spacer disposed proximate a proximal end 130 of the shaft 120, and one or more anchoring portions 124 disposed proximate a distal end 132 of the shaft 120. As best seen in FIG. 26B, the implant 110 may define at least one passageway 126 configured to receive the rail 30 such that the implant 110 may be advanced along the length of the rail 30 through the delivery catheter 90 as described herein. For example, the shaft 120, spacer 122 and the anchoring portion 124 may each define a portion of the passageway 126 extending generally from the proximal end 130 to the distal end 132 of the implant 110.

The shaft 120 may comprise a generally flexible member. For example, the shaft 120 may comprise a generally helically wound wire 131 defining a generally cylindrical member. The shaft 120 may be stiff enough to resist and/or prevent buckling/kinking while the implant 110 is being advanced through the delivery catheter 90. The shaft 120 may also be flexible enough to allow a sufficient a degree of movement of the spacer with respect to the anchor to allow the spacer to self-align with respect the cusps of the a heart valve such that the implant 110 may at least partially restrict a flow of blood through the heart valve when in the closed position.

Figure 23:
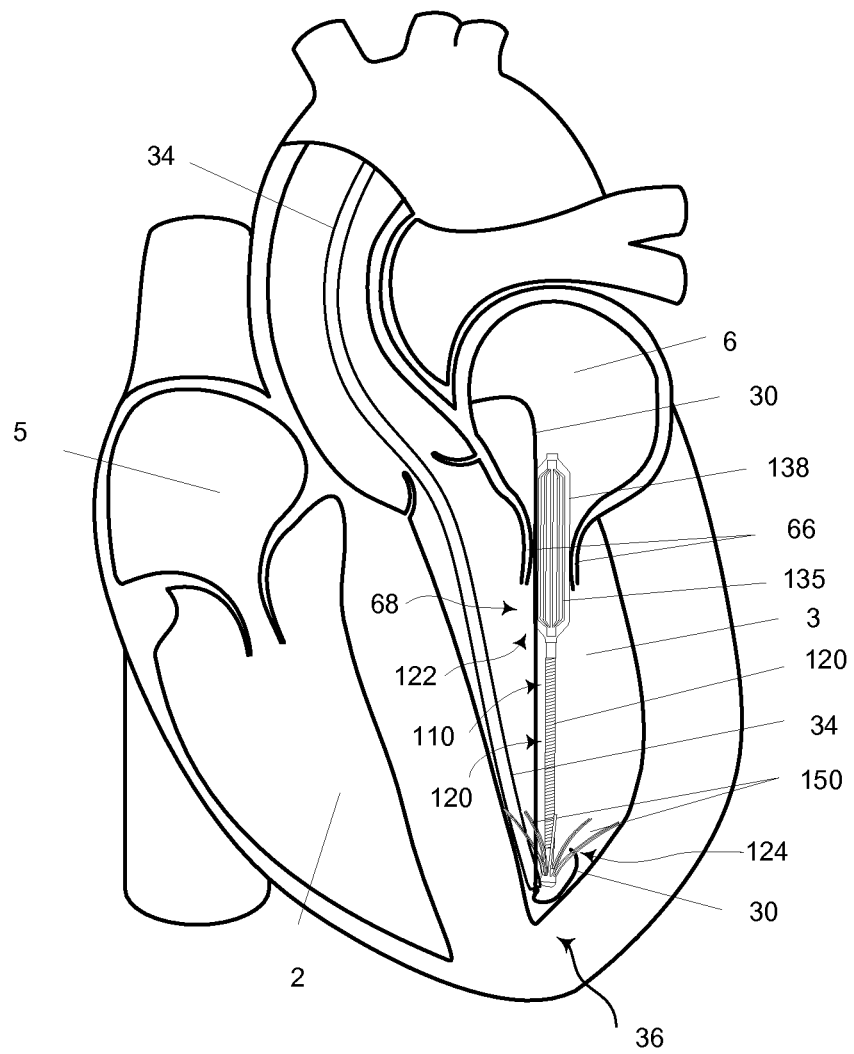
FIG. 23 illustrates a perspective view of an embodiment of an implant deployed proximate the apex in the left ventricle consistent with the present disclosure.
Figure 24:
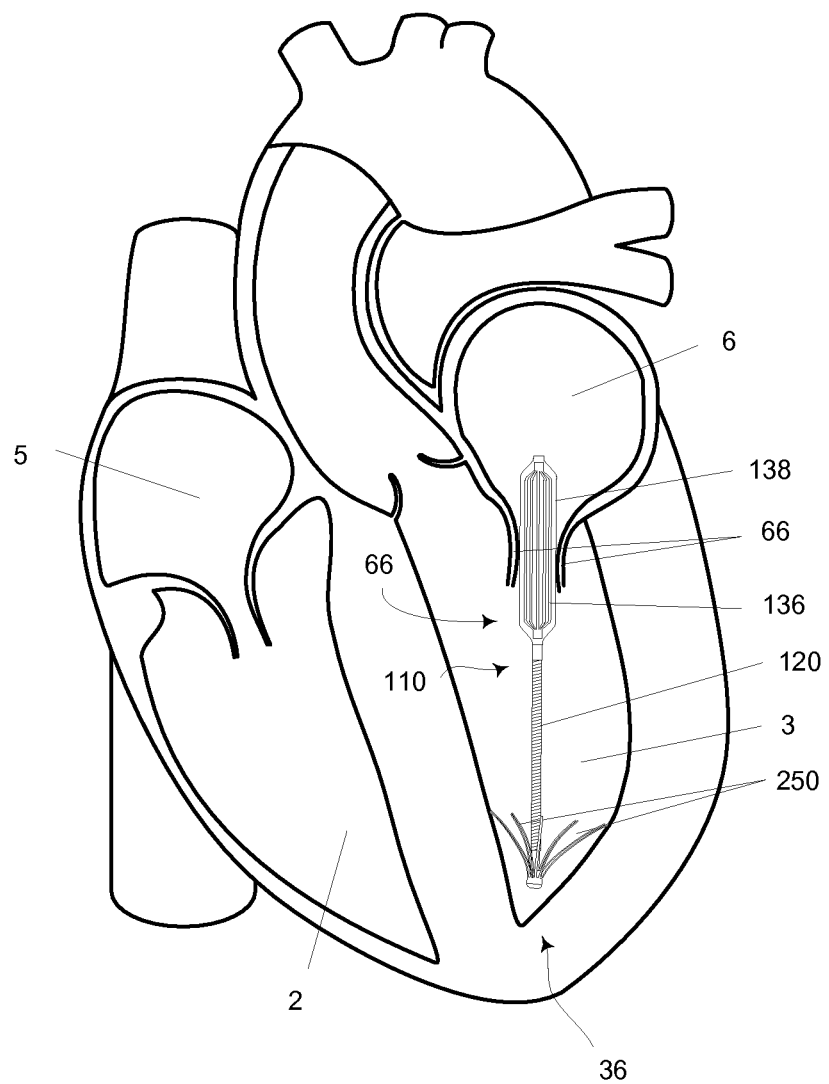
FIG. 24 illustrates a perspective view of an embodiment of an implant proximate the apex in the left ventricle with the retaining device and rail removed consistent with the present disclosure.

The spacer 122 may be coupled to the shaft 120, for example, by way of a collet 134 or the like. The spacer 122 may comprise a spacer cage 136 and a balloon 138 disposed over at least a portion of the outer surface 140 of the spacer cage 136. The spacer cage 136 and/or the balloon 138 may comprise a resiliently flexible structure configured to at least partially collapse from an expanded position as generally illustrated in FIGS. 25A-25C to the retracted or collapsed position as generally illustrated in FIG. 22. When in the collapsed position, the spacer cage 136 and balloon 138 may be configured to be received in and advanced along the lumen 114 of the delivery catheter 90. When in the expanded position, the spacer cage 136 and balloon 138 may be configured to interact and/or cooperate with at least a portion of the native mitral valve 68 to reduce and/or eliminate excessive regurgitation as generally illustrated in FIGS. 23 and 24.

Turning back to FIGS. 25A-25C, the spacer cage 136 may comprise a frame or ribbed structure, for example, a frame of resilient flexible material such as, but not limited to, shape memory materials (for example, but not limited to, nickel titanium compositions (e.g., Nitinol) or the like). The spacer cage 136 may comprise a plurality of support structures 137 extending generally along the longitudinal axis of the implant 110. The support structures 137 may be configured to resiliently bend radially inwardly and/or outwardly, for example, to facilitate loading of the implant 110 within the delivery catheter 90 and/or to facilitate sealing with the mitral valve 68.

The balloon 138 may be configured to be at least partially disposed about the outer surface 140 of the spacer cage 136. The balloon 138 may comprise a resilient flexible, biologically acceptable material. For example, the balloon 138 may comprise Elasteon™ material or the like. The balloon 138 may be coupled or otherwise secured to at least a portion of one or more of the support structures 137 (for example, but not limited to, overmolding, adhesives, and/or laminating) and/or may be only secured about the ends of the spacer cage 136.

The spacer 122 may therefore be configured to interact and/or cooperate with at least a portion of the native mitral valve 68 to reduce and/or eliminate excessive regurgitation. As such, the configuration and/or geometries of the spacer 122 may depend upon the particulars of the condition of the patient's mitral valve 68 and the damage thereto. The implant 110 may have sufficient overall flexibility to facilitate advancement of the implant 110 along the rail 30 within the delivery catheter 90 to minimize the potential of the implant 110 becoming wedged or stuck within the delivery catheter 90. In addition, the implant 110 may also have sufficient overall rigidity to maintain the spacer 122 within the mitral valve 68 such that the implant 110 performs as intended.

The implant 110 may also comprise an anchor portion 124. The anchor portion 124 may be configured to generally secure the position of the implant 110 within the heart 1, and more specifically, to generally secure the position of the implant 110 proximate to the apex 36 and the spacer 122 within the mitral valve 68. According to one embodiment consistent with the present disclosure, the anchor portion 124 may comprise a plurality of tines 150 configured to be coupled to and/or otherwise attached to or engage native coronary tissue. The plurality of tines 150 may extend generally radially outwardly from a distal end 132 of the implant 110 towards a proximal end 130 (e.g., generally radially outwardly from the anchor portion 124 towards the spacer 122). The plurality of tines 150 may have a generally arcuate shape configured to engage with the generally conical shape of the region of the apex 36 in the left ventricle 3 as generally illustrated in FIGS. 23 and 24.

The anchor portion 124 may optionally comprise a pivot 156 configured to allow the shaft 120 and/or the spacer 122 to pivot and/or rotate relative to the anchor portion 124. For example, the pivot 156 may comprise a gimbal assembly 158 as generally illustrated in FIG. 26C. The pivot 156 may allow the implant 110 to self-center itself within the mitral valve 68, thereby allowing the implant 110 to be less precisely secured within the left ventricle 3.

Turning now to FIGS. 22-24, the implant 110 may be deployed from the delivery catheter 90 by urging the implant 110 forward while simultaneously withdrawing the delivery catheter 90. As the implant 110 exits the delivery catheter 90, the anchoring portion 124 (for example, the plurality of tines 150) which were compressed while received in the delivery catheter 90 may expand generally radially outwardly to engage the native coronary tissue within the left ventricle 3 as generally illustrated in FIG. 23. Once the anchor portion 110 has been secured within the left ventricle 3, the retaining device 34 may release the rail 30 and the rail 30 and the retaining device 34 may be withdrawn as generally illustrated in FIG. 24. The position and operation of the implant 110 may be confirmed by introducing contrast fluid into the left ventricle 3 to verify how much (if any) regurgitation still exists.

Another embodiment of the implant 210 consistent with the present disclosure is generally illustrated in FIGS. 27A-27E. The implant 210 may comprise a shaft 220, a spacer disposed proximate a proximal end 230 of the shaft 220, and one or more anchoring portions 224 disposed proximate a distal end 232 of the shaft 220, and a releasable coupler 221 disposed about the proximal 230 end. The shaft 220 may comprise a generally flexible member. For example, the shaft 220 may comprise a generally helically wound wire 231 defining a generally cylindrical member. The shaft 220 may be stiff enough to resist and/or prevent buckling/kinking while the implant 210 is being advanced through the delivery catheter 90.

Figure 27B:
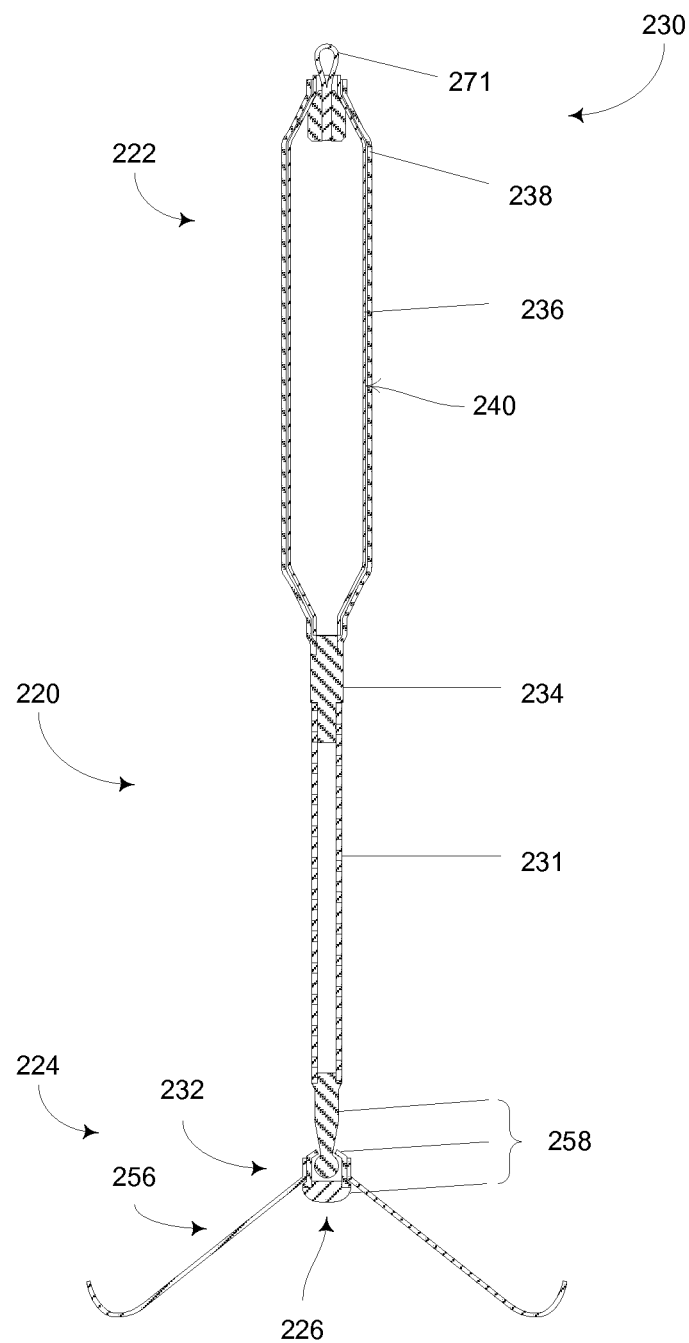
Figure 27C:
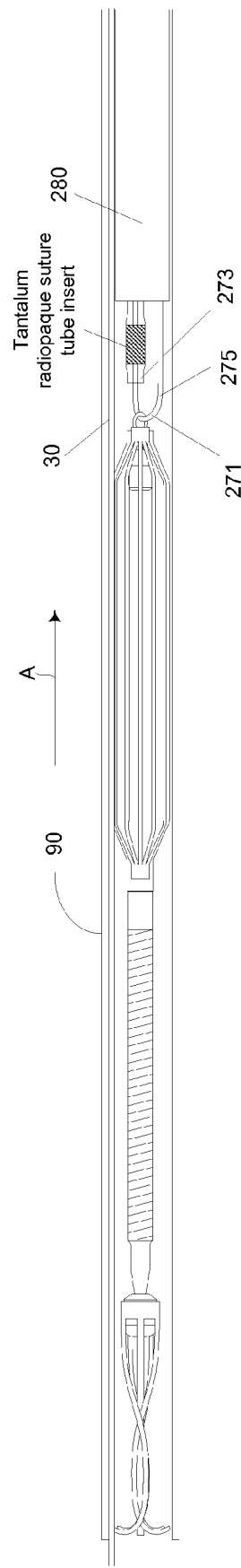
FIG. 27C-27D illustrate a perspective view of an embodiment of an implant loaded within the delivery catheter consistent with the present disclosure.
Figure 27D:
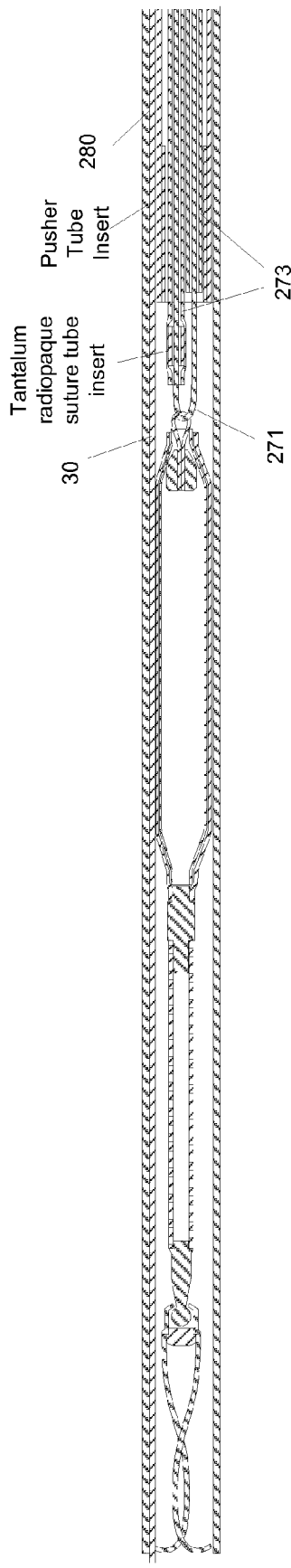
Figure 28:
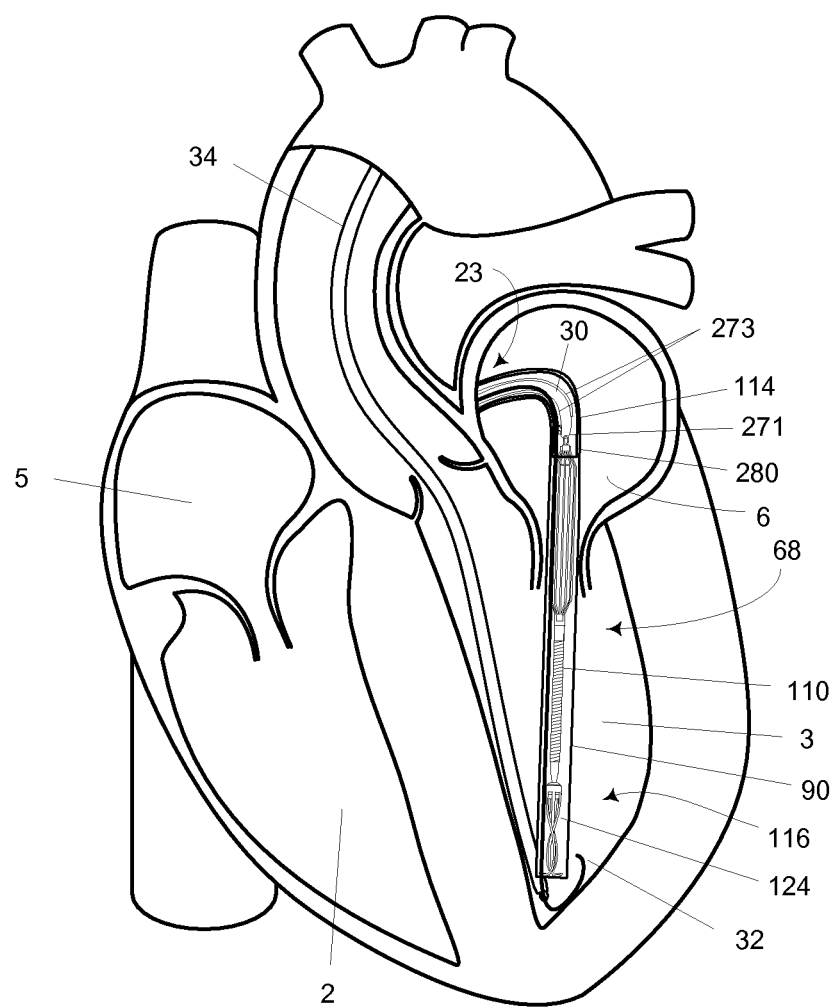
FIG. 28 illustrates a perspective view of another embodiment of an implant advanced within the delivery device over the rail proximate the apex in the left ventricle consistent with the present disclosure.
Figure 29:
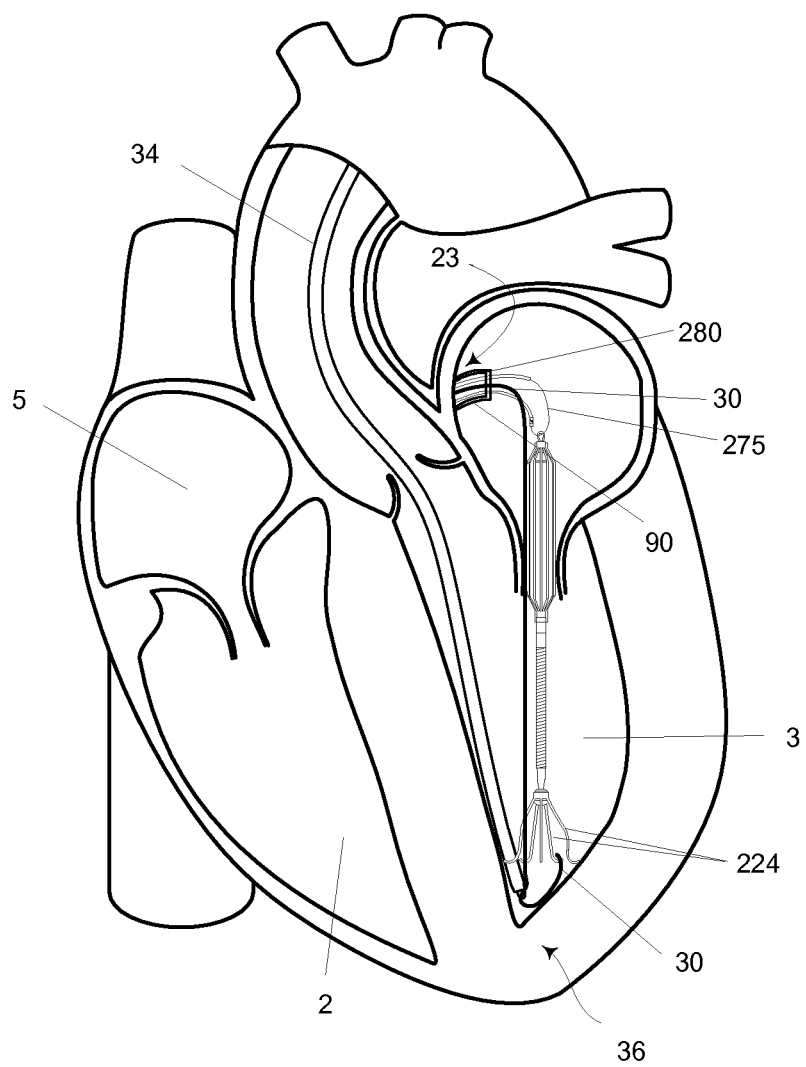
FIG. 29 illustrates a perspective view of another embodiment of an implant deployed proximate the apex in the left ventricle consistent with the present disclosure.
Figure 30A:
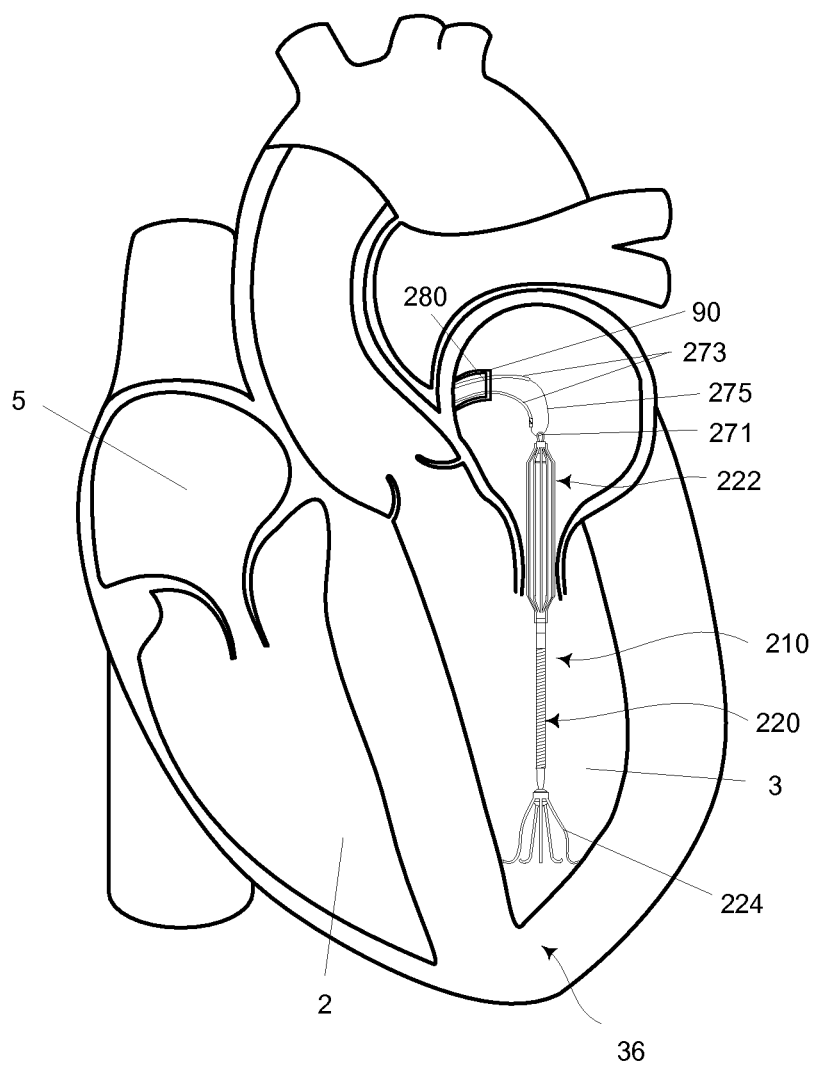
FIG. 30A illustrates a perspective view of another embodiment of an implant proximate the apex in the left ventricle with the retaining device and rail removed consistent with the present disclosure.
Figure 30B:
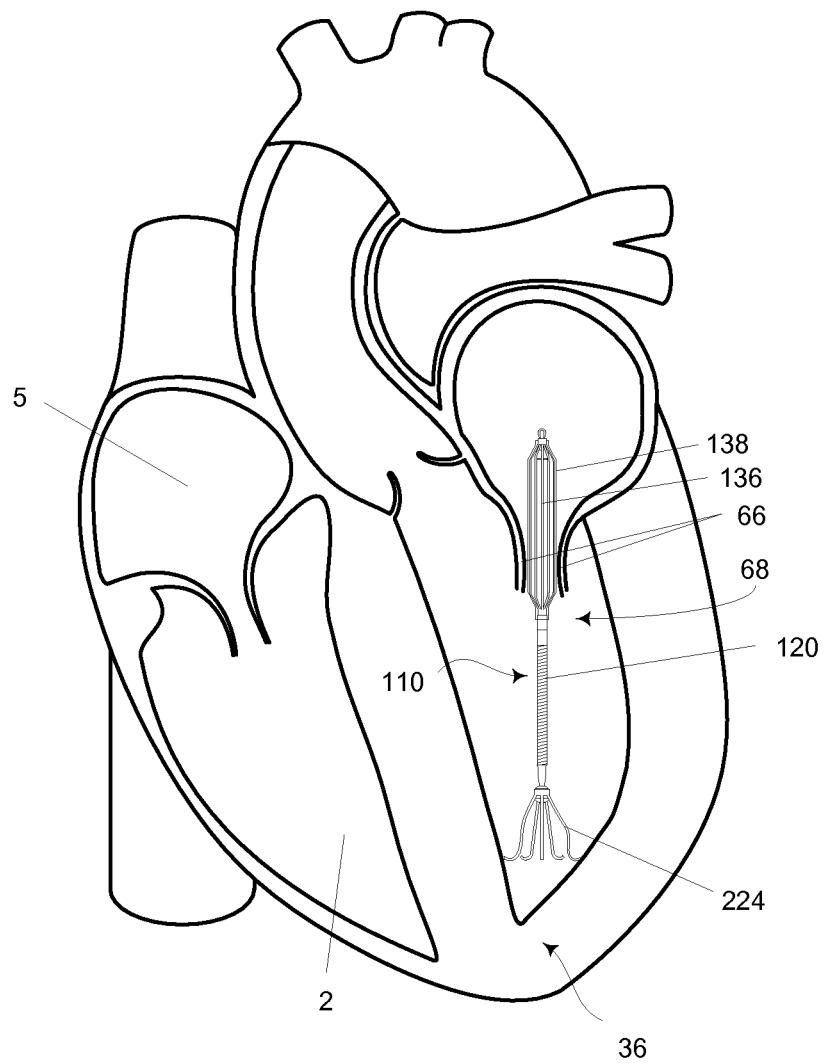
FIG. 30B illustrates a perspective view of another embodiment of an implant proximate the apex in the left ventricle.
Figure 31:
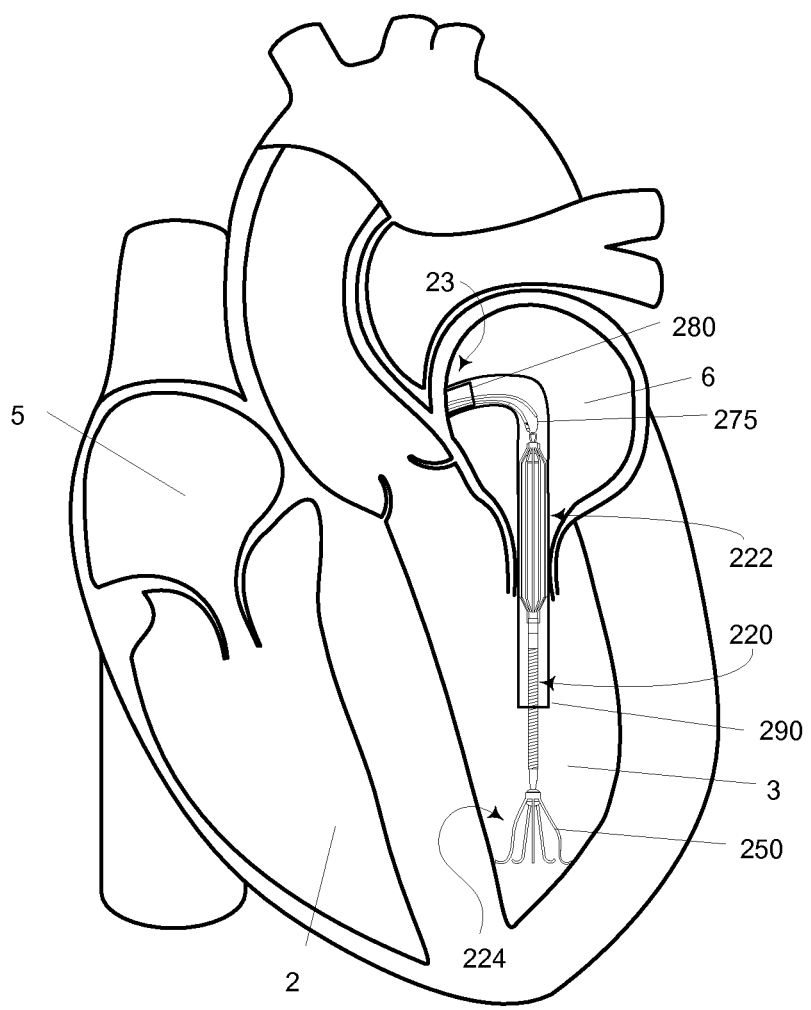
FIG. 31 illustrates a perspective view of an embodiment for removing an implant deployed proximate the apex in the left ventricle.

The spacer 222 may be coupled to the shaft 220, for example, by way of a collet 234 or the like. The spacer 222 may comprise a spacer cage 236 and a balloon 238 disposed over at least a portion of the outer surface 240 of the spacer cage 236. The spacer cage 236 and/or the balloon 238 may comprise a resiliently flexible structure configured to at least partially collapse from an expanded position as generally illustrated in FIGS. 27A-27B to the retracted or collapsed position as generally illustrated in FIGS. 27C-27E when loaded within the delivery catheter 90. When in the collapsed position, the spacer cage 236 and balloon 238 may be configured to be received in and advanced along the lumen 114 of the delivery catheter 90 as generally illustrated in FIG. 28. When in the expanded position, the spacer cage 236 and balloon 238 may be configured to interact and/or cooperate with at least a portion of the native mitral valve 68 to reduce and/or eliminate excessive regurgitation as generally illustrated in FIGS. 29 and 30.

According to one embodiment, the spacer cage 236 may comprise a frame or ribbed structure, for example, a frame of resilient flexible material such as, but not limited to, shape memory materials (for example, but not limited to, nickel titanium compositions (e.g., Nitinol) or the like). The spacer cage 236 may comprise a plurality of support structures 237 extending generally along the longitudinal axis of the implant 210. The support structures 237 may be configured to resiliently bend radially inwardly and/or outwardly, for example, to facilitate loading of the implant 210 within the delivery catheter 90 and/or to facilitate sealing with the mitral valve 68.

The balloon 238 may be configured to be at least partially disposed about the outer surface 240 of the spacer cage 236. The balloon 238 may comprise a resilient flexible, biologically acceptable material. For example, the balloon 238 may comprise Elasteon™ material or the like. The balloon 388 may be coupled or otherwise secured to at least a portion of one or more of the support structures 237 (for example, but not limited to, overmolding, adhesives, and/or laminating) and/or may be only secured about the ends of the spacer cage 236.

The spacer 222 may therefore be configured to interact and/or cooperate with at least a portion of the native mitral valve 68 to reduce and/or eliminate excessive regurgitation. As such, the configuration and/or geometries of the spacer 222 may depend upon the particulars of the condition of the patient's mitral valve 68 and the damage thereto. The implant 210 may have sufficient overall flexibility to facilitate advancement of the implant 210 along the delivery catheter 90 to minimize the potential of the implant 210 becoming wedged or stuck within the delivery catheter 90. In addition, the implant 210 may also have sufficient overall rigidity to maintain the spacer 222 within the mitral valve 68 such that the implant 210 performs as intended.

The implant 210 may also comprise an anchor portion 224. The anchor portion 224 may be configured to generally secure the position of the implant 210 within the heart 1, and more specifically, to generally secure the position of the implant 210 proximate to the apex 36 and the spacer 222 within the mitral valve 68. According to one embodiment consistent with the present disclosure, the anchor portion 224 may comprise a plurality of tines 250 configured to be coupled to and/or otherwise attached to or engage native coronary tissue. The plurality of tines 250 may extend generally radially outwardly from a distal end 230 of the implant 210 and away from the proximal end 232 (e.g., generally radially outwardly from the anchor portion 224 and away from the spacer 222). The plurality of tines 250 may have a generally arcuate shape configured to engage with the generally conical shape of the region of the apex 36 in the left ventricle 3 as generally illustrated in FIGS. 29-30.

The anchor portion 224 may optionally comprise a pivot 256 configured to allow the shaft 220 and/or the spacer 222 to pivot and/or rotate relative to the anchor portion 224. For example, the pivot 256 may comprise a gimbal assembly 258. The pivot 256 may allow the implant 210 to self-center itself within the mitral valve 68, thereby allowing the implant 210 to be less precisely secured within the left ventricle 3.

The implant 210 may also include one or more releasable couplers 221 disposed about the proximal 230 end as mentioned above. The releasable couplers 221 may be configured to releasably engage a retractor 273 and may allow the implant 210 to be at least partially retracted back into the delivery catheter 90 after exiting delivery catheter 90 within the heart 1. This may allow the implant 210 to be test fit within the left ventricle 3 and/or may allow the implant 210 to be removed after implantation.

The releasable coupler 221 may comprise one or more apertures and/or bails 271 configured to receive a suture 275 or the like as best seen in FIGS. 27C-27E. The bail 271 may be mounted, secured or otherwise coupled to the implant 210 such as, but not limited to, the spacer 222, and may extend generally away from the proximal end 230 of the implant 210. For example, the bail 271 may be coupled to the spacer cage 236 and may be an integral, unitary component thereof. The bail 271 may also be coupled to the anchor portion 222 (for example, within a cavity defined by the anchor portion 222, with one or more fasteners 299 (as best seen in FIG. 27D). The suture 275 may comprise a length of wire configured to form a loop disposed though the bail 271 and extending through the delivery catheter 90. The releasable coupler 221 and/or the retractor 273 may also comprise any devices configured to allow the implant 210 to be at least partially withdrawn back into the delivery catheter 90 and to allow the implant 210 to be released once in place within the heart.

Consistent with one embodiment of the present disclosure, the implant 210 loaded in to the delivery catheter 90 as generally described herein. Once the implant 210 is loaded in the delivery catheter 90, a pusher 280 (FIGS. 27C-27E) configured to be received within the delivery catheter 90 may also be loaded. The pusher 280 may comprise a shaft 281 coupled to a body 283 configured to generally contact proximal end of the implant 210 and to urge the implant 210 along the length of the rail 30 within the delivery catheter 90 generally towards the left ventricle 3 until the anchor portion 224 of the implant 210 is proximate the distal end of the delivery catheter 90 as generally illustrated in FIG. 28. Optionally, the pusher 280 may be cannulated to define at least one longitudinally disposed internal passageway configured to receive the rail 30 and/or the retractor 273. The rail 30 and the retractor 273 may be disposed within the same or different passageways within the pusher 280. The pusher 280 may also be configured to allow one or more of the rail 30 and the retractor 273 to pass between the outside of the pusher 280 and the inside of the delivery catheter 90. Once the placement of the distal end of the delivery catheter 90 has been confirmed (e.g., proximate the apex 36 within the left ventricle 3), the implant 210 may be urged out of the delivery catheter 90 and engage the native coronary tissue of the left ventricle 3, for example, by urging the implant 210 with the pusher 280 and/or retracting the delivery catheter 90 back through the mitral valve 68 as generally illustrated in FIG. 29. Once at least a portion of the anchor portion 224 exits the delivery catheter 90, the tines 250 may begin to expand radially outwardly and engage the native coronary tissue of the left ventricle 3 proximate the apex 36.

After confirming the placement of the implant 210 within the left ventricle 3 and mitral valve 68, the rail 30 may be released from the retaining device 34 and the retaining device 34 and/or the rail 30 may be removed from the heart 1 as generally illustrated in FIG. 30. After confirming the operation of the implant 210, the retractor 273 may be released from the implant 210 by pulling one end of the suture 275 generally towards the proximal end of the delivery catheter 90 until one end of the suture 275 passes through the bail 271 and the retractor 273 and the delivery device 90 may be withdrawn from the heart 1.

Figure 32:
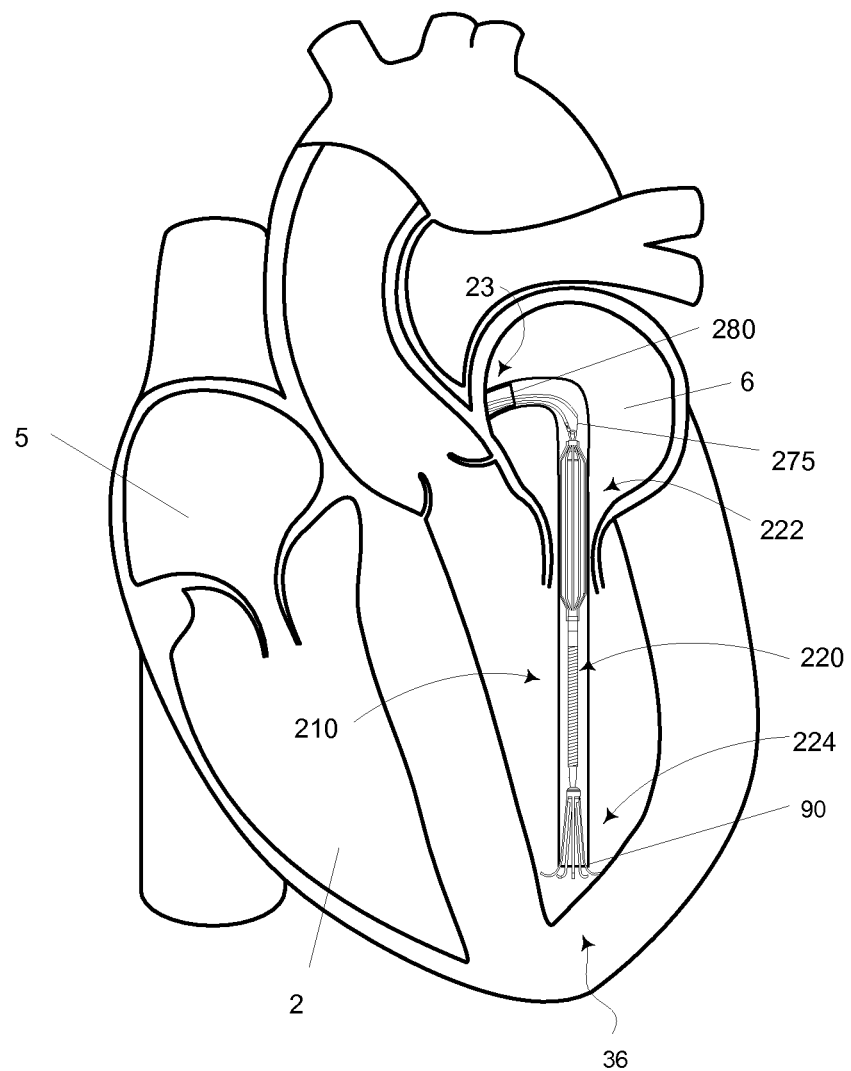
FIG. 32 illustrates a perspective view of an embodiment for removing an implant deployed proximate the apex including contracting the anchoring device.

The implant 210 may be retracted and/or withdrawn after delivery and/or partial delivery within the heart 1 or delivery catheter 90 (for example, due to improper placement within the heart 1 and/or improper operation) by pulling both ends of the suture 275 generally towards the proximal end of the delivery catheter 90 and/or pushing the delivery catheter 90 over the implant 210 as generally illustrated in FIGS. 32-32. Because the plurality of tines 250 may extend radially outwardly and away from the spacer 222, the tines 250 may contract as the implant 210 is loaded back into the distal end of the delivery catheter 90 and may also disengage the anchor portion 224 from the coronary tissue.

An implant consistent with the present disclosure may also comprise other embodiments, for example, but not limited to, one or more of the implants as described in U.S. application Ser. No. 11/258,828 filed Oct. 26, 2005 and entitled HEART VALVE IMPLANT; Ser. No. 11/940,724 filed on Nov. 15, 2007 and entitled HEART REGURGITATION METHOD AND APPARATUS; Ser. No. 11/748,121 filed on May 14, 2007 and entitled BALLOON MITRAL SPACER; Ser. No. 11/748,138 filed on May 14, 2007 and entitled SOLID CONSTRUCT MITRAL SPACER; Ser. No. 11/940,674 filed on Nov. 15, 2007 and entitled MITRAL SPACER; Ser. No. 11/748,147 filed on May 14, 2007 and entitled SAFETY FOR MITRAL VALVE PLUG; and Ser. No. 11/940,694 filed on Nov. 15, 2007 and entitled IMPLANT DELIVERY SYSTEM AND METHOD, all of which are fully incorporated herein by reference.

The size and/or configuration of the implant may be determined based on a comparison with a reference size. For example, a catheter having a known outer diameter and/or calibrated length markings (such as, but not limited to, the radiopague markings 90a-90n described herein) may be used as a reference for determining the length of the implant and/or the diameter of the spacer. Consistent with another embodiment, the reference (such as, but not limited to, a stainless steel ball or the like) may also be placed on the patient's body which may show up on fluoroscopy when viewing the mitral valve. The reference may be configured to reduce and/or eliminate the potential for foreshortening. The length of the implant may be long enough such that when spacer is at least partially disposed within the mitral valve when the implant is secured within the left ventricle, but not too long that it may damage the left atrium. The diameter of the implant may be large enough to reduce the regurgitation across the mitral valve to a satisfactory level (i.e., a level which appropriate based on the patient's medical condition) but not too large that it reduces the flow through the mitral valve below a minimum threshold. It may be appreciated that the upper and lower limits for the length and/or diameter may depend upon the patient's condition/situation. Other methods and/or devices for sizing and/or shaping the implant may also be used with the present disclosure.

As described above, a heart valve implant consistent with the present disclosure may be used in the treatment mitral valve regurgitation. However, the heart valve implant as well as its associated methods may also suitably be employed in other applications, e.g., as an implant associated with one of the other valves of the heart, etc. The present disclosure should not, therefore, be construed as being limited to use for reducing and/or preventing regurgitation of the mitral valve.

As mentioned above, the present disclosure is not intended to be limited to an apparatus, system or method which must satisfy one or more of any stated or implied object or feature of the present disclosure and should not be limited to the preferred, exemplary, or primary embodiment(s) described herein. The foregoing description of the present disclosure has been presented for purposes of illustration and description. It is not intended to be exhaustive or to limit the invention to the precise form disclosed. Obvious modifications or variations are possible in light of the above teachings. The embodiments were chosen and described to provide the best illustration of the principles of the present disclosure and its practical application to thereby enable one of ordinary skill in the art to utilize the present disclosure in various embodiments and with various modifications as is suited to the particular use contemplated. All such modifications and variations are within the scope of the present disclosure when interpreted in accordance with breadth to which it is fairly, legally and equitably entitled.

What is claimed is:

1. A heart valve implant comprising:
 a spacer comprising a cage and a resiliently flexible balloon disposed over at least a portion of the spacer cage, wherein said resiliently flexible balloon is configured to contact at least a portion of at least one cusp of a mitral valve to at least partially restrict a flow of blood through said mitral valve in a closed position and to allow blood flow through said mitral valve in an open position of the valve;
 a shaft having a first end configured to be coupled to said spacer;
 an anchor configured to be coupled to a second end of said shaft, said anchor configured to removably secure said implant to engage native cardiac tissue within a ventricle; and
 a gimbal pivotally coupling said anchor to a second end of said shaft, said gimbal configured to provide a degree of movement with respect to said anchor when said anchor is secured in said tissue to allow said spacer to self-align with respect to said at least a portion of said at least one cusp of said mitral valve to at least partially restrict a flow of blood through said mitral valve in said closed position.

2. The implant of claim 1, wherein said shaft is configured to bend to provide said degree of movement.

3. The implant of claim 1, wherein said spacer is configured to at least partially expand from a collapsed configuration wherein said spacer is configured to be received in and advanced along a lumen of a delivery catheter to an expanded configuration wherein said spacer is configured to contact at least a portion of at least one cusp of a mitral valve to at least partially restrict a flow of blood through said mitral valve in a closed position.

4. The implant of claim 3, wherein said spacer is generally cylindrical.

5. The implant of claim 4, wherein said spacer further comprises a generally conically shaped region proximate a first and a second end region of said spacer.

6. The implant of claim 1, wherein said cage is resiliently flexible and coupled to said first end of said shaft.

7. The implant of claim 6, wherein said resiliently flexible cage further comprises a frame or ribbed structure configured to provide additional support to said resiliently flexible balloon.

8. The implant of claim 7, wherein said resiliently flexible cage comprises a plurality of support ribs extending generally along a longitudinal axis of said implant.

9. The implant of claim 8, wherein said plurality of ribs are configured to resiliently bend radially inwardly and outwardly.

10. The implant of claim 9, wherein said resiliently flexible cage comprises a shape memory material.

11. The implant of claim 1, wherein said anchor comprises a base and a plurality of tines extending generally outwardly from said base, said plurality of tines configured to removably engage native cardiac tissue to removably secure said implant within said heart.

12. The implant of claim 11, wherein said plurality of tines extend generally radially outwardly from said base towards said spacer.

13. The implant of claim 12, wherein said anchor comprises a generally inverted umbrella configuration.

14. The implant of claim 1, wherein said implant further comprises at least one releasable coupler disposed at a proximal end of the shaft configured to releasably engage a delivery device configured to position said implant within said heart.

15. The implant of claim 1, wherein said spacer is configured to contact and seal against said portion of said at least one cusp of said mitral valve to reduce regurgitation through said mitral valve.

16. A heart valve implant comprising:
a spacer comprising a cage and a resiliently flexible balloon disposed over at least a portion of the cage configured to contact at least a portion of at least one cusp of a mitral valve to at least partially restrict a flow of blood through said mitral valve in a closed position and to allow the flow of blood through said mitral valve in an open position of the valve;
a shaft having a first end configured to be coupled to said spacer; and
an anchor configured to removably secure said implant to native ventricular cardiac tissue, wherein said anchor comprises a base and a plurality of tines extending generally outwardly from said base and generally towards said spacer, said plurality of tines configured to removably engage native ventricular cardiac tissue to removably secure said implant within said heart;
wherein said spacer is operatively coupled to said anchor to provide a degree of movement with respect to the anchor when said anchor is secured in said tissue to allow the spacer to self-align with respect to said at least a portion of said at least one cusp of said mitral valve to at least partially restrict a flow of blood through said mitral valve in said closed position.

17. The implant of claim 16, wherein said spacer is configured to contact and seal against said portion of said at least one cusp of said mitral valve to reduce regurgitation through said mitral valve.

18. A heart valve implant comprising:
a spacer comprising a cage and a resiliently flexible balloon disposed over at least a portion of the spacer cage configured to contact at least a portion of at least one cusp of a mitral valve to at least partially restrict a flow of blood through said mitral valve in a closed position and to allow blood flow through said mitral valve in an open position of the valve;
a shaft having a first end configured to be coupled to said spacer; and
an anchor configured to be coupled to a second end of said shaft, said anchor comprising a base and a plurality of tines extending generally outwardly and away from said base and generally towards said spacer, said plurality of tines configured to removably secure said implant to native cardiac tissue within a ventricle of a heart.

19. The implant of claim 18, wherein said spacer is operatively coupled to said anchor to provide a degree of movement with respect to the anchor to allow the spacer to self-align with respect to said at least a portion of said at least one cusp of said mitral valve to at least partially restrict a flow of blood through said mitral valve in said closed position.

20. The implant of claim 19, wherein said second end of said shaft is pivotally coupled to said anchor to provide said degree of movement.

21. The implant of claim 20, further comprising a gimbal pivotally coupling said second end of said shaft to said anchor.

22. The implant of claim 19, wherein said shaft is configured to bend to provide said degree of movement.

23. The implant of claim 18, wherein said spacer is configured to contact and seal against said portion of said at least one cusp of said mitral valve to reduce regurgitation through said mitral valve.

* * * * *